United States Patent
Flynn et al.

(10) Patent No.: US 8,202,513 B2
(45) Date of Patent: Jun. 19, 2012

(54) ARYL POTASSIUM CHANNEL BLOCKERS AND USES THEREOF

(75) Inventors: Bernard Luke Flynn, Vermont (AU); Jonathan Bayldon Baell, Ivanhoe (AU); Jason Hugh Chaplin, DoubleView (AU); Gurmit Singh Gill, Craigieburn (AU); Damian Wojciech Grobelny, Watsonia (AU); Andrew John Harvey, Goodwood (AU); Jorgen Alvar Mould, Semaphore (AU); Dharam Paul, Torrensville (AU)

(73) Assignee: Bionomics Limited, Thebarton, South Australia (AU)

( * ) Notice: Subject to any disclaimer, the term of this patent is extended or adjusted under 35 U.S.C. 154(b) by 0 days.

(21) Appl. No.: 12/681,763

(22) PCT Filed: Oct. 3, 2008

(86) PCT No.: PCT/AU2008/001480
§ 371 (c)(1),
(2), (4) Date: Jul. 7, 2010

(87) PCT Pub. No.: WO2009/043117
PCT Pub. Date: Apr. 9, 2009

(65) Prior Publication Data
US 2010/0297077 A1    Nov. 25, 2010

Related U.S. Application Data

(60) Provisional application No. 60/977,538, filed on Oct. 4, 2007.

(51) Int. Cl.
| | |
|---|---|
| A61K 38/21 | (2006.01) |
| A61K 31/138 | (2006.01) |
| A61K 31/4402 | (2006.01) |
| A61K 31/5375 | (2006.01) |
| A61K 31/4453 | (2006.01) |
| A61K 31/40 | (2006.01) |
| A61K 31/4965 | (2006.01) |
| A61K 31/54 | (2006.01) |
| A61K 31/4174 | (2006.01) |
| A61K 31/4196 | (2006.01) |
| A61K 31/397 | (2006.01) |
| A61K 31/198 | (2006.01) |
| A61K 39/395 | (2006.01) |
| C07C 215/64 | (2006.01) |
| A61P 29/00 | (2006.01) |
| A61P 3/10 | (2006.01) |
| A61P 25/28 | (2006.01) |
| C07D 213/54 | (2006.01) |
| C07D 265/30 | (2006.01) |
| C07D 211/34 | (2006.01) |
| C07D 211/74 | (2006.01) |
| C07D 207/08 | (2006.01) |
| C07D 241/18 | (2006.01) |
| C07D 279/12 | (2006.01) |
| C07D 233/60 | (2006.01) |
| C07D 249/08 | (2006.01) |
| C07D 205/04 | (2006.01) |

(52) U.S. Cl. ............... 424/85.6; 424/133.1; 514/210.01; 514/227.5; 514/239.2; 514/252.1; 514/277; 514/315; 514/383; 514/399; 514/428; 514/567; 514/646; 514/647; 544/174; 544/408; 544/58.2; 546/242; 546/248; 546/340; 548/267.8; 548/341.1; 548/575; 548/950

(58) Field of Classification Search .................. None
See application file for complete search history.

(56) References Cited

U.S. PATENT DOCUMENTS

| | | | |
|---|---|---|---|
| 3,250,767 | A | 5/1966 | Bencze |
| 5,126,351 | A | 6/1992 | Luzzio et al. |
| 5,494,895 | A | 2/1996 | Garcia et al. |
| 6,051,590 | A | 4/2000 | Bao et al. |
| 6,077,680 | A | 6/2000 | Kem et al. |
| 2004/0224936 | A1 | 11/2004 | Chiba et al. |
| 2006/0079535 | A1 | 4/2006 | Wulff et al. |

FOREIGN PATENT DOCUMENTS

| | | |
|---|---|---|
| EP | 0 338 937 B1 | 12/1993 |
| JP | 51095033 | 8/1976 |
| JP | 10-316853 A | 12/1998 |
| JP | 10316617 | 12/1998 |
| JP | 10316853 | 12/1998 |
| WO | WO 97/16437 A1 | 5/1997 |
| WO | WO 97/16438 A1 | 5/1997 |
| WO | WO 03/076407 A1 | 9/2003 |
| WO | WO 03/076424 A1 | 9/2003 |
| WO | WO 2008/040057 A1 | 4/2008 |

OTHER PUBLICATIONS

Beneza, caplus an 1966:438312.*
Diabetes, 2011, http://www.diabetes.org/diabetes-basics/prevention/.*
Ion Channel, 2011, http://www.icagen.com/technology/ionchannels.html.*
Bhaskar et al., caplus an 1975:31081.*

(Continued)

*Primary Examiner* — Sun Jae Loewe
(74) *Attorney, Agent, or Firm* — Knobbe Martens Olson & Bear LLP

(57) ABSTRACT

The present invention relates to compounds useful in the modulation of potassium channel activity in cells, in particular the activity of Kv1.3 channels found in T cells. The invention also relates to the use of these compounds in the treatment or prevention of autoimmune and inflammatory diseases, including multiple sclerosis, pharmaceutical compositions containing these compounds and methods for their preparation.

21 Claims, No Drawings

OTHER PUBLICATIONS

Baell, J. et al. 2004 "Khellinone Derivatives as Blockers of Voltage-Gated Potassium Channel Kv1.3: Synthesis and Immunosuppressive Activity." *J. Med. Chem.* 47(9):2326-2336.

Whitelaw, M. L. et al. 1991 "Synthesis and sensory evaluation of ring-substituted dihydrochalcone sweeteners." *Journal of Agricultural and Food Chemistry* 39(1):44-51.

Cianci, J. et al. 2008 Synthesis and biological evaluation of chalcones as inhibitors of the voltage-gated potassium channel Kv1.3. *Bioorg. & Med. Chem. Lett.* 18:2055-2061.

Harvey, A.J. et al. 2006 "A new class of Blockers of the Voltage-Gated Potassium Channel Kv1.3 via Modification of the 4- or 7-Position of Khellinone" *J. Med. Chem.* 49:1433-1441.

Satuluri, V.S.A.K. et al. 2008 "A Quantitative Structure-Activity Relationship Study on Some Series of Potassium Channel Blockers" *Med. Chem.* 5(1):87-92.

Wulff, H. et al. 2007 "Targeting effector memory T-cells with Kv1.3 blockers" *Current Opinion in Drug Discovery & Development* 10(4):438-445.

Aiyar, J. et al. 1996 "The Signature Sequence of Voltage-gated Potassium Channels Projects into the External Vestibule" *The Journal of Biological Chemistry* 271: 31013-31016.

Basabe, Pilar et al. 2008 "Synthesis of isoprenyl flavonoids: (+)-denticulaflavonol, Macarangin, and Isomacarangin" *SYNLRTT* 8: 1149-1152.

Beeton, C. et al. 2001 "Selective blockade of T lymphocyte $K^+$ channels ameliorates experimental autoimmune encephalomyelitis, a model for multiple sclerosis" *PNAS* 98: 13942-13947.

Beeton, C. et al. 2005 "Targeting Effector Memory T Cells with a Selective Peptide Inhibitor of Kv1.3 Channels for Therapy of Autoimmune Diseases" *Molecular Pharmacology* 67: 1369-1381.

Bhaskar A. & Seshadri, T.R. 1974 "Syntheses of Pashanone & Its Isomers & Their Derivatives" *Indian Journal of Chemistry* 12: 557-560.

Cahalan, M. D. et al. 1985 "A Voltage-Gated Potassium Channel in Human T Lymphocytes" *J. Physiol.* 358: 197-237.

Cahalan, M. D. & Chandy, K.G. 1997 "Ion channels in the immune system as targets for immunosuppression" *Current Opinion in Biotechnology* 8: 749-756.

Elix, J. A. et al. 1998 "Synthesis of New Lichen Tridepsides" *Australian Journal of Chemistry* 51: 1045-1052.

Fanger, C.M. et al. 1999 "Calmodulin Mediates Calcium-dependent Activation of the Intermediate Conductance $K_{Ca}$ Channel, *IKCa1*" *The Journal of Biological Chemistry* 274: 5746-5754.

Fuchs, P. et al. 2002 "A Thermotropic Mesophase Comprised of Closed Micellar Aggregates of the Normal Type**" *Angew. Chem. Int. Ed.* 41: 628-631.

Ghanshani, S. et al. 1998 "Human Calcium-Activated Potassium Channel Gene *KCNN4* Maps to Chromosome 19q13.2 in the Region Deleted in Diamond-Blackfan Anemia" *Genomics* 51: 160-161.

Grissmer, S. et al. 1990 "Expression and chromosomal localization of a lymphocyte $K^+$ channel gene" *Proc. Natl. Acad. Sci. USA* 87: 9411-9415.

Grissmer, S. et al. 1993 "Calcium-activated Potassium Channels in Resting and Activated Human T Lymphocytes *Expression Levels, Calcium Dependence, Ion Selectivity, and Pharmacology*" *The Journal of General Physiology* 102: 601-630.

Gunzinger, J. & Tabacchi, R. 1985 "Synthesis of a New Depsidone, Derivative of Furfuric Acid: Methyl 3,8-Dimethoxy-9-(2,4-dimethoxy-5-methoxycarbonyl-3,6-dimethylbenzyl)-1,4,6-trimethy-11-oxo-11H dibenzo[b,e][ 1,4Idioxepin-7-carboxylate" *Helvetica Chimica Acta* 68: 1940-1947.

Hatakeda, K. et al. 1977 "Synthesis of 2-Alkoxy-3, 4, 6-trihydroxyacetophenones" *Bulletin of the Chemical Society of Japan* 50: 1649-1650.

Horie, T. et al. 1983 "Studies of the Selective *O*-Alkylation and Dealkylation of Flavonoids. VI. Demethylation of 8-Hydroxy-5, 7-dimethoxyflavones with Anhydrous Aluminum Chloride or Bromide in Acetonitrile" *The Chemical Society of Japan* 56: 3773-3780.

Joiner, W.J. et al. 1997 "hSK4, a member of a novel subfamily of calcium-activated potassium channels" *Proc. Natl. Acad. Sci USA* 94: 11013-11018.

Khanna, R. et al. 1999 "hSK4/hIK1, a Calmodulin-binding $K_{Ca}$ Channel in Human T Lymphocytes *Roles in Proliferation and Volume Regulation*" *The Journal of Biological Chemistry* 274: 14838-14849.

Logsdon, N. J. et al. 1997 "A Novel Gene, *hKCa4*, Encodes the Calcium-activated Potassium Channel in Human T Lymphocytes" *The Journal of Biological Chemistry* 272: 32723-32726.

Rauer, H. et al. 1999 "Structural Conservation of the Pores of Calcium-activated and Voltage-gated Potassium Channels Determined by a Sea Anemone Toxin" *The Journal of Biological Chemistry* 274: 21885-21892.

Robertson, A. & Williamson, W.R.N. 1957 "Vitexin. Part II. The Synthesis of 3-Acetyl-2hydroxy-4: 6-dimethoxyphenylacetaldehyde Dimethyl Acetal" *Journal of the Chemical Society* 5018-5019.

Schmalhofer, W.A. et al. 2002 "Identification of a New Class of Inhibitor of the Voltage-Gated Potassium Channel, Kv1.3, with Immunosuppressant Properties" *Biochemistry* 41: 7781-7794.

Schmalhofer, W.A. et al. 2003 "Di-Substituted Cyclohexyl Derivatives Bind to two Identical Sites with Positive Cooperativity on the Voltage-Gated Potassium Channel, Kv1.3" *Biochemistry* 42: 47334743.

Schmitz, A. et al. 2005 "Design of PAP-1, a Selective Small Molecule Kv1.3 Blocker, for the Suppression of Effector Memory T Cells in Autoimmune Diseases" *Molecular Pharmacology* 68: 1254-1270.

Vandorpe. D.H. et al. 1998 "cDNA Cloning and Functional Characterization of the Mouse $Ca^{2+}$-gated $K^+$ Channel, mIK1" *The Journal of Biological Chemistry* 273: 21542-21553.

Vennekamp, J. et al. 2004 "Kv1.3-Blocking 5-Phenylalkoxypsoralens: A New Class of Immunomodulators" *Molecular Pharmacology* 65: 1364-1374.

Verheugen, J.A.H. et al. 1995 "Voltage-gated and $Ca^{2+}$-activated $K^+$ channels in Intact Human T lymphocytes; Noninvasive Measurements of Membrane Current, Membrane Potential, and Intracellular Calcium" *J. Gen. Physiol.* 105: 765-794.

Whitelaw, M.L. et al. 1991 "Synthesis and sensory evaluation of ring-substituted dihydrochalcone sweeteners. 2. Analogues of 3'-carboxyhesperetin dihydrochalcone, a high-potency dihydrochalcone sweetener" *J Agric Chem* 39: 663-667.

Wulff, H. et al. 2003 "Potassium channels as therapeutic targets for autoimmune disorders" *Current Opinion in Drug Discovery & Development* 6: 640-647.

Wulff, H. et al. 2003 "The voltage-gated Kv1.3 K+ channel in effector memory T cells as new target for MS" *The Journal of Clinical Investigation* 111: 1703-1713. (Erratum attached).

Xu, Jianchao et al. 2004 "The voltage-gated potassium channel Kv1.3 regulates peripheral insulin sensitivity" *PNAS* 101: 3112-3117.

\* cited by examiner

ARYL POTASSIUM CHANNEL BLOCKERS AND USES THEREOF

RELATED APPLICATIONS

This application is a U.S. National Phase of International Application No.: PCT/AU2008/001480, filed Oct. 3, 2008, designating the U.S. and published in English on Apr. 9, 2009 as WO 2009/043117, which claims the benefit of U.S. Provisional Application No. 60/977,538, filed Oct. 4, 2007.

FIELD OF THE INVENTION

The present invention relates to compounds useful in the modulation of potassium channel activity in cells, in particular the activity of Kv1.3 channels found in T cells. The invention also relates to the use of these compounds in the treatment or prevention of autoimmune and inflammatory diseases, including multiple sclerosis, pharmaceutical compositions containing these compounds and methods for their preparation.

BACKGROUND

Many autoimmune and chronic inflammatory diseases are related to immunoregulatory abnormalities. Diseases such as systemic lupus erythematosis, chronic rheumatoid arthritis, multiple sclerosis and psoriasis have in common the appearance of autoantibodies and self-reactive lymphocytes.

Multiple sclerosis is the most common neurological disease of young people. It is believed to cost more in medical care and lost income than any other neurological disease of young adults.

Multiple sclerosis affects the myelin sheaths of nerves. Myelin is an insulating material that coats most axons and allows rapid signal conduction over long distances by saltatory conduction. It is thought that antibodies and specialised cells of the immune system attack the myelin coating. This process leads to inflammation and scarring (sclerosis) which damages blood vessels in the area by the formation of a lesion known as a plaque. These plaques are characterised by being infiltrated by macrophages and T cells. This results in demyelination with the consequential loss of the rapid signal conduction.

A possible method of treating these autoimmune and inflammatory diseases is by suppressing T-cell proliferation and modulating their activation.

The early stages of T-cell activation may be conceptually separated into pre-$Ca^{2+}$ and post-$Ca^{2+}$ events (Cahalan and Chandy 1997, *Curr. Opin. Biotechnol.* 8 749). Following engagement of the T-cell receptor by an antigen, activation of tyrosine kinases and the generation of inositol 1,4,5-triphosphate lead to the influx of $Ca^{2+}$ and a rise in the cytoplasmic $Ca^{2+}$ concentration. The rise in $Ca^{2+}$ activates the phosphatase calcineurin, which then dephosphorylates a cytoplasmically localized transcription factor (N-FAT) enabling it to accumulate in the nucleus and bind to a promoter element of the interleukin-2 gene. Along with parallel events involving the activation of protein kinase C and ras, gene transcription leads to lymphokine secretion and to lymphocyte proliferation. Some genes require long-lasting $Ca^{2+}$ signals while others require only a transient rise of $Ca^{2+}$.

Ion channels underlie the $Ca^{2+}$ signal of T-lymphocytes. $Ca^{2+}$ ions move across the plasma membrane through a channel termed the store-operated $Ca^{2+}$ channel or the calcium release-activated $Ca^{2+}$ channel. Two distinct types of potassium channels indirectly determine the driving force of calcium entry. The first is the voltage-gated Kv1.3 channel (Cahalan 1985, *J. Physiol.* 385: 197; Grissmer 1990, *Proc. Natl. Acad. Sci. USA* 87 9411; Verheugen 1995, *J. Gen. Physiol.* 105 765; Aiyar 1996, *J. Biol. Chem.* 271 31013; Cahalan and Chandy 1997, *Curr. Opin. Biotechnol.* 8 749) and the second is the intermediate-conductance calcium-activated potassium channel, IKCa1 (Grissmer 1993, *J. Gen. Physiol.* 102 601; Fanger 1999 *J. Biol. Chem.* 274 5746; Rauer 1999, *J. Biol. Chem.* 274 21885; VanDorpe 1998, *J. Biol. Chem.* 273 21542; Joiner 1997, *Proc. Natl. Acad. Sci. USA* 94 11013; Khanna 1999, *J. Biol. Chem.* 274 14838; Lodgson 1997, *J. Biol. Chem.* 272 32723; Ghanshani 1998, *Genomics* 51 160). When these potassium channels open, the resulting efflux of $K^+$ hyperpolarizes the membrane, which in turn accentuates the entry of $Ca^{2+}$, which is absolutely required for downstream activation events (Cahalan and Chandy 1997, *Curr. Opin. Biotechnol.* 8: 749).

The predominant voltage-gated channel in human T-lymphocytes is encoded by Kv1.3, a Shaker-related gene. Kv1.3 has been characterised extensively at the molecular and physiological level and plays a vital role in controlling T-lymphocyte proliferation, mainly by maintaining the resting membrane potential of resting T-lymphocytes. Inhibition of this channel depolarises the cell membrane sufficiently to decrease the influx of $Ca^{2+}$ and thereby prevents downstream activation events.

Accordingly, compounds which are selective Kv1.3 blockers are potential therapeutic agents as immunosuppressants for the prevention of graft rejection, and the treatment of autoimmune and inflammatory disorders. They could be used alone or in conjunction with other immunosuppressants, such as selective IKCa1 blockers or cyclosporin, in order to achieve synergism and/or to reduce toxicity, especially of cyclosporin.

Developments in the field of voltage-gated K-channel electrophysiology have strengthened the case for treating of multiple sclerosis and also diabetes mellitus by inhibiting the Kv1.3 channel. It was found that autoreactive T-cells from multiple sclerosis patients exhibit highly elevated levels of Kv1.3 (Wulff, H et al (2003) J. Clin Invest. 111 (11) 1703-1713). ShK-K22Dap, a selective peptide blocker of Kv1.3, potently inhibited the proliferation of T-cells with this high-Kv1.3 phenotype. (Beeton, C. et al (2001) PNAS 98 13942-13947). The connection between T-cell replication and Kv1.3 blockade has also been shown through the use of a small molecule, a psoralen derivative, that is an active and relatively specific inhibitor of the Kv1.3 channel. The derivative showed specificity in inhibiting the proliferation of the high Kv1.3 T-cells over peripheral blood T-cells (Vennekamp et al (2004) Mol. Pharm. 65 1364-1374).

The Kv1.3 channel has also been associated with diabetes. Studies of Kv1.3 knockout mice found that the mice have increased insulin sensitivity. The selective blockage of the Kv1.3 channel also led to increased insulin sensitivity (Xu, J. et al. (2004) *PNAS* 101 (9), 3122-3117). It has been suggested by Wulff, who was involved in the electrophysiology on multiple sclerosis that diabetes also involves autoreactive T-cells that express very high levels of Kv1.3 (Wulff, H. et al. (2003) *Curr. Op. DDD.* 6 640-647).

At present there exist a number of non-selective potassium channel blockers that will inhibit lymphocyte proliferation, but have adverse side effects. Other potassium channels exist in a wide range of tissues including the heart and brain, and generally blocking these channels is undesirable. Accordingly it would be advantageous to provide or identify compounds, which are selective inhibitors of the Kv1.3 channel.

U.S. Pat. No. 5,494,895 discloses the use of a thirty-nine amino acid peptide, scorpion peptide margatoxin, as a selective inhibitor and probe of Kv1.3 channels present in human lymphocytes, and also as an immunosuppressant. However the use of this compound is limited by its potent toxicity.

International Patent Application publication No's WO 97/16438 and WO 09/716,437, and U.S. Pat. No. 6,051,590 describe the use of the triterpene, correolide and related compounds as immunosuppressants. The potential for these compounds to become immunosuppressants was illustrated by experiments showing their attenuation of the delayed-type hypersensitivity (DTH) response in mini-swine.

U.S. Pat. No. 6,077,680 describes DNA segments and proteins derived from sea anemone species, more particularly ShK toxin from *Stichodactyla helianthus*. The ShK toxin was found to block Kv1.1, Kv1.3, Kv1.4 and Kv1.6, but a mutant ShK-K22DAP was found to selectively block Kv1.3. Unfortunately the mutant did not exhibit the requisite pharmacokinetic profile for clinical use. A recently reported ShK analog, ShK(L5), was at least 100-fold more active against Kv1.3 ($K_d$=69 pM) than Kv1.1 and furthermore it showed at least 250-fold selectivity over every other relevant member of the Kv1 family (Beeton et al. (2005) *Mol. Pharm.* 67:1369-1381).

Both ShK toxin and ShK(L5) were shown to both prevent and treat experimental autoimmune encephalomyelitis in Lewis rats, an animal model for human multiple sclerosis (Beeton, et al. (2001) *Proc. Natl. Acad. Sci. USA* 98 13942), by selectively targeting T-cells chronically activated by the myelin antigen, MBP (myelin basic protein). The same study also indicated that chronically activated encephalitogenic rat T-cells express a unique channel phenotype characterised by high expression of Kv1.3 channels (approximately 1500 per cell) and low numbers of IKCa1 channels (approximately 120 per cell). This channel phenotype is distinct from that seen in quiescent and acutely activated cells and may be a functionally relevant marker for chronically activated rat T lymphocytes.

Other compounds which are blockers of Kv1.3 include psoralens (Vennekamp et al. (2004) *Mol. Pharm.* 65, 1365-1374 and Wulff at al., US 2006/0079535) and selected benzamides (Schalhofer et al. (2002) *Biochem.* 41, 7781-7794 and Schalhofer et al (2003) *Biochem.* 42, 4733-4743). The reported compounds in these classes did not exhibit drug-like characteristics.

Khellinone, a substituted benzofuran and natural product from certain plants, and 8-Methoxypsoralen (8-MOP), both commercially available products, have been found to exhibit weak blocking activity on the Kv1.3 channel.

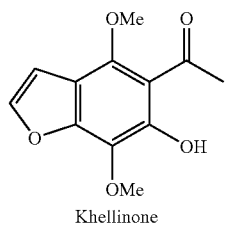

Khellinone

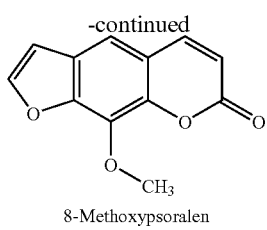

8-Methoxypsoralen

The present invention is directed to a new class of compounds which exhibit useful Kv1.3 channel blocking activity.

SUMMARY OF THE INVENTION

The invention provides compounds of formula (I) or salts thereof:

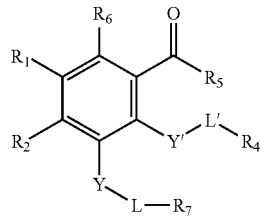

wherein
$R_1$ and $R_2$ are independently selected from hydrogen, cyano, halo, nitro, optionally substituted lower alkyl, optionally substituted aryl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl), and
wherein at least one of $R_1$ and $R_2$ is other than hydrogen;
$R_6$ is selected from cyano, halo, nitro, optionally substituted alkyl, optionally substituted alkenyl, optionally substituted alkynyl, optionally substituted aryl, optionally substituted heteroaryl, optionally substituted $C_{3-7}$ cycloalkyl, optionally substituted $C_{4-7}$ cycloalkenyl, —OR, —SR, —C(O)R, —C(O)OR, —OC(O)R (where R is selected from hydrogen, lower alkyl, lower alkenyl, lower alkynyl, optionally substituted $C_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl);
L is a divalent linker group of 2-6 atoms in length selected from optionally substituted $C_{2-6}$ alkylene, optionally substituted $C_{2-6}$ alkenylene, or optionally substituted $C_{2-6}$ alkynylene;
L' is (i) a divalent linker group of 2-6 atoms in length selected from optionally substituted $C_{2-6}$ alkylene, optionally substituted $C_{2-6}$ alkenylene, or optionally substituted $C_{2-6}$ alkynylene; or
(ii) —CH$_2$—;
Y is selected from a single bond, —O—, —C(O)—, —S—, —NR'''—, —C(O)NR'''—, or —NR'''C(O)— (where R''' is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl);

Y' is selected from a single bond, —O—, —C(O)—, —S—, —NR'''—, —C(O)NR'''—, or —NR'''C(O)— (where R''' is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl);

$R_5$ is selected from optionally substituted alkyl, —OR, —C(O)R, —C(O)OR, SR, (where R is selected from optionally substituted $C_{2-7}$ alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R'', —NR'C(O)R'' and —NR'R'' (where R' and R'' are independently selected from hydrogen or lower alkyl);

$R_4$ is selected from substituted aryl, substituted aryloxy, optionally substituted heteroaryl, optionally substituted heteroaryloxy, optionally substituted heterocyclyl, optionally substituted heterocyclyloxy or —NR'''R'''' (where R''' is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl, and where R'''' is selected from optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl); and $R_7$ is selected from optionally substituted aryl, optionally substituted aryloxy, optionally substituted heteroaryl, optionally substituted heteroaryloxy, optionally substituted heterocyclyl, optionally substituted heterocyclyloxy or —NHR''' (where R''' is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl).

In another aspect of the invention there is provided a method for the treatment or prevention of autoimmune or chronic inflammatory diseases, or the prevention of rejection of foreign organ transplants and/or related afflictions, by the administration of a compound of formula I or a pharmaceutically acceptable salt thereof, or a composition containing a compound of formula I or pharmaceutically acceptable salt thereof.

In another aspect the invention provides the use of a compound of formula I or a salt thereof in the manufacture of a medicament for the treatment or prevention of autoimmune or chronic inflammatory diseases, or the prevention of rejection of foreign organ transplants and/or related afflictions.

In another aspect of the invention there is provided a method of intentionally modulating potassium ion channel activity of T-cells by the application of a compound of Formula I, or a pharmaceutically acceptable salt thereof, to said T-cells.

In a further aspect of the invention there is provided a pharmaceutical composition for use as an immunosuppressant, the composition comprising an effective amount of a compound of Formula I or pharmaceutically acceptable salt thereof and optionally a carrier or diluent.

In another aspect of the invention there is provided a process for the preparation of compounds of formula I or salts thereof.

DETAILED DESCRIPTION OF THE INVENTION

The invention is based on the discovery that compounds of the general formula I, as described in the above Summary of the Invention can have useful properties as inhibitors of potassium cell channels, and particularly the Kv1.3 channel. Such compounds have significant potential as immunosuppressants for the treatment of autoimmune disorders such as multiple sclerosis and rheumatoid arthritis. They may also be useful in the treatment or prevention of graft rejection.

The term "alkyl" as used alone or in combination herein refers to a straight or branched chain saturated hydrocarbon group. The term "$C_{1-12}$ alkyl" refers to such a group containing from one to twelve carbon atoms and the terms "$C_{1-6}$ alkyl" and "lower alkyl" refer to such groups containing from one to six carbon atoms, such as methyl ("Me"), ethyl ("Et"), n-propyl, isopropyl, n-butyl, isobutyl, sec-butyl, tert-butyl and the like.

The term "alkylene" refers to divalent alkyl groups preferably having from 1 to 10 carbon atoms and more preferably 1 to 6 carbon atoms. Examples of such alkylene groups include methylene (—CH$_2$—), ethylene (—CH$_2$CH$_2$—), and the propylene isomers (e.g., —CH$_2$CH$_2$CH$_2$— and —CH(CH$_3$)CH$_2$—), and the like.

The term "$C_{3-7}$ cycloalkyl" refers to non-aromatic, saturated non-aromatic carbocycles having from 3 to 7 carbon atoms. Examples include cyclopropyl, cyclopentyl and cyclohexyl.

The term "alkenyl" refers to a straight or branched hydrocarbon containing one or more double bonds, preferably one or two double bonds. The term "$C_{2-12}$ alkenyl" refers to such a group containing from two to twelve carbon atoms. Examples of alkenyl include allyl, 1-methylvinyl, butenyl, iso-butenyl, 1,3-butadienyl, 3-methyl-2-butenyl, 1,3-butadienyl, 1,4-pentadienyl, 1-pentenyl, 1-hexenyl, 3-hexenyl, 1,3-hexadienyl, 1,4-hexadienyl and 1,3,5-hexatrienyl.

The term "alkenylene" refers to divalent alkenyl groups preferably having from 2 to 8 carbon atoms and more preferably 2 to 6 carbon atoms. Examples include ethenylene (—CH═CH—), and the propenylene isomers (e.g., —CH$_2$CH═CH— and —C(CH$_3$)═CH—), and the like.

The term "$C_{4-7}$ cycloalkenyl" refers to non aromatic carbocycles having 4 to 7 carbon atoms and having one or more double bonds. Examples include cyclopentenyl, 1-methyl-cyclopentenyl, cyclohexenyl, 1,3-cyclopentadienyl, 1,3-cyclohexadienyl and 1,4-cyclohexadienyl.

The term "alkynyl" refers to a straight or branched hydrocarbon containing one or more triple bonds, preferably one or two triple bonds. The term "$C_{2-12}$ alkynyl" refers to such a group containing from two to twelve carbon atoms. Examples include 2-propynyl and 2- or 3-butynyl.

The term "alkynylene" refers to the divalent alkynyl groups preferably having from 2 to 8 carbon atoms and more preferably 2 to 6 carbon atoms. Examples include ethynylene (—C≡C—), propynylene (—CH$_2$—C≡C—), and the like.

The term "alkoxy" as used alone or in combination refers to a straight or branched chain alkyl group covalently bound via an oxygen linkage (—O—) and the terms "$C_{1-6}$ alkoxy" and "lower alkoxy" refer to such groups containing from one to six carbon atoms, such as methoxy, ethoxy, propoxy, isopropoxy, butoxy, t-butoxy and the like.

The terms "alkenyloxy" and "alkynyloxy" as used alone or in combination respectively refer to an alkenyl and alkynyl group as earlier described linked via an oxygen linkage (—O—).

The term "aromatic" when used alone or in combination refers to monocyclic or bicyclic aryl rings and ring systems (aromatic hydrocarbon rings or ring systems) and also aromatic heterocyclic rings or ring systems, as known as heteroaryl or heteroaromatic rings. Preferred aromatic rings are optionally substituted phenyl ("Ph") rings.

The term "aryl" refers to carbocyclic (non-heterocyclic) aromatic rings or ring systems. The aromatic rings may be mono- or bi-cyclic ring systems. The aromatic rings or ring systems are generally composed of 5 to 10 carbon atoms. Examples of suitable aryl groups include but are not limited to phenyl, biphenyl, naphthyl, tetrahydronaphthyl, and the like.

Preferred aryl groups include phenyl, naphthyl, indenyl, azulenyl, fluorenyl or anthracenyl.

The term "heteroaryl" refers to a monovalent aromatic carbocyclic group, preferably of from 2 to 10 carbon atoms and 1 to 4 heteroatoms selected from oxygen, nitrogen and sulfur within the ring. Preferably the heteroatom is nitrogen. Such heteroaryl groups can have a single ring (e.g., pyridyl, pyrrolyl or furyl) or multiple condensed rings (e.g., indolizinyl or benzothienyl).

The term "heterocyclyl" refers to a monovalent saturated or unsaturated group having a single ring or multiple condensed rings, preferably from 1 to 8 carbon atoms and from 1 to 4 hetero atoms selected from nitrogen, sulfur, oxygen, selenium or phosphorous within the ring.

Examples of 5-membered monocyclic heterocyclyl and heteroaryl groups include furyl, thienyl, pyrrolyl, H-pyrrolyl, pyrrolinyl, pyrrolidinyl, oxazolyl, oxadiazolyl, (including 1, 2, 3 and 1, 2, 4 oxadiazolyls) thiazolyl, isoxazolyl, furazanyl, isothiazolyl, pyrazolyl, pyrazolinyl, pyrazolidinyl, imidazolyl, imidazolinyl, triazolyl (including 1, 2, 3 and 1,3,4 triazolyls), tetrazolyl, thiadiazolyl (including 1, 2, 3 and 1,3,4 thiadiazolyls).

Examples of 6-membered monocyclic heterocyclyl and heteroaryl groups include pyridyl, pyrimidinyl, pyridazinyl, pyranyl, pyrazinyl, piperidinyl, 1,4-dioxanyl, morpholinyl, 1,4-dithianyl, thiomorpholinyl, piperazinyl, 1,3,5-trithianyl and triazinyl.

The above heterocycles may be optionally substituted with a broad range of substituents, such as $C_{1-6}$ alkyl, $C_{1-6}$ alkoxy, $C_{2-6}$ alkenyl, $C_{2-6}$ alkynyl, halo, hydroxy, mercapto, trifluoromethyl, phenyl, phenyloxy, phenylalkyl, phenylalkyloxy, amino, cyano or mono or di($C_{1-6}$alkyl)amino.

As referred to above heterocycle or heteroaryl may be fused to a carbocyclic ring such as phenyl, naphthyl, indenyl, azulenyl, fluorenyl and anthracenyl.

Examples of 8, 9 and 10-membered bicyclic heterocyclyl and heteroaryl groups include 1H thieno[2,3-c]pyrazolyl, thieno[2,3-b]furyl, indolyl, isoindolyl, benzofuranyl, benzothienyl, benzoxazolyl, benzothiazolyl, benzisoxazolyl, benzisothiazolyl, benzimidazolyl, indazolyl, isoquinolinyl, quinolinyl, quinoxalinyl, uridinyl, purinyl, cinnolinyl, phthalazinyl, quinazolinyl, quinoxalinyl, benzotriazinyl, naphthyridinyl, pteridinyl and the like. These heterocycles may be optionally substituted, for example with $C_{1-6}$alkyl, $C_{1-6}$alkoxy, $C_{2-6}$alkenyl, $C_{2-6}$alkynyl, halo, hydroxy, mercapto, trifluoromethyl, cyano, phenyl, phenyloxy, phenylalkyl, phenylalkyloxy, amino and mono or di($C_{1-6}$alkyl) amino.

Examples of some heterocyclic and heteroaromatic radicals include (optionally substituted) isoxazoles, isothiazoles, 1,3,4-oxadiazoles, 1,3,4-thiadiazoles, 1,2,4-oxadiazoles, 1,2,4-thiadiazoles, oxazoles, thiazoles, pyridines, pyridazines, pyrimidines, pyrazines, 1,2,4-triazines, 1,3,5-triazines, benzoxazoles, benzothiazoles, benzisoxazoles, benzisothiazoles, quinolines, quinoxalines, furyl, thienyl, pyridyl, pyrrolyl, oxazolyl, thiazolyl, imidazolyl, pyrazolyl, isoxazolyl, isothiazolyl, 1,2,3-oxadiazolyl, 1,2,4-oxadiazolyl, 1,2,4-oxadiazol-5-one, 1,2,3-triazolyl, 1,3,4-thiadiazolyl, pyridazinyl, pyrimidinyl, pyrazinyl, 1,3,5-triazinyl, 1H thieno[2,3-c]pyrazolyl, thieno[2,3-b]furyl, indolizinyl, indolyl, isoindolyl, 3H-indolyl, indolinyl, benzo[b]furanyl, benzo[b]thiophenyl, 1H-indazolyl, benzimidazolyl, tetrazolyl, uridinyl, and cytosinyl. These radicals can be optionally substituted with, by example, $C_{1-6}$alkyl, $C_{1-6}$alkoxy, $C_{2-6}$alkenyl, $C_{2-6}$alkynyl, halo, hydroxy, mercapto, trifluoromethyl, amino, phenyl, phenyloxy, phenylalkyl, phenylalkyloxy, cyano or mono or di($C_{1-6}$alkyl)amino.

Heteroaryl or heteroaromatic rings may preferably be selected from isoxazolyl, oxazolyl, imidazolyl, thiazolyl, thiadiazolyl, isothiazolyl, furazanyl, triazolyl, pyridyl, pyrimidinyl, furyl, pyrazolyl, pyridazinyl, thienyl and aryl fused heteroaromatic rings such as benzfuranyl, benzothiophenyl and benzoisoxazolyl.

Heterocyclyl or heterocyclic rings may preferably be selected from pyrrolidine, imidazoline, 2-imidazolidone, 2-pyrrolidone, pyrrolin-2-one, tetrahydrofuran, 1,3-dioxolane, piperidine, tetrahydropyran, oxazoline, 1,3-dioxane, 1,4-piperazine, morpholine and thiomorpholine.

The term "arylalkyl" refers to carbocyclic aromatic rings or ring systems as previously described and substituted by an alkyl group, also as previously described. Unless otherwise indicated the aryl substituent is attached by the alkyl part of the substituent. Likewise the terms "aryl $C_{1-12}$ alkyl", "aryl $C_{2-12}$ alkenyl" and "aryl $C_{2-12}$ alkynyl" refer to carbocyclic aromatic rings or ring systems as previously described and substituted by a $C_{1-12}$ alkyl, $C_{2-12}$ alkenyl or $C_{2-12}$ alkynyl group, as previously described.

The terms "halo" and "halogen" refers to fluoro, chloro, bromo and iodo groups.

The term "aryloxy" refers to an aryl group as earlier described linked to the parent structure via an oxygen linkage (—O—). A notable example is phenoxy. Similarly the term "heteroaryloxy" refers to a heteroaryl group as earlier described linked to the parent structure via an oxygen group. A notable example is a 4, 6 or 7-benzo[b]furanyloxy group.

The term "optionally substituted" means that a group may include one or more substituents. One or more hydrogen atoms on the group may be replaced by substituent groups independently selected from halogens (for example halo alkyl such as —$CF_3$), $C_{1-6}$ alkyl, $C_{2-6}$ alkenyl, $C_{2-6}$ alkynyl, —$(CH_2)_pC_{3-7}$ cycloalkyl, —$(CH_2)_pC_{4-7}$ cycloalkenyl, —$(CH_2)_p$ aryl, —$(CH_2)_p$ heterocyclyl, —$(CH_2)_p$ heteroaryl, —$C_6H_4S(O)_qC_{1-6}$ alkyl, —C(Ph)$_3$, —CN, —OR, —O—$(CH_2)_{1-6}$—R, —O—$(CH_2)_{1-6}$—OR, —OC(O)R, —C(O)R, —C(O)OR, —OC(O)NR'R", —NR'R", —NRC(O)R', —NRC(O)NR'R", —NRC(S)NR'R", —NRS(O)$_2$R', —NRC(O)OR', —C(NR)NR'R", —C(=NOR')R, —C(=NOH)NR'R", —C(O)NR'R", —C(=NCN)—NR'R", —C(=NR)NR'R", —C(=NR')SR", —NR'C(=NCN)SR", —CONRSO$_2$R', —C(S)NR'R", —S(O)$_q$R, —SO$_2$NR'R", —SO$_2$NRC(O)R', —OS(O)$_2$R, —PO(OR)$_2$ and —NO$_2$; where p is 0-6, q is 0-2 and each R, R' and R" is independently selected from H, $C_{1-6}$ alkyl, $C_{2-6}$ alkenyl, $C_{2-6}$ alkynyl, $C_{3-7}$ cycloalkyl, $C_{4-7}$ cycloalkenyl, aryl, heterocyclyl, heteroaryl, $C_{1-6}$ alkylaryl, $C_{1-6}$ alkylheteroaryl, and $C_{1-6}$ alkylheterocyclyl, wherein the alkyl, alkenyl, alkynyl, cycloalkyl, cycloalkenyl, aryl, heterocyclyl, heteroaryl, $C_{1-6}$ alkylaryl, $C_{1-6}$ alkylheteroaryl, or $C_{1-6}$ alkylheterocyclyl, may be optionally substituted with one to six of same or different groups selected from halogen, hydroxy, lower alkyl, lower alkoxy, —CO$_2$H, CF$_3$, CN, phenyl, NH$_2$ and —NO$_2$; or when R' and R" are attached to the same nitrogen atom, they may, together with the atom to which they are attached, form a 5 to 7 membered nitrogen containing heterocyclic ring.

A list of preferred optional substituents includes halogens, $C_{1-6}$ alkyl, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, $C_{1-6}$ alkylcarbonyl, $C_{1-6}$ alkoxycarbonyl and $CO_2H$.

Unless otherwise defined and only in respect of the ring atoms of non-aromatic carbocyclic or heterocyclic compounds, the ring atoms of such compounds may also be optionally substituted with one or two =O groups, instead of or in addition to the above described optional substituents.

When the optional substituent is or contains an alkyl, alkenyl, alkynyl, cycloalkyl, cycloalkenyl, aryl, heteroaryl or heterocyclyl group, the group may itself be optionally substituted with one to six of the same or different substituents selected from halogens, $C_{1-6}$ alkyl, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, $C_{1-6}$ alkylcarbonyl, $C_{1-6}$ alkoxycarbonyl and $CO_2H$.

The salts of the compounds of formula I are preferably pharmaceutically acceptable, but it will be appreciated that non-pharmaceutically acceptable salts also fall within the scope of the present invention, since these are useful as intermediates in the preparation of pharmaceutically acceptable salts.

It will be appreciated that the compounds of formula I, and the salts thereof, can be presented in the form of pharmaceutically acceptable derivatives. The term "pharmaceutically acceptable derivative" includes pharmaceutically acceptable esters, prodrugs, solvates and hydrates of the compounds of formula I or salts thereof. Pharmaceutically acceptable derivatives may include any pharmaceutically acceptable hydrate or any other compound or prodrug which, upon administration to a subject, is capable of providing (directly or indirectly) a compound of formula I or an active metabolite or residue thereof.

The pharmaceutically acceptable salts include acid addition salts, base addition salts, and the salts of quaternary amines and pyridiniums. The acid addition salts are formed from a compound of the invention and a pharmaceutically acceptable inorganic or organic acid including but not limited to hydrochloric, hydrobromic, sulfuric, phosphoric, methanesulfonic, toluenesulphonic, benzenesulphonic, acetic, propionic, ascorbic, citric, malonic, fumaric, maleic, lactic, salicylic, sulfamic, or tartaric acids. The counter ion of quaternary amines and pyridiniums include chloride, bromide, iodide, sulfate, phosphate, methansulfonate, citrate, acetate, malonate, fumarate, sulfamate, and tartrate. The base addition salts include but are not limited to salts such as sodium, potassium, calcium, lithium, magnesium, ammonium and alkylammonium. Also, basic nitrogen-containing groups may be quaternised with such agents as lower alkyl halides, such as methyl, ethyl, propyl, and butyl chlorides, bromides and iodides; dialkyl sulfates like dimethyl and diethyl sulfate; and others. The salts may be made in a known manner, for example by treating the compound with an appropriate acid or base in the presence of a suitable solvent.

The compounds of the invention may be in crystalline form and/or as solvates (e.g. hydrates) and it is intended that both forms be within the scope of the present invention. The term "solvate" is a complex of variable stoichiometry formed by a solute (in this invention, a compound of the invention) and a solvent. Such solvents should not interfere with the biological activity of the solute. Solvents may be, by way of example, water, ethanol or acetic acid. Methods of solvation are generally known within the art.

The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester derivative or a ring nitrogen atom is converted to an N-oxide. Examples of ester derivatives include alkyl esters, phosphate esters and those formed from amino acids, preferably valine. Any compound that is a pro-drug of a compound of the invention is within the scope and spirit of the invention.

The term "pharmaceutically acceptable ester" includes biologically acceptable esters of compound of the invention such as sulphonic, phosphonic and carboxylic acid derivatives.

Thus, in another aspect of the invention, there is provided a prodrug or pharmaceutically acceptable ester of a compound of formula I of salt thereof.

It will be appreciated that the compounds of formula I and some derivatives thereof may have at least one asymmetric centre, and therefore are capable of existing in more than one stereoisomeric form. The invention extends to each of these forms individually and to mixtures thereof, including racemates. The isomers may be separated conventionally by chromatographic methods or using a resolving agent. Alternatively the individual isomers may be prepared by asymmetric synthesis using chiral intermediates. Where the compound has at least one carbon-carbon double bond, it may occur in Z- and E-forms with all isomeric forms of the compounds being included in the present invention.

In a preferred embodiment Y' is O.

Accordingly in a further preferred embodiment the present invention provides compounds of formula (Ia) or salts thereof,

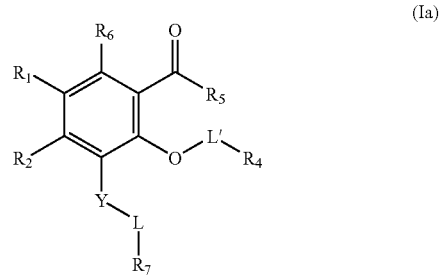

(Ia)

wherein $R_1$ and $R_2$ are independently selected from hydrogen, cyano, halo, nitro, optionally substituted lower alkyl, optionally substituted aryl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl), and wherein at least one of $R_1$ and $R_2$ is other than hydrogen;

$R_6$ is selected from cyano, halo, nitro, optionally substituted alkyl, optionally substituted alkenyl, optionally substituted alkynyl, optionally substituted aryl, optionally substituted heteroaryl, optionally substituted $C_{3-7}$ cycloalkyl, optionally substituted $C_{4-7}$ cycloalkenyl, —OR, —SR, —C(O)R, —C(O)OR, —OC(O)R (where R is selected from hydrogen, lower alkyl, lower alkenyl, lower alkynyl, optionally substituted $C_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl);

L is a divalent linker group of 2-6 atoms in length selected from optionally substituted $C_{2-6}$ alkylene, optionally substituted $C_{2-6}$ alkenylene, or optionally substituted $C_{2-6}$ alkynylene;

L' is a divalent linker group of 1-6 atoms in length selected from $C_{1-6}$ alkylene, $C_{2-6}$ alkenylene, or $C_{2-6}$ alkynylene;

Y is selected from single bond, —O—, —C(O)—, —S—, —NR'''—, —C(O)NR'''—, or —NR'''C(O)— (where R''' is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl);

$R_5$ is selected from optionally substituted alkyl, —OR, —C(O)R, —C(O)OR, SR, (where R is selected from optionally substituted $C_{2-7}$ alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl);

$R_4$ is selected from substituted aryl, substituted aryloxy, optionally substituted heteroaryl, optionally substituted heteroaryloxy, optionally substituted heterocyclyl, optionally substituted heterocyclyloxy or —NR'''R"" (where R''' is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl, and where R"" is selected from optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl); and $R_7$ is selected from optionally substituted aryl, optionally substituted aryloxy, optionally substituted heteroaryl, optionally substituted heteroaryloxy, optionally substituted heterocyclyl or optionally substituted heterocyclyloxy.

In a further embodiment Y' is O and L' is $C_{1-3}$ alkylene.

Accordingly in a further preferred embodiment the invention provides compounds of formula (Ib) or salts thereof:

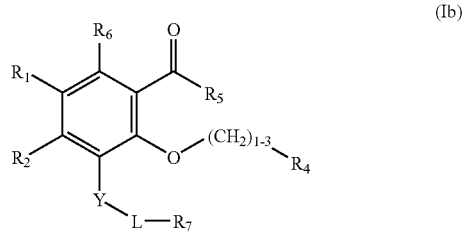

(Ib)

wherein $R_1$ and $R_2$ are independently selected from hydrogen, cyano, halo, nitro, optionally substituted lower alkyl, optionally substituted aryl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl), and wherein at least one of $R_1$ and $R_2$ is other than hydrogen;

$R_6$ is selected from cyano, halo, nitro, optionally substituted alkyl, optionally substituted alkenyl, optionally substituted alkynyl, optionally substituted aryl, optionally substituted heteroaryl, optionally substituted $C_{3-7}$ cycloalkyl, optionally substituted $C_{4-7}$ cycloalkenyl, —OR, —SR, —C(O)R, —C(O)OR, —OC(O)R (where R is selected from hydrogen, lower alkyl, lower alkenyl, lower alkynyl, optionally substituted $C_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl);

L is a divalent linker group of 2-6 atoms in length selected from optionally substituted $C_{2-6}$ alkylene, optionally substituted $C_{2-6}$ alkenylene, or optionally substituted $C_{2-6}$ alkynylene;

Y is selected from a single bond, —O—, —C(O)—, —S—, —NR'''—, —C(O)NR'''—, or —NR'''C(O)— (where R''' is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl);

$R_5$ is selected from optionally substituted alkyl, —OR, —C(O)R, —C(O)OR, SR, (where R is selected from optionally substituted $C_{2-7}$ alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl);

$R_4$ is selected from substituted aryl, substituted aryloxy, optionally substituted heteroaryl, optionally substituted heteroaryloxy, optionally substituted heterocyclyl, optionally substituted heterocyclyloxy or —NR'''R"" (where R''' is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl, and where R"" is selected from optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl); and $R_7$ is selected from optionally substituted aryl, optionally substituted aryloxy, optionally substituted heteroaryl, optionally substituted heteroaryloxy, optionally substituted heterocyclyl or optionally substituted heterocyclyloxy.

In some preferred embodiments of the invention, and with reference to the general formulae (I), (Ia) and (Ib), one or more of the following further preferred definitions apply:

a) $R_1$ and $R_2$ are independently selected from hydrogen, cyano, halo, optionally substituted lower alkyl, —OH, —O-optionally substituted lower alkyl, —C(O)-optionally substituted lower alkyl, and —C(O)NR'R" (wherein R' and R" are independently selected from hydrogen or lower alkyl), wherein at least one of $R_1$ and $R_2$ is other than hydrogen;

b) $R_1$ and $R_2$ are independently selected from cyano, halo, nitro, optionally substituted lower alkyl, optionally substituted aryl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl);

c) $R_1$ and $R_2$ are independently selected from cyano, halo, optionally substituted lower alkyl, —O-optionally substituted lower alkyl, —C(O)-optionally substituted lower alkyl, and —C(O)NR'R" (wherein R' and R" are independently selected from hydrogen or lower alkyl);

d) $R_4$ is selected from optionally substituted heteroaryl, optionally substituted heterocyclyl, optionally substituted heteroaryloxy, optionally substituted heterocyclyloxy, or —NR'''R"" (where R''' is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl, and where R"" is selected from optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl);

e) $R_7$ is selected from optionally substituted aryl, optionally substituted aryloxy, optionally substituted heteroaryl, optionally substituted heteroaryloxy, optionally substituted heterocyclyl, or optionally substituted heterocyclyloxy;

f) $R_5$ is an optionally substituted $C_{1-6}$ alkyl, for instance, methyl, ethyl and propyl, —OR, —SR (where R is selected from optionally substituted $C_{2-7}$ alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), and —NR'R" (where R' and R" are independently selected from hydrogen or lower alkyl);

g) $R_6$ is selected from cyano, halo, optionally substituted alkyl, optionally substituted alkenyl, optionally substituted alkynyl, optionally substituted heteroaryl, optionally substituted $C_{3-7}$ cycloalkyl, —O-optionally substituted lower alkyl, —O-optionally substituted $C_{3-7}$ cycloalkyl, or —O-optionally substituted heteroaryl;

h) L is a divalent linker group of 2-6 atoms in length selected from $C_{2-6}$ alkylene, $C_{2-6}$ alkenylene, or $C_{2-6}$ alkynylene, each of which may be optionally substituted by one or more of the following groups: halogen, $C_{1-6}$ alkyl, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, $C_{1-6}$ alkylcarbonyl, $C_{1-6}$ alkoxycarbonyl and $CO_2H$, preferably the optional substituent is a lower alkyl group (for instance methyl); and i) L' is a divalent linker group of 1-6 atoms in length selected from $C_{1-6}$ alkylene, $C_{2-6}$ alkenylene, or $C_{2-6}$ alkynylene, more preferably L' is a $C_{1-3}$ alkylene.

In other preferred embodiments of the invention and with reference to compounds of general formulae (I), (Ia), and (Ib), one or more of the following further preferred definitions may apply:

j) Y is a single bond or O;

k) L is optionally substituted $C_{1-4}$ alkylene wherein the optional substitutent is selected from halogen, $C_{1-6}$ alkyl, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, $C_{1-6}$ alkylcarbonyl, $C_{1-6}$ alkoxycarbonyl and $CO_2H$, preferably the optional substituent is a lower alkyl group (for instance methyl); and l) $R_4$ is selected from optionally substituted heteroaryl, optionally substituted heteroaryloxy, optionally substituted heterocyclyl, or —$NHC_{3-7}$ cycloalkyl;

m) $R_6$ is selected from halo, optionally substituted alkyl, or —O-optionally substituted alkyl;

n) $R_7$ is selected from optionally substituted aryl, more preferably optionally substituted phenyl; and o) $R_5$ is $C_{1-3}$ alkyl.

In even more preferred embodiments of the invention, and with reference to the above general formulae, one or more of the following further definitions apply:

p) $R_1$ is halo (even more preferably chloro) or lower alkyl (even more preferably methyl);

q) $R_2$ is $C_{1-3}$ alkoxy (even more preferably methoxy);

r) L is optionally substituted propylene or butylene (even more preferably —$CH_2$—$CH_2$—$CH(CH_3)$—, —$CH_2$—$CH_2$—$CH_2$—$CH_2$—, or —$CH_2$—$CH_2$—$CH_2$—);

s) L' is $C_{1-3}$ alkylene (even more preferably —$CH_2$—$CH_2$—);

t) $R_7$ is halo-substituted phenyl (even more preferably 4-fluorophenyl) or unsubstituted phenyl;

u) $R_5$ is methyl; and v) $R_6$ is $C_{1-3}$ alkyl (even more preferably methyl).

In relation to $R_4$ as described above for formulae (I), (Ia), and (Ib) preferred groups are as follows:

4-membered monocyclic heterocyclyls:
Azetidinyl;

5-membered monocyclic heterocyclyls:
pyrrolidinyl, pyrazolinyl, pyrazolidinyl, imidazolinyl, imidazolidinyl, pyrrolinyl (including 2 and 3 pyrrolinyls), dioxolane;

5-membered monocyclic heteroaryls:
furyl, thienyl, pyrrolyl, H-pyrrolyl, oxazolyl, oxadiazolyl, (including 1, 2, 3 and 1, 2, 4 oxadiazolyls) thiazolyl, isoxazolyl, furazanyl, isothiazolyl, pyrazolyl, imidazolyl, triazolyl (including 1, 2, 3 and 1,3,4 triazolyls), tetrazolyl, and thiadiazolyl (including 1, 2, 3 and 1,3,4 thiadiazolyls);

6-membered monocyclic heteroaryls:
pyridyl, pyrimidinyl, pyridazinyl, pyrazinyl, and triazinyl;

6-membered monocyclic heterocyclyls:
Pyranyl (including 2H and 4H pyranyls), piperidinyl, morpholinyl, piperazinyl, 1,3,5-trithianyl, thiomorpholinyl, 1-oxo-thiomorpholinyl, 1,1-dioxothiomorpholinyl, 1,4-dithianyl, and 1,4-dioxanyl;

all of which may be optionally substituted with one or more groups selected from halogen, $C_{1-6}$ alkyl, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, $C_{1-6}$ alkylcarbonyl, $C_{1-6}$ alkoxycarbonyl and $CO_2H$.

Even more preferred $R_4$ groups include pyridyl, pyrazinyl, pyrazinyloxy, morpholinyl, piperidinyl, pyrrolidinyl, azetidinyl, and thiomorphinyl (and oxidised derivatives thereof) all of which may be optionally substituted with one or more groups selected from halogen, $C_{1-6}$ alkyl, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, $C_{1-6}$ alkylcarbonyl, $C_{1-6}$ alkoxycarbonyl and $CO_2H$.

The invention also includes where possible a salt or pharmaceutically acceptable derivative such as a pharmaceutically acceptable ester, solvate and/or prodrug of the above mentioned embodiments of the invention.

In another aspect of the invention, there is provided a pharmaceutical composition that comprises a therapeutically effective amount of one or more of the aforementioned compounds of Formulae (I), (Ia), and (Ib) or pharmaceutically acceptable salts thereof, including pharmaceutically acceptable derivatives thereof, and optionally a pharmaceutically acceptable carrier or diluent.

In another aspect, the present invention provides pharmaceutical compositions for use as a Kv1.3 ion channel blocker, more particularly as an immunosuppressant, the composition comprising an effective amount of a compound of Formula (I), (Ia), or (Ib) or a pharmaceutically acceptable salt thereof, including a pharmaceutically acceptable derivative thereof, and optionally a pharmaceutically acceptable carrier or diluent.

The term "composition" is intended to include the formulation of an active ingredient with encapsulating material as carrier, to give a capsule in which the active ingredient (with or without other carrier) is surrounded by carriers.

The pharmaceutical compositions or formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

The compounds of the invention, together with a conventional adjuvant, carrier, or diluent, may thus be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, in the form of suppositories for rectal administration; or in the form of sterile injectable solutions for parenteral (including subcutaneous) use.

Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed. Formulations containing ten (10) milligrams of active ingredient or, more broadly, 0.1 to one hundred (100) milligrams, per tablet, are accordingly suitable representative unit dosage forms.

The compounds of the present invention can be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, pharmaceutically acceptable carriers can be either solid or liquid. Solid form preparations include powders, tablets, pills, capsules, cachets, suppositories, and dispensable granules. A solid carrier can be one or more substances which may also act as diluents, flavouring agents, solubilisers, lubricants, suspending agents, binders, preservatives, tablet disintegrating agents, or an encapsulating material.

In powders, the carrier is a finely divided solid that is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized moulds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution.

Sterile liquid form compositions include sterile solutions, suspensions, emulsions, syrups and elixirs. The active ingredient can be dissolved or suspended in a pharmaceutically acceptable carrier, such as sterile water, sterile organic solvent or a mixture of both.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, eg. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavours, stabilisers, buffers, artificial and natural sweeteners, dispersants, thickeners, solubilising agents, and the like.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active agent in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multidose form. In the latter case of a dropper or pipette, this may be achieved by the patient administering an appropriate, predetermined volume of the solution or suspension. In the case of a spray, this may be achieved for example by means of a metering atomising spray pump. To improve nasal delivery and retention the compounds according to the invention may be encapsulated with cyclodextrins, or formulated with other agents expected to enhance delivery and retention in the nasal mucosa.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In formulations intended for administration to the respiratory tract, including intranasal formulations, the compound will generally have a small particle size for example of the order of 5 to 10 microns or less. Such a particle size may be obtained by means known in the art, for example by micronisation.

When desired, formulations adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The invention also includes the compounds in the absence of carrier where the compounds are in unit dosage form.

The amount of compound of Formulae (I), (Ia), and (Ib) administered may be in the range from about 10 mg to 2000 mg per day, depending on the activity of the compound and the disease to be treated.

Liquids or powders for intranasal administration, tablets or capsules for oral administration and liquids for intravenous administration are the preferred compositions.

The compositions may further contain one or more other immunosuppressants or other multiple sclerosis therapeutics. For example the compositions may contain a second immunosuppressive agent or other multiple sclerosis therapeutic such as interferon beta-1b, interferon beta-1a, glatiramer acetate, natalizumab or mitoxantrone.

The pharmaceutical preparations of the compounds according to the present invention may be co-administered with one or more other immunosuppressants or multiple sclerosis therapeutics in a combination therapy. For example the pharmaceutical preparation of the active compound may be co-administered (for example separately, concurrently or sequentially), with one or more other immunosuppressants or multiple sclerosis therapeutics, such as interferon beta-1b, interferon beta-1a, glatiramer acetate, natalizumab or mitoxantrone.

The compounds of the present invention may be useful in the therapeutic or prophylactic treatment of the resistance to transplantation of organs or tissue (such as heart, kidney, liver, lung, bone marrow, cornea, pancreas, intestinum tenue, limb, muscle, nervus, medulla ossium, duodenum, small-bowel, medulla ossium, skin, pancreatic islet-cell, etc. including xeno transplantation), graft-versus-host diseases; rheumatoid arthritis, systemic lupus erythematosus, nephrotic syndrome lupus, Palmo-planter pustulosis, Hashimoto's thyroiditis, multiple sclerosis, Guillain-Barre syndrome, myasthenia gravis, type I diabetes uveitis, juvenile-onset or recent-onset diabetes mellitus, diabetic neuropathy, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia greata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; pollen allergies, reversible obstructive airway disease, bronchial asthma, allergic asthma, intrinsic asthma, extrinsic asthma and dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene $B_4$-mediated diseases, Coeliac diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Meniere's disease, polyneuritis, multiple neuritis, mononeuritis, radiculopathy, hyperthyroidism, Basedow's disease, pure red cell aplasia, aplastic anaemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T-cell lymphoma, arteriosclerosis, atherosclerosis, aortitis syndrome, polyarteritis nodosa, myocardosis, scleroderma, Wegener's granuloma, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth; muscular dystrophy; Pyoderma and Sezary's syndrome, Sjoegren's syndrome, Addison's disease, ischemia-reperfusion injury of organs which occurs upon preservation, transplantation or ischemic disease, for example, thrombosis and cardiac infarction, endotoxin-shock, pseudomembranous colitis, colitis caused by drug or radiation, ischemic acute renal insufficiency, chronic renal insufficiency, toxinosis caused by lung-oxygen or drug, for example, paracort and bleomycins, lung cancer, pulmonary emphysema, cataracta, siderosis, retinitis, pigmentosa, senile macular degeneration, vitreal scarring, corneal alkali burn; dermatitis erythema multiforme, linear IgA ballous dermatitis and cement dermatitis, gingivitis, periodontitis, sepsis, pancreatitis, diseases caused by environmental pollution, aging, carcinogenis, metastasis of carcinoma and hypobaropathy; disease caused by histamine or leukotriene-$C_4$ release; Berger's disease, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, preventing or treating activity of cytomegalovirus infection, HCMV infection, and anti-inflammatory activity.

For certain of the abovementioned conditions it is clear that the compounds may be used prophylactically as well as for the alleviation of acute symptoms.

References herein to "treatment" or the like are to be understood to include such prophylactic treatment, as well as therapeutic treatments.

It is envisaged that the compounds may be particularly useful in the treatment of multiple sclerosis. This chronic neurological disorder affects the nerves of the central nervous system. As discussed earlier most nerves in the body are normally insulated by a protective sheath of fatty substance called myelin. Multiple sclerosis causes demyelination, in which this protective sheath becomes inflamed and ultimately destroyed.

By modulating or changing the immune system response that is thought to be responsible for the attack on the central nervous system it should be possible to attack the cause of the disease itself, rather than the more traditional method of controlling the symptoms.

The nature of the disease is such that it may be possible to control multiple sclerosis without unduly suppressing the patient's immune system. Based on the earlier discussed chronically activated human T-lymphocytes study, it is speculated that multiple sclerosis may be a product of chronically activated T-cells having a channel phenotype characterised by high expression of Kv1.3 channels and low numbers of IKCa1 channels. As this channel phenotype is distinct from that seen in quiescent and acutely activated cells it may provide a useful means for controlling multiple sclerosis without the significant side effects of less specific drugs.

In another aspect of the invention there is provided a method of preventing or treating autoimmune or chronic inflammatory diseases, the prevention of rejection of foreign organ transplants and/or related afflictions, said method including the step of administering a compound of Formula (I), (Ia), or (Ib), or salt thereof, or a composition comprising the compound or salt thereof.

Accordingly in a preferred form of the invention, there is provided a means for controlling multiple sclerosis by the application of a blocker of the Kv1.3 channel, preferably a selective channel blocker of the Kv1.3 channel, by the application of a compound of Formula (I), (Ia), or (Ib), or salt thereof, including a pharmaceutically acceptable derivative thereof, or a composition comprising the compound of Formula (I), (Ia), or (Ib), or salt thereof, or a pharmaceutically acceptable derivative thereof.

In another preferred form of the invention there is provided a method for preventing or treating diabetes including the step of administering a compound of Formula (I), (Ia), or (Ib), or a pharmaceutically acceptable salt thereof, including a pharmaceutically acceptable derivative thereof, or a composition comprising the compound or pharmaceutically acceptable salt thereof, or pharmaceutically acceptable derivative thereof.

In a further aspect, the invention provides a method of modulating potassium ion channel activity of T-cells by the application of a compound of Formula (I), (Ia), or (Ib), or a pharmaceutically acceptable salt thereof, including a pharmaceutically acceptable derivative thereof, or a composition comprising the same, to said T cells. Preferably the compounds of the invention inhibit the potassium ion channel activity of T-cells.

Preferably the potassium channel activity inhibited by a compound of Formula (I), (Ia), or (Ib) is a voltage-gated potassium channel, for example, Kv1.1-Kv1.7. More preferably the potassium ion channel activity is the voltage-gated potassium channel, Kv1.3 of a T-cell. Preferably the compound selectively inhibits the Kv1.3 channel.

In a further aspect of the present invention, there is provided the use of a compound of Formula (I), (Ia), or (Ib), or salt thereof, in the preparation of a medicament for the treatment (therapeutic or prophylactic) of disease states mediated by potassium channels, and in particular by blocking the Kv1.3 channel.

In a further aspect of the invention there is provided a process for the production of the compounds of Formula (I), (Ia), or (Ib), or salts thereof, including pharmaceutically acceptable derivatives thereof.

The compounds of the present invention may be prepared from substituted benzenes which are commercially available or obtained by standard electrophilic aromatic substitution or nucleophilic aromatic substitution chemistry. Examples of electrophilic aromatic substitution reactions include: halogenation (including bromination, chlorination, and iodination), nitration, sulfonation, Friedel-Crafts alkylation or acylation, reduction of aromatic nitro groups, and alkali fusion of aromatic sulfonates. Examples of nucleophilic aromatic substitution reactions include: substitution of halides, sulfonate esters or diazonium salts by amines, thiols, amide anions, sulphide anions or alkoxide anions. The substitution of halides, sulfonate esters or diazonium salts can also be accomplished under palladium mediated conditions to introduce various carbon and heteroatom based substituents. Other transformations include: oxidation of alkylbenzene alkyl side chains to form benzoic acids, reduction of aryl alkyl ketones, amination of unactivated aryl halides, and phenol formation from activated aryl halides.

From the appropriately substituted benzenes, comparator compounds may be prepared by the following scheme:

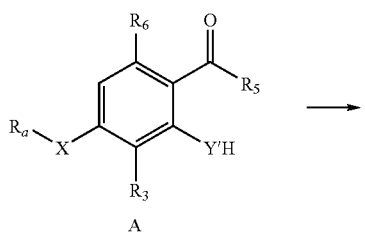

A

-continued

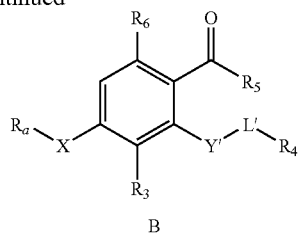

B

Compounds of the general structure B above may be prepared by reacting alkyl halides or carboxylic acids with compounds of the general structure A. Commercially available examples of compounds of formula A are shown in the table below.

| $R_a$ | X | Y | $R_3$ | $R_5$ | $R_6$ |
|---|---|---|---|---|---|
| Et | NH | O | Pr | Me | H |
| Ac | NH | O | H | Me | H |
| Ac | NH | O | H | Pr | H |
| H | NH | O | H | Me | H |
| Ac | NH | O | $CH_2$=$CH_2CH_2$ | Me | H |
| Me | O | N | H | Me | H |
| Me | O | N | H | Me | H |
| $MorphCH_2CH_2$ | O | O | H | Me | H |

Compounds of the present invention where $R_6$ is methyl, $R_1$ is alkyl or halo and $R_2$ is optionally substituted alkoxy may be prepared according to the following scheme which commences from general structure C:

The above scheme illustrates that the —$C(O)R_5$ group may be introduced to a pre-functionalised benzene ring by standard Friedel-Crafts chemistry with, for instance, acetyl chloride in presence of a suitable transition metal catalyst such as $TiCl_4$. The group $R_4'$ may represent a hydroxy protecting group such as methyl, which can be removed under standard demethylation conditions using, for instance, $BCl_3$. Subsequent introduction of a halide (Halo) by electrophilic halogenations and introduction of the -L'-$R_4$ (as described above for compound B) gives compounds D. Compounds D can be further transformed to compounds E by palladium mediated coupling to an alkyl-metal coupling partner (where metal=ZnCl, borane or zirconocene).

Alkylation of the substituted benzene prior to Friedel-Crafts acylation may be accomplished by initial electrophilic halogenations (not shown) followed by palladium mediated coupling to an alkyl-metal coupling partner (where metal=ZnCl, borane or zirconocene). Alternatively the initially formed halide (bromide or iodide) can be metallated (eg lithiated) and reacted with an alkyl halide.

In a further process comparator compounds where $R_2$ is $OR_6$ ($R_6$ may be alkyl), and $R_5$ is —$C(O)CH_2(O)OEt$ or —$C(O)CH_3$ may be prepared by the following scheme:

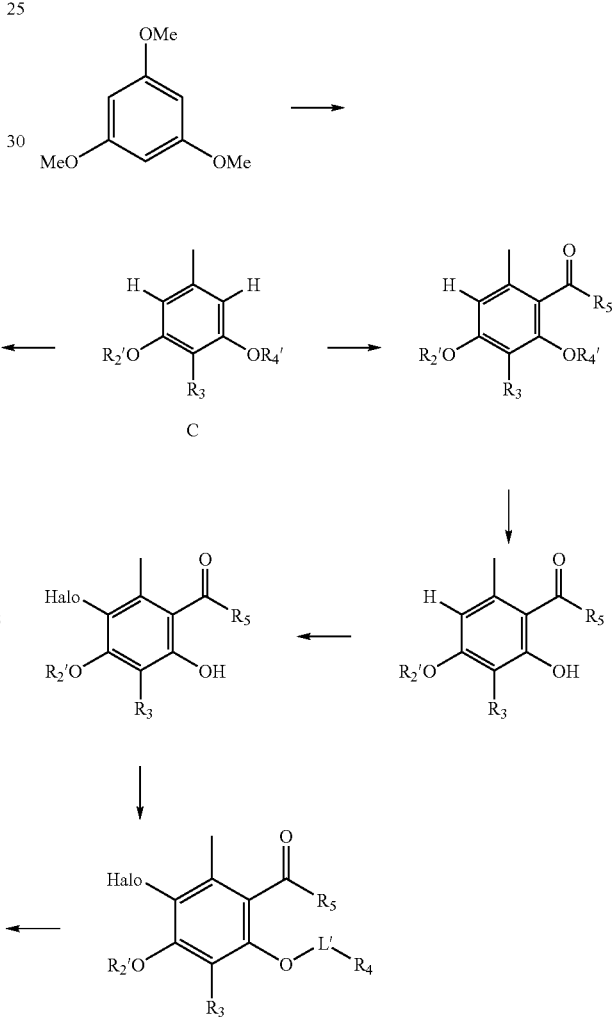

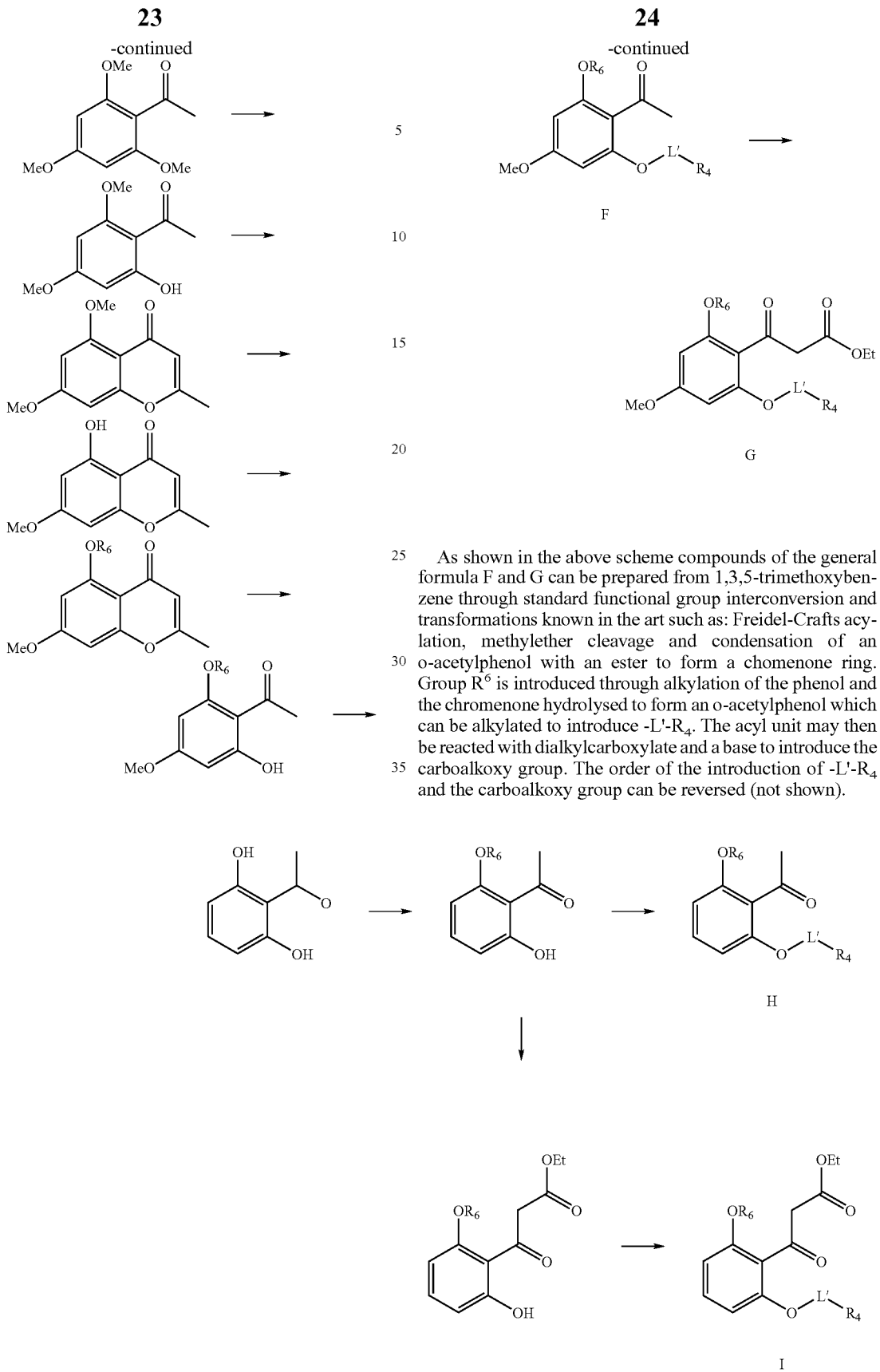

As shown in the above scheme compounds of the general formula F and G can be prepared from 1,3,5-trimethoxybenzene through standard functional group interconversion and transformations known in the art such as: Freidel-Crafts acylation, methylether cleavage and condensation of an o-acetylphenol with an ester to form a chomenone ring. Group $R^6$ is introduced through alkylation of the phenol and the chromenone hydrolysed to form an o-acetylphenol which can be alkylated to introduce -L'-$R_4$. The acyl unit may then be reacted with dialkylcarboxylate and a base to introduce the carboalkoxy group. The order of the introduction of -L'-$R_4$ and the carboalkoxy group can be reversed (not shown).

In the above scheme comparator compounds of the general formula H and I can be prepared from 2,6-dihydroxyacetophenone through standard functional group interconversion and transformations known in the art such as those used in the preparation of F and G.

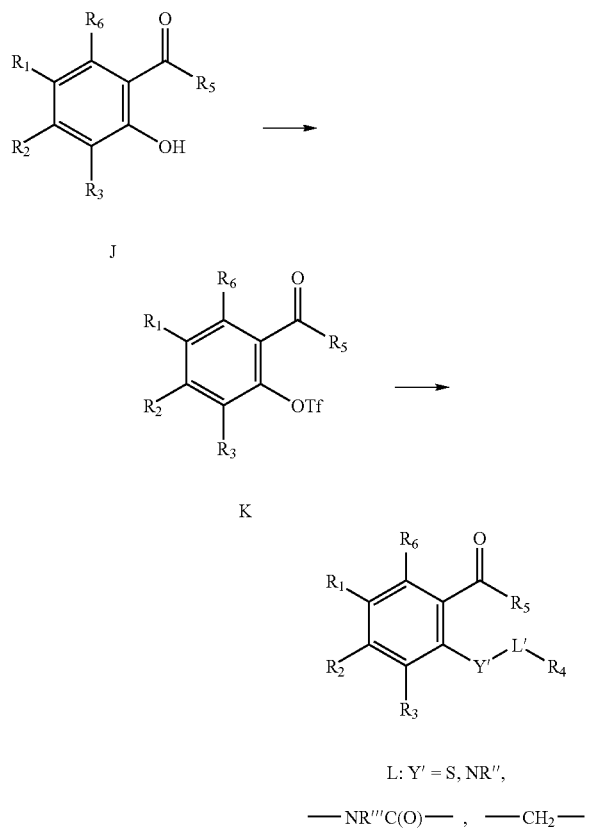

Compounds of the current invention with the general formula L can be prepared from compounds of the general formula J (see above), by triflation to give K (Tf=trifluoromethanesulfonate) and either nucleophilic or palladium mediated substitution of the triflate with an organometallic, thiol, amine or sulfide. Similar chemistry can be used to introduce Y-L-R$_7$ (Y=S, NR", —NR'"C(O)—, —CH$_2$—) groups at the position denoted by R$_3$ or R$_6$)

Another variation is to add, remove or modify the substituents of the product to form new derivatives. This could be achieved again by using standard techniques for functional group inter-conversion, well known in the industry such as those described in Comprehensive organic transformations: a guide to functional group preparations by Larock R C, New York, VCH Publishers, Inc. 1989.

Examples of possible functional group inter-conversions are: —C(O)NRR' from —CO$_2$CH$_3$ by heating with or without catalytic metal cyanide, e.g. NaCN, and HNRR' in CH$_3$OH; —OC(O)R from —OH with e.g., ClC(O)R' in pyridine; —NR—C(S)NR'R" from —NHR with an alkylisothiocyanate or thiocyanic acid; —NRC(O)OR from —NHR with alkyl chloroformate; —NRC(O)NR'R" from —NHR by treatment with an isocyanate, e.g. HN=C=O or RN=C=O; —NRC(O)R' from —NHR by treatment with ClC(O)R' in pyridine; —C(=NR)NR'R" from —C(NR'R") SR'" with H$_3$NR$^+$OAc$^-$ by heating in alcohol; —C(NR'R")SR from —C(S)NR'R" with R—I in an inert solvent, e.g. acetone; —C(S)NR'R" (where R' or R" is not hydrogen) from —C(S)NH$_2$ with HNR'R"; —C(=NCN)—NR'R" from —C(=NR'R")—SR with NH$_2$CN by heating in anhydrous alcohol, alternatively from —C(=NH)—NR'R" by treatment with BrCN and NaOEt in EtOH; —NR—C(=NCN)SR from —NHR' by treatment with (RS)$_2$C=NCN; —NR"SO$_2$R from —NHR' by treatment with ClSO$_2$R by heating in pyridine; —NR'C(S)R from —NR'C(O)R by treatment with Lawesson's reagent [2,4-bis(4-methoxyphenyl)-1, 3,2,4-dithiadiphosphetane-2,4-disulfide]; —NRSO$_2$CF$_3$ from —NHR with triflic anhydride and base, —CH(NH$_2$)CHO from —CH(NH$_2$)C(O)OR' with Na(Hg) and HCl/EtOH; —CH$_2$C(O)OH from —C(O)OH by treatment with SOCl$_2$ then CH$_2$N$_2$ then H$_2$O/Ag$_2$O; —C(O)OH from —CH$_2$C(O)OCH$_3$ by treatment with PhMgX/HX then acetic anhydride then CrO$_3$; R—OC(O)R' from R$^C$(O)R' by R"CO$_3$H; —CCH$_2$OH from —C(O)OR' with Na/R'OH; —CHCH$_2$ from —CH$_2$CH$_2$OH by the Chugaev reaction; —NH$_2$ from —C(O)OH by the Curtius reaction; —NH$_2$ from —C(O)NHOH with TsCl/base then H$_2$O; —CHC(O)CHR from —CHCHOHCHR by using the Dess-Martin Periodinane regent or CrO$_3$/aqH$_2$SO$_4$/acetone; —C$_6$H$_5$CHO from —C$_6$H$_5$CH$_3$ with CrO$_2$Cl$_2$; —CHO from —CN with SnCl$_2$/HCl; —CN from —C(O)NHR with PCl$_5$; —CH$_2$R from —C(O)R with N$_2$H$_4$/KOH; —S(O)$_2$R from —SR with mCPBA.

In order that the present invention may be more readily understood, we provide the following non-limiting examples.

EXAMPLES

General Procedure

Synthetic Experimental
General Procedures
General Procedure A: Alkylation of 1,3-dimethoxyphenols
    NaH (60% dispersion in oil, 1.2 eq.) was added to a stirred solution of 3,5-dimethoxy-4-hydroxytoluene (1.0 eq.) in dry DMF (1.0 M) at room temperature. After the reaction mixture was stirred for 0.25 h, a solution of the bromoalkane (1.03 eq.) in dry DMF (5.0 M) was added, followed by stirring at room temperature overnight. The mixture was quenched with NH$_4$Cl$_{(aq)}$ (sat.), extracted with EtOAc and washed with water. The organic layer was separated and dried over MgSO$_4$ and concentrated under vacuum. The crude product was purified by flash chromatography.
General Procedure B: Friedel-Crafts Reaction with Acetyl Chloride
    A mixture of the substituted benzene (1.0 eq.) and acetyl chloride (1.1 eq.) were stirred under N$_2$ at room temperature for 0.25 h, then TiCl$_4$ (1.1 eq.) was added dropwise. The dark brown mixture was stirred at room temperature for 0.5 h and then quenched with NH$_4$Cl$_{(aq)}$ (sat.), extracted with EtOAc and washed with water. The organic layer was separated, dried over MgSO$_4$ and concentrated under vacuum. The crude product was purified by flash chromatography to give the ketone.
General Procedure C: Selective Demethylation of Methyl Ether
    A solution of BCl$_3$ in DCM (1.0 M, 1.1 eq.) was added to a stirred solution of the methyl ether (1.0 eq.) in dry DCM (0.25 M) under N$_2$ at 0° C. The mixture was stirred for 1-2 h, quenched with NH$_4$Cl$_{(aq)}$ (sat.), extracted with EtOAc and washed with water. The organic layer was separated, dried over MgSO$_4$ and concentrated under vacuum. The crude product was purified by flash chromatography to give the phenol.

General Procedure D: Chlorination of Benzene Ring with N-chlorosuccinimide

To a stirred solution of the substituted benzene (1.0 eq.) in dry DMF (0.10 M) was added N-chlorosuccinimide (1.0 eq.) and the reaction mixture was stirred for 6 h at room temperature. The solvent was distilled and the crude product was dissolved in EtOAc and washed with water. The organic layer was separated, dried over $MgSO_4$, concentrated under vacuum and purified by flash chromatography to give the product.

General Procedure E: Methylation of Benzene Ring Via Bromination Step

Step i.

N-Bromosuccinimide (1.1 eq.) was added to a solution of the arene (1.0 eq.) in dry DMF (0.3 M by the arene) at 0° C. and the reaction was allowed to warm to room temperature and stirred for 3 h. After this time the reaction was quenched with 10% $Na_2S_2O_{3\,(aq)}$ and diluted with $Et_2O$. The organic phase was washed twice with water and once with brine, dried over $MgSO_4$ and concentrated under vacuum to provide the bromide intermediate.

Step ii.

t-Butyllithium (1.7 M in pentane, 2.1 eq.) was added dropwise via syringe to a solution of the bromide intermediate (1.0 eq.) in dry THF (0.25 M) at −78° C. and the reaction was stirred for 2 minutes then treated with methyl iodide (2.0 eq.) and allowed to warm slowly to room temperature. The reaction was quenched with 10% citric acid$_{(aq)}$ and extracted with $Et_2O$. The organic phase was washed with water then brine, dried over $MgSO_4$ and concentrated under vacuum. The crude residue was purified by flash chromatography.

General Procedure F: Alkylation of Phenols

A suspension of the phenol (1.0 eq.), $Cs_2CO_3$ or $K_2CO_3$ (1.5 eq.) and alkyl or benzyl halide (generally 1.2 eq.) in anhydrous DMF (0.2 M) was stirred under $N_2$ at 60° C. until completion as determined by TLC (1-5 h). The reaction mixture was then diluted with EtOAc and washed twice with either citric acid$_{(aq.)}$ (10%) or $HCl_{(aq.)}$ (2 M) and then brine, dried over $MgSO_4$, and concentrated under vacuum. The crude product was purified by flash chromatography.

General Procedure G: Alkylation of Amines and N-heterocycles

To a solution of the bromide (1.0 eq.) in anhydrous DMF (0.2-0.5 M) was added the amine or N-heterocycle (3-4 eq.) and the reaction was stirred at 80-90° C. under a $N_2$ atmosphere until the reaction was complete by TLC (~5 h). The reaction was quenched with $NH_4Cl_{(aq.)}$ (sat.) and extracted with EtOAc. The organic phase was washed with water then brine, dried over $MgSO_4$ and concentrated under vacuum. The crude residue was purified by flash chromatography.

General Procedure H: Alkylation of 3,5-dimethoxytoluene

A solution of n-butyllithium in hexanes (1.7 M, 1.2 eq.) was added over 0.25 h to a solution of 3,5-dimethoxytoluene (1.0 eq.) in THF (1 M) at 0° C. The reaction mixture was stirred at 0° C. for 1 h then at room temperature for 3 h. The reaction was cooled to 0° C. and a solution of the alkyl bromide (1.2 eq.) in toluene (2 M) was added over 0.1 h. The reaction mixture was allowed to warm to room temperature and heated to 80° C. for 3-4 h. The reaction was quenched slowly with water and partitioned over EtOAc and water. The phases were separated and the aqueous phase was extracted twice with EtOAc. The pooled organics were washed with brine, dried over $Na_2SO_4$ and concentrated under vacuum. The residue was purified by flash chromatography.

General Procedure I: Alkylation of phenols

To a stirred suspension the phenol (1.0 eq.), $K_2CO_3$ (2.0 eq.) and NaI (0.30 eq.) (pre-dried under vacuum at 100° C. for 5 h) in dry DMF or DMSO (0.1 M of phenol) was added the alkyl chloride (2.0 eq.) and the reaction was heated at 60° C. until the reaction was complete by TLC (~16 h). After this time the reaction was cooled, diluted with EtOAc and washed thrice with water. The organic phase was dried over $MgSO_4$, concentrated under vacuum and the crude residue was purified by flash chromatography.

General Procedure J: Alkylation of N-heterocycles

To a solution of the bromide (1.0 eq.) in anhydrous DMF (0.2-0.5 M) was added diisopropylethylamine (3.5 eq.) and the N-heterocycle hydrochloride salt (2.5 eq.) and the reaction was stirred at 50-60° C. under a $N_2$ atmosphere until the reaction was complete by TLC (~16 h). The reaction was quenched with $NH_4Cl_{(aq.)}$ (sat.) and extracted with EtOAc. The organic layer was washed with water then brine, dried over $MgSO_4$ and concentrated under vacuum. The crude residue was purified by flash chromatography.

General Procedure K: Alkylation of N-heterocycles

To a solution of the N-heterocycle hydrochloride salt (2.5 eq.) in anhydrous DMF (1 M) was added NaH (60% dispersion in oil, 3.0 eq.) and the reaction was stirred at room temperature for 2-3 h. To this was added the bromide (1.0 eq.) in anhydrous DMF (0.2-0.5 M) and the reaction was stirred at 50-60° C. under a $N_2$ atmosphere until the reaction was complete by TLC (~16 h). The reaction was quenched with $NH_4Cl_{(aq.)}$ (sat.) and extracted with EtOAc. The organic phase was washed with water then brine, dried over $MgSO_4$ and concentrated under vacuum. The crude residue was purified by flash chromatography.

General Procedure L: Alkylation of Amines and N-heterocycles

To a solution of the bromide (1.0 eq.) in anhydrous DMF (0.2-0.5 M) was added $Cs_2CO_3$ or $K_2CO_3$ (2-2.5 eq.) and the amine (1.5-2.5 eq.) and the reaction was stirred at 50-60° C. under a $N_2$ atmosphere until the reaction was complete by TLC (~16 h). The reaction was quenched with $NH_4Cl_{(aq.)}$ (sat.) and extracted with EtOAc. The organic phase was washed with water then brine, dried over $MgSO_4$ and concentrated under vacuum. The crude residue was purified by flash chromatography.

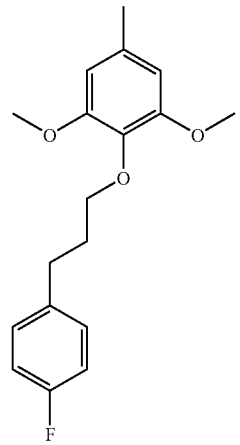

Example 1

1a) 2-(3-(4-Fluorophenyl)propoxy)-1,3-dimethoxy-5-methylbenzene 3,5-Dimethoxy-4-hydroxy-toluene (1.0 g, 5.95 mmol) and 1-(3-bromopropyl)-4-fluorobenzene (1.5 g, 6.15 mmol) were reacted as described under General Procedure A and the crude product was purified by flash chromatography (silica-gel, hexane/Et₂O 19:1) to afford the title compound (1.64 g, 91%) as a colourless oil. ¹H NMR (300 MHz, CDCl₃) δ 7.31-7.19 (m, 6H), 4.06 (t, J=6.4 Hz, 2H), 3.95 (s, 3H), 3.90 (s, 3H), 2.81 (t, J=7.7 Hz, 2H), 2.46 (s, 3H), 2.10-2.05 (m, 2H).

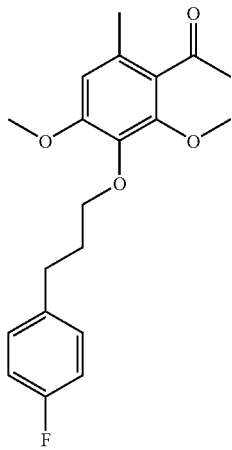

1b) 1-(3-(3-(4-Fluorophenyl)propoxy)-2,4-dimethoxy-6-methyl-methylphenyl)ethanone Example 1a (380 mg, 1.25 mmol) was reacted as described under General Procedure B and the crude product was purified by flash chromatography (silica-gel, hexane/Et₂O, gradient to 1:4) to afford the title compound (409 mg, 95%) as a light cream oil. ¹H NMR (300 MHz, CDCl₃) δ 7.19-7.14 (m, 2H), 6.98-6.92 (m, 2H), 6.47 (s, 1H), 3.97 (t, J=6.3 Hz, 2H), 3.87 (s, 3H), 3.82 (s, 3H), 2.80 (t, J=7.4 Hz, 2H), 2.47 (s, 3H), 2.21 (s, 3H), 2.06-1.97 (m, 2H).

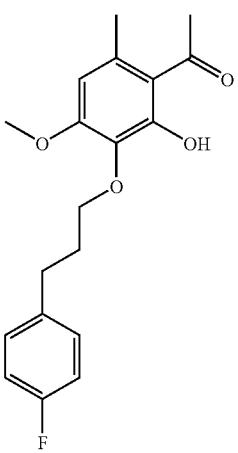

1c) 1-(3-(3-(4-Fluorophenyl)propoxy)-2-hydroxy-4-methoxy-6-methylphenyl)ethanone Example 1b (300 mg, 0.87 mmol) was reacted as described under General Procedure C and the crude product was purified by flash chromatography (silica-gel, hexane/Et₂O, gradient to 1:4) to afford the title compound (281 mg, 98%) as a light cream oil. ¹H NMR (300 MHz, CDCl₃) δ 7.19-7.14 (m, 2H), 6.98-6.91 (m, 2H), 6.28 (s, 1H), 3.99 (t, J=6.4 Hz, 2H), 3.86 (s, 3H), 2.80 (t, J=7.5 Hz, 2H), 2.60 (s, 3H), 2.52 (s, 3H), 2.10-1.97 (m, 2H).

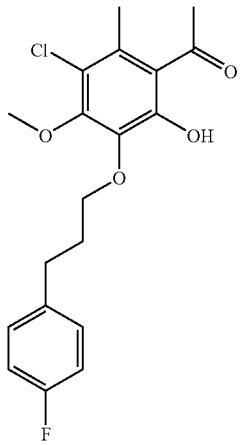

1d) 1-(3-Chloro-5-(3-(4-fluorophenyl)propoxy)-6-hydroxy-4-methoxy-2-methylphenyl)ethanone Example 1c (110 mg, 0.33 mmol) was reacted as described under General Procedure D and the crude product was purified by flash chromatography (silica-gel, hexane/Et₂O, gradient to 1:4) to afford the title compound (121 mg, 99.5%) as a light cream oil. ¹H NMR (300 MHz, CDCl₃) δ 8.71 (s, 1H), 7.18-7.13 (m, 2H), 6.98-6.93 (m, 2H), 4.07 (t, J=6.5 Hz, 2H), 3.88 (s, 3H), 2.77 (t, J=7.3 Hz, 2H), 2.56 (s, 3H), 2.38 (s, 3H), 2.09-1.20 (m, 2H).

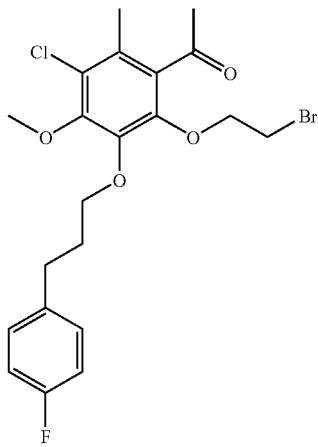

1e) 1-(2-(2-Bromoethoxy)-5-chloro-3-(3-(4-fluorophenyl)propoxy)-4-methoxy-6-methylphenyl)ethanone Example 1d (110 mg, 0.30 mmol) was reacted with 1,2-dibromoethane (3.0 eq.) as described under General Procedure F to afford the title compound (86 mg, 64%) as light cream oil. ¹H NMR (300 MHz, CDCl₃) δ 7.19-7.14 (m, 2H), 6.99-6.93 (m, 2H), 4.28 (t, J=6.2 Hz, 2H), 4.06 (t, J=6.4 Hz, 2H), 3.64 (s, 3H), 3.50 (t, J=6.2 Hz, 2H), 2.78 (t, J=7.4 Hz, 2H), 2.49 (s, 3H), 2.19 (s, 3H), 2.05-2.02 (m, 2H).

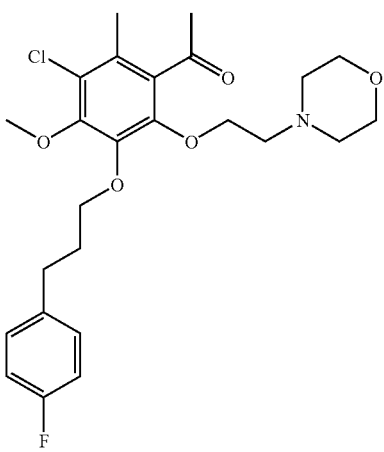

1f) 1-(3-Chloro-5-(3-(4-fluorophenyl)propoxy)-4-methoxy-2-methyl-6-(2-morpholinoethoxy)phenyl)ethanone Example 1e (83 mg, 0.18 mmol) was reacted with morpholine (3 mL) as described under General Procedure G and the crude mixture was purified by flash chromatography (silica-gel, DCM/EtOAc/MeOH 1:0:0, 9:8:2) to afford the title compound (23 mg, 26%) as light creamy oil. $^1$H NMR (300 MHz, CDCl$_3$) δ 7.20-7.13 (m, 2H), 6.99-6.93 (m, 2H), 4.10-4.03 (m, 4H), 3.86 (s, 3H), 3.68 (t, J=4.4 Hz, 4H), 2.78 (t, J=7.6 Hz, 2H), 2.62 (t, J=5.5 Hz, 2H), 2.51 (s, 3H), 2.46 (t, J=4.45 Hz, 4H), 2.18 (s, 3H), 2.07-1.98 (m, 2H). MS (ES$^+$) m/z 479.9 (M+H$^+$).

Example 2

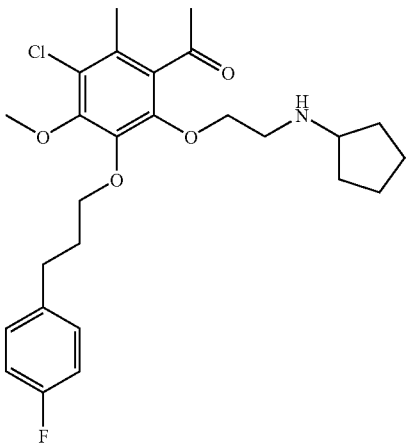

1-(3-Chloro-6-(cyclopentylamino)ethoxy)-5-(3-(4-fluorophenyl)propoxy-4-methoxy-2-methylphenyl)ethanone Example 1e (180 mg, 0.40 mmol) was reacted with cyclopentylamine (4 mL) as described under General Procedure G and the crude mixture was purified by flash chromatography (silica-gel, DCM/EtOAc/MeOH 1:0:0, 9:8:2) to afford the title compound (32 mg, 17%) as light cream oil. $^1$H NMR (300 MHz, CDCl$_3$) δ 7.17-7.13 (m, 2H), 6.98-6.92 (m, 2H), 4.13 (t, J=5.2 Hz, 2H), 4.03 (t, J=6.4 Hz, 2H), 3.86 (s, 3H), 3.09-3.05 (m, 1H), 2.84 (t, J=5.2 Hz, 4H), 2.77 (t, J=7.4 Hz, 2H), 2.48 (s, 3H), 2.18 (s, 3H), 2.03-1.97 (m, 2H), 1.85-1.75 (m, 4H), 1.37-1.23 (m, 2H). MS (ES$^+$) m/z 477.9 (M+H$^+$).

Example 3

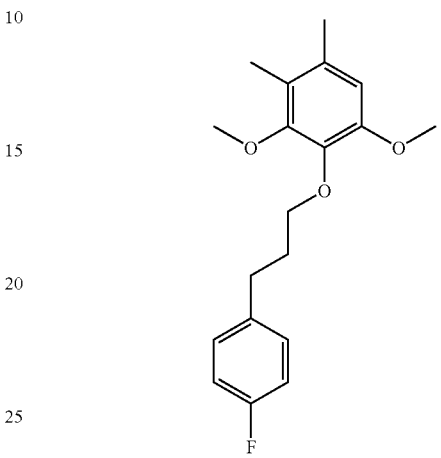

3a) 4-[3-(4-Fluoro-phenyl)-propoxy]-3,5-dimethoxy-1,2-dimethyl-benzene

Example 1a (1.0 g, 3.14 mmol) was reacted as described under General Procedure E Step i) to afford the bromide intermediate (1.16 g, 93%). A portion of this material (500 mg, 1.3 mmol) was reacted as described under General Procedure E Step ii) and the crude residue was purified by flash chromatography (silica-gel, hexane/Et$_2$O 19:1) to provide the product as a clear oil (310 mg, 75%). $^1$H NMR (300 MHz, CDCl$_3$) δ 7.20-7.15 (m, 2H), 6.97 (m, 2H), 6.49 (s, 1H), 3.97 (t, J=6.3 Hz, 2H), 3.81 (s, 3H), 3.79 (s, 3H), 2.81 (t, J=7.5 Hz, 2H), 2.21 (s, 3H), 2.10 (s, 3H), 2.06-1.96 (m, 2H).

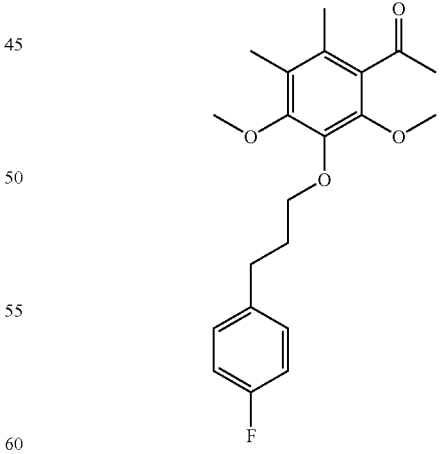

3b) 1-{3-[3-(4-Fluoro-phenyl)-propoxy]-2,4-dimethoxy-5,6-dimethyl-phenyl}-ethanone Example 3a (180 mg, 0.57 mmol) was reacted as described under General Procedure B and the crude product was purified by flash chromatography (silica-gel, hexane/EtOAc, 9:1) to afford the title compound as a clear oil (55 mg, 27%). $^1$H NMR (300 MHz, CDCl$_3$) δ 7.19-7.15 (m, 2H), 6.98-6.92 (m, 2H), 4.01 (t, J=6.3 Hz, 2H), 3.82 (s, 3H), 3.80 (s, 3H), 2.80 (t, J=7.4 Hz, 2H), 2.46 (s, 3H), 2.11 (s, 3H), 2.05 (s, 3H), 2.06-1.98 (m, 2H).

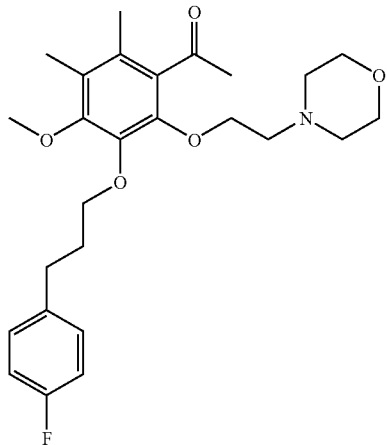

3c) 1-[3-[3-(4-Fluoro-phenyl)-propoxy]-4-methoxy-5,6-dimethyl-2-(2-morpholin-4-yl-ethoxy)-phenyl]-ethanone Example 3b (50 mg, 0.139 mmol) was reacted with BCl$_3$ (1.1 eq.) according to General Procedure C. The material thus obtained was then reacted with 1,2-dibromoethane (3.0 eq.) according to General Procedure F and the product bromide reacted with morpholine according to General Procedure G to afford the product as a clear oil (21 mg, 33% over 3 steps). $^1$H NMR (300 MHz, CDCl$_3$) δ 7.19-7.14 (m, 2H), 6.98-6.93 (m, 2H), 4.09-4.00 (m, 4H), 3.77 (s, 3H), 3.71-3.68 (m, 4H), 2.79 (t, J=7.4 Hz, 2H), 2.62 (t, J=5.7 Hz, 2H), 2.50 (s, 3H), 2.49-2.46 (m, 4H), 2.11 (s, 3H), 2.05 (s, 3H), 2.05-1.97 (m, 2H).

Example 4

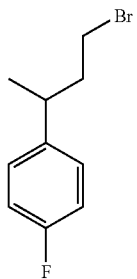

4a) 1-(3-Bromo-1-methyl-propyl)-4-fluoro-benzene

A solution of ethyl 3-(4-fluorophenyl)butanoate (2.85 g, 13.6 mmol) in THF (10 mL) was added to a solution of lithium aluminium hydride (0.77 g, 1.5 mmol) in THF (60 mL) at 0° C. The reaction was stirred at room temperature overnight, then cooled to 0° C., quenched with NH$_4$Cl$_{(aq)}$ (sat., 50 mL) and extracted with EtOAc (3×100 mL). The pooled organics were washed with brine (100 mL), dried over Na$_2$SO$_4$ and concentrated under vacuum to give the alcohol, which was used directly in the next step. Bromine (1.03 mL, 20.0 mmol) was added dropwise to a solution of triphenylphosphine (5.24 g, 20.0 mmol) in DCM (80 mL) at 0° C. until an orange colour persisted. The reaction mixture was stirred at room temperature for 1.5 h, then a solution of the alcohol (2.37 g, 14.1 mmol) in DCM (20 mL) was added and the reaction mixture stirred overnight. The reaction mixture was concentrated under vacuum and the resulting residue was sonicated for 0.1 h in petroleum ether (100 mL). The suspension was filtered and the white solid washed with petroleum spirit. The washings were concentrated under vacuum to give the title compound (2.56 g, 81% over 2 steps) as a colourless oil. $^1$H NMR (300 MHz, CDCl$_3$) δ 7.18-7.14 (m, 2H), 7.02-6.96 (m, 2H), 3.35-3.28 (m, 1H), 3.20-3.11 (m, 1H), 3.02-2.90 (m, 1H), 2.11-2.04 (m, 2H), 1.26 (d, J=6.9 Hz, 3H).

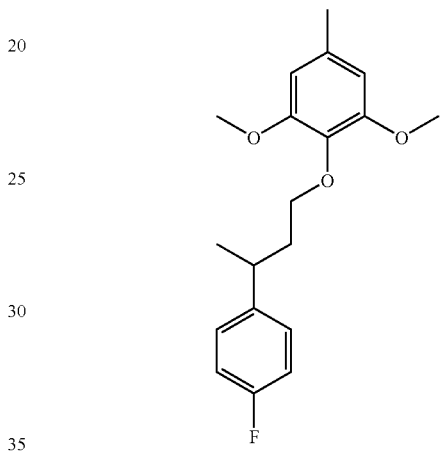

4b) 2-[3-(4-fluorophenyl)butoxy]-1,3-dimethoxy-5-methylbenzene

Example 4a (2.54 g, 11 mmol) and 3,5-dimethoxy-4-hydroxy-toluene (1.68 g, 10 mmol) were reacted as described under General Procedure A and the crude product was purified by flash chromatography (silica-gel, hexane/EtOAc 19:1) to provide the product as a clear oil (2.6 g, 82%). $^1$H NMR (300 MHz, CDCl$_3$) δ 7.20-7.15 (m, 2H), 6.97-6.91 (m, 2H), 6.35 (s, 2H), 3.85-3.37 (m, 8H), 3.10-3.02 (m, 1H), 3.28 (s, 3H), 2.04-1.89 (m, 2H), 1.26 (d, J=6.9 Hz, 3H).

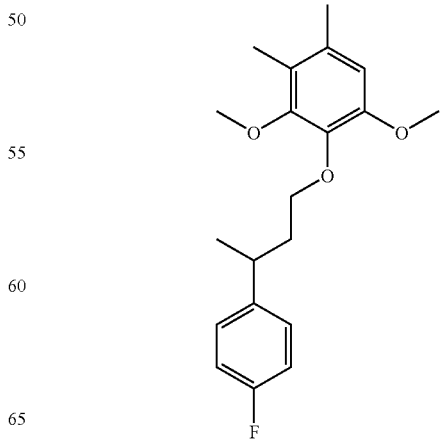

4c) 4-[3-(4-Fluoro-phenyl)butoxy]-3,5-dimethoxy-1,2-dimethylbenzene

Example 4b (640 mg, 2.01 mmol) was reacted as described under General Procedure E Step i) to afford the bromide intermediate (750 mg, 94%). This material was reacted as described under General Procedure E Step ii) except 1.1 eq. of n-butyllithium (2 M solution in cyclohexane) was used instead of 2.1 eq. of t-butyllithium to afford the title compound (600 mg, 97%). $^1$H NMR (300 MHz, CDCl$_3$) δ 7.20-7.15 (m, 2H), 6.98-6.92 (m, 2H), 6.46 (s, 1H), 3.92-3.81 (m, 2H), 3.78 (s, 3H), 3.77 (s, 3H), 3.09-3.02 (m, 1H), 2.19 (s, 3H), 2.08 (s, 3H), 2.01-1.94 (m, 2H), 1.27 (d, J=7.0 Hz, 3H).

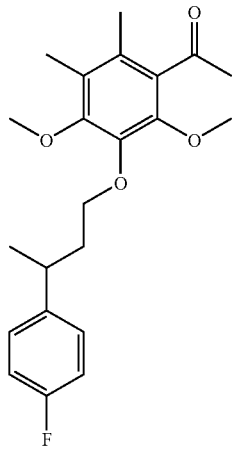

4d) 1-{3-[3-(4-Fluoro-phenyl)-butoxy]-2,4-dimethoxy-5,6-dimethyl-phenyl}-ethanone Example 4c (595 mg, 1.79 mmol) was reacted as described under General Procedure B and the crude product was purified by flash chromatography (silica-gel, hexane/EtOAc 19:1, 9:1, 4:1) to afford initially quantities of recovered starting material (145 mg, 24%) then the product as a clear oil (240 mg, 36%). $^1$H NMR (300 MHz, CDCl$_3$) δ 7.19-7.15 (m, 2H), 6.99-6.93 (m, 2H), 3.91-3.85 (m, 2H), 3.78 (s, 3H), 3.76 (s, 3H), 3.06-2.99 (m, 1H), 2.45 (s, 3H), 2.09 (s, 3H), 2.04 (s, 3H), 2.04-1.96 (m, 2H), 1.28 (d, J=7.0 Hz, 3H). MS (ES$^+$) m/z 375.0 (M+H$^+$).

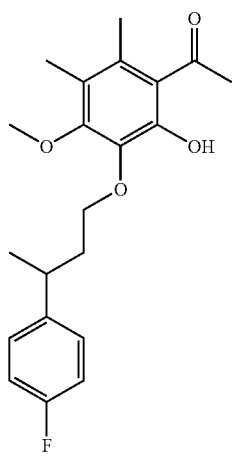

4e) 1-{3-[3-(4-Fluoro-phenyl)-butoxy]-2-hydroxy-4-methoxy-5,6-dimethyl-phenyl}-ethanone Example 4d (240 mg, 0.64 mmol) was reacted as described under General Procedure C and the crude residue was rapidly filtered through a short silica-gel plug, eluting with hexane/EtOAc (9:1) to afford the product (220 mg, 95%). $^1$H NMR (300 MHz, CDCl$_3$) δ 8.44 (s, 1H), 7.18-7.14 (m, 2H), 7.00-6.93 (m, 2H), 3.91 (t, J=6.6 Hz, 2H), 3.77 (s, 3H), 3.02-2.94 (m, 1H), 2.54 (s, 3H), 2.21 (s, 3H), 2.07 (s, 3H), 2.04-1.98 (m, 2H), 1.28 (d, J=7.0 Hz, 3H). MS (ES$^+$) m/z 361.0 (M+H$^+$).

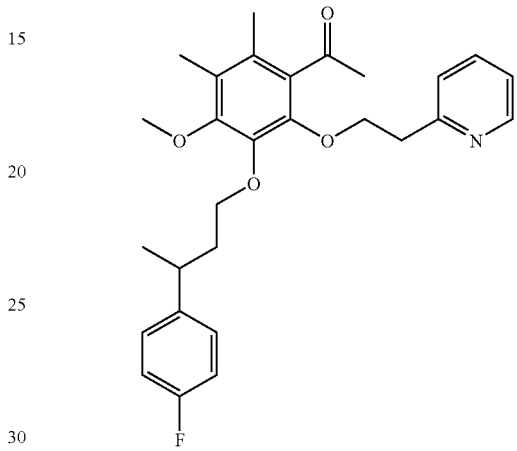

4f) 1-[3-[3-(4-Fluoro-phenyl)-butoxy]-4-methoxy-5,6-dimethyl-2-(2-pyridin-2-yl-ethoxy)-phenyl]-ethanone Example 4e (100 mg, 0.28 mmol) was reacted with 2-pyridin-2-ylethyl methanesulfonate (1.6 eq.) as described under General Procedure F to give the title compound (56 mg, 43%). $^1$H NMR (300 MHz, CDCl$_3$) δ 8.51 (d, J=4.2 Hz, 1H), 7.57 (dt, J=7.7, 1.8 Hz, 1H), 7.19-7.09 (m, 4H), 6.96-6.91 (m, 2H), 4.34 (t, J=6.6 Hz, 2H), 3.83 (t, J=6.6 Hz, 2H), 3.73 (s, 3H), 3.11 (6.6 Hz, 2H), 2.99-2.92 (m, 1H), 2.26 (s, 3H), 2.07 (s, 3H), 2.00 (s, 3H), 1.95-1.88 (m, 2H), 1.25 (d, J=7.0 Hz, 3H).

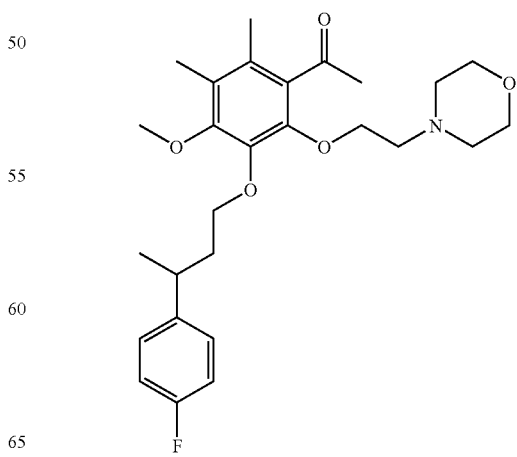

Example 5

1-[3-[3-(4-Fluoro-phenyl)-butoxy]-4-methoxy-5,6-dimethyl-2-(2-morpholin-4-yl-ethoxy)-phenyl]-ethanone Example 4e (100 mg, 0.21 mmol) was reacted over two steps in the same manner as described for the formation of Example 1f from 1d. The title compound was afforded in 66% yield (70 mg) over 2 steps. $^1$H NMR (300 MHz, CDCl$_3$) δ 7.18-7.14 (m, 2H), 6.99-6.92 (m, 2H), 4.03 (t, J=5.6 Hz, 2H), 3.91 (t, J=6.7 Hz, 2H), 3.73 (s, 3H), 3.70-3.67 (m, 4H), 3.03-2.96 (m, 1H), 2.59 (t, J=5.7 Hz, 2H), 2.48 (s, 3H), 2.48-2.45 (m, 4H), 2.09 (s, 3H), 2.03 (s, 3H), 2.03-1.95 (m, 2H), 1.28 (d, J=7.0 Hz, 3H). MS (ES$^+$) m/z 474.0 (M+H$^+$).

Example 6

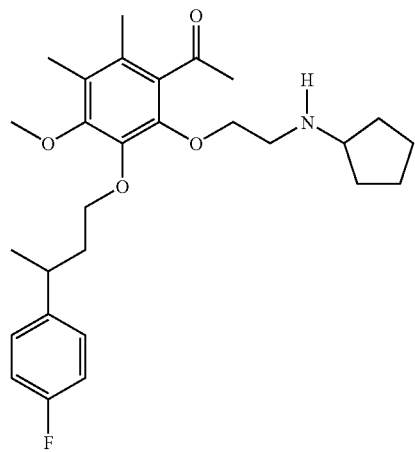

1-{2-(2-Cyclopentylamino-ethoxy)-3-[3-(4-fluoro-phenyl)-butoxy]-4-methoxy-5,6-dimethyl-phenyl}-ethanone Example 4e (160 mg, 0.34 mmol) was reacted over two steps in the same manner as described for the formation of Example 2 from 1d. The title compound was afforded in 77% yield (130 mg) over 2 steps. $^1$H NMR (300 MHz, CDCl$_3$) δ 7.18-7.13 (m, 2H), 6.98-6.92 (m, 2H), 4.05 (t, J=5.1 Hz, 2H), 3.90 (t, J=6.7 Hz, 2H), 3.73 (s, 3H), 3.11-2.93 (m, 2H), 2.80 (t, J=5.1 Hz, 2H), 2.46 (s, 3H), 2.09 (s, 3H), 2.01 (s, 3H), 2.01-1.96 (m, 2H), 1.84-1.77 (m, 2H), 1.68-1.50 (m, 4H), 1.36-1.24 (m, 5H). MS (ES$^+$) m/z 472.0 (M+H$^+$).

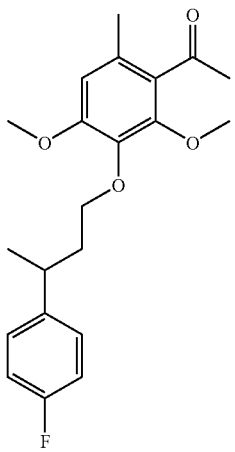

Example 7

7a) 1-{3-[3-(4-Fluoro-phenyl)-butoxy]-2,4-dimethoxy-6-methyl-phenyl}-ethanone Example 4b (2.6 g, 8.2 mmol) was reacted as described under General Procedure B to offer the title compound (2.5 g, 86%) as creamy oil. $^1$H NMR (300 MHz, CDCl$_3$) δ 7.19-7.15 (m, 2H), 6.98-6.93 (m, 2H), 6.44 (s, 1H), 3.91-3.75 (m, 8H), 3.10-2.99 (m, 1H), 3.45 (s, 3H), 2.19 (s, 3H), 2.04-1.91 (m, 2H), 1.27 (d, J=6.9 Hz, 3H).

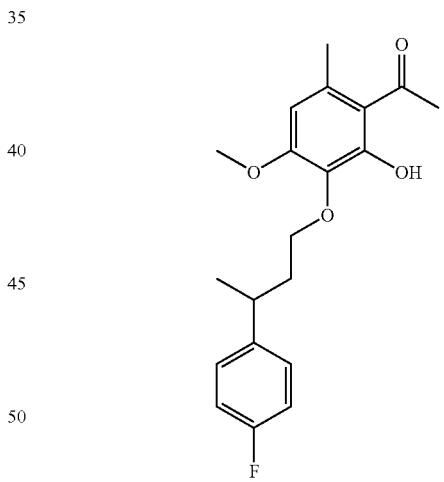

7b) 1-{3-[3-(4-Fluoro-phenyl)-butoxy]-2-hydroxy-4-methoxy-6-methyl-phenyl}-ethanone Example 7a (400 mg, 1.11 mmol) was reacted as described under General Procedure C to afford the title compound (350 mg, 91%) as an oil. $^1$H NMR (300 MHz, CDCl$_3$) δ 11.71 (s, 1H), 7.20-7.15 (m, 2H), 6.99-6.92 (m, 2H), 6.26 (s, 1H), 3.91-3.80 (m, 2H), 3.83 (s, 3H), 3.09-3.01 (m, 1H), 2.59 (s, 3H), 2.49 (s, 3H), 2.06-1.91 (m, 2H), 1.27 (d, J=7.0 Hz, 3H).

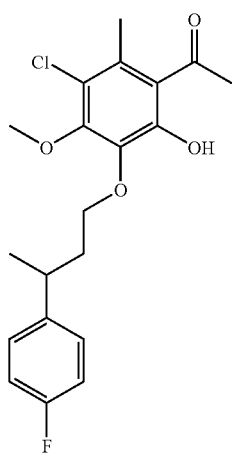

7c) 1-{3-Chloro-5-[3-(4-fluoro-phenyl)-butoxy]-6-hydroxy-4-methoxy-2-methyl-phenyl}-ethanone Example 7b (350 mg, 1.0 mmol) was reacted as described under General Procedure D to afford the title compound (320 mg, 83%) as a clear oil. $^1$H NMR (300 MHz, CDCl$_3$) δ 8.46 (s, 1H), 7.18-7.13 (m, 2H), 7.00-6.94 (m, 2H), 3.95 (t, J=6.6 Hz, 2H), 3.86 (s, 3H), 3.00-2.93 (m, 1H), 2.55 (s, 3H), 2.36 (s, 3H), 2.06-1.94 (m, 2H), 1.28 (d, J=7.0 Hz, 3H). MS (ES$^+$) m/z 380.9 (M+H$^+$).

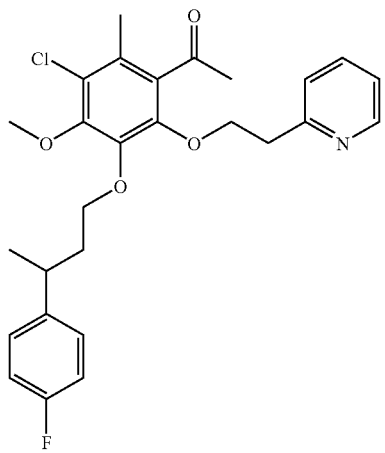

7d) 1-[3-Chloro-5-[3-(4-fluoro-phenyl)-butoxy]-4-methoxy-2-methyl-6-(2-pyridin-2-yl-ethoxy)-phenyl]-ethanone Example 7c (500 mg, 1.31 mmol) was reacted with 2-pyridin-2-ylethyl methanesulfonate (2.0 eq.) as described under General Procedure F to give the title compound as an oil (410 mg, 89%). $^1$H NMR (300 MHz, CDCl$_3$) δ 8.52 (d, J=4.1 Hz, 1H), 7.58 (dt, J=7.7, 1.8 Hz, 1H), 7.17-7.10 (m, 4H), 6.97-6.90 (m, 2H), 4.37 (t, J=6.6 Hz, 2H), 3.85 (t, J=6.6 Hz, 2H), 3.81 (s, 3H), 3.10 (t, J=6.5 Hz, 2H), 2.98-2.91 (m, 1H), 2.26 (s, 3H), 2.14 (s, 3H), 1.96-1.88 (m, 2H), 1.25 (d, J=7.0 Hz, 3H). MS (ES$^+$) m/z 485.9 (M+H$^+$).

Example 8

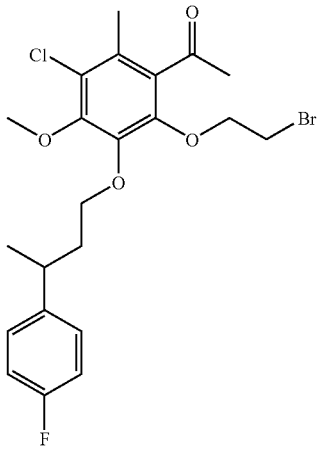

8a) 1-{2-(2-Bromo-ethoxy)-5-chloro-3-[3-(4-fluoro-phenyl)-butoxy]-4-methoxy-6-methyl-phenyl}-ethanone Example 7c (511 mg, 1.34 mmol) was reacted with 1,2-dibromoethane (20.0 eq.) as described under General Procedure F to afford the title compound (641 mg, quantitative yield) as a light brown oil. $^1$H NMR (300 MHz, CDCl$_3$) δ 7.20-7.15 (m, 2H), 7.01-6.96 (m, 2H), 4.26 (t, J=6.2 Hz, 2H), 3.96 (t, J=6.6 Hz, 2H), 3.84 (s, 3H), 3.49 (t, J=6.2 Hz, 2H), 2.99 (m, 1H), 2.50 (s, 3H), 2.19 (s, 3H), 2.07-2.01 (m, 2H), 1.30 (d, J=6.9 Hz, 3H). MS (ES$^+$) m/z 487.3 (M+H$^+$).

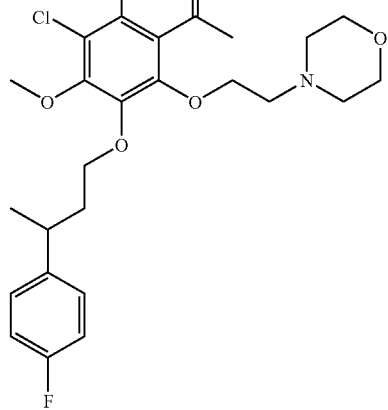

8b) 1-[3-Chloro-5-[3-(4-fluoro-phenyl)-butoxy]-4-methoxy-2-methyl-6-(2-morpholin-4-yl-ethoxy)-phenyl]-ethanone Example 8a (100 mg, 0.21 mmol) was reacted with morpholine (6.0 eq.) as described under General Procedure G. The title compound was afforded as an oil (72 mg, 71%). $^1$H NMR (300 MHz, CDCl$_3$) δ 7.18-7.13 (m, 2H), 6.99-6.89 (m, 2H), 4.05 (t, J=5.7 Hz, 2H), 3.94 (t, J=6.7 Hz, 2H), 3.82 (s, 3H), 3.70-3.67 (m, 4H), 3.02-2.95 (m, 1H), 2.59 (t, J=5.7 Hz, 2H), 2.49 (s, 3H), 2.47-2.44 (m, 4H), 2.17 (s, 3H), 2.03-1.96 (m, 2H), 1.28 (d, J=7.0 Hz, 3H). MS (ES$^+$) m/z 493.9 (M+H$^+$).

Example 9

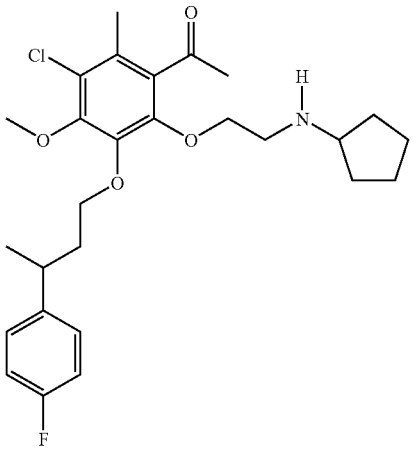

1-[3-Chloro-6-(2-cyclopentylamino-ethoxy)-5-[3-(4-fluoro-phenyl)-butoxy]-4-methoxy-2-methyl-phenyl]-ethanone Example 8a (100 mg, 0.21 mmol) was reacted with cyclopentylamine (6.0 eq.) as described under General Procedure G. The title compound was afforded as an oil (65 mg, 65%). $^1$H NMR (300 MHz, CDCl$_3$) δ 7.17-7.13 (m, 2H), 6.99-6.93 (m, 2H), 4.07 (t, J=5.2 Hz, 2H), 3.92 (t, J=6.7 Hz, 2H), 3.81 (s, 3H), 3.06 (quintet, J=6.6 Hz, 1H), 3.01-2.93 (m, 1H), 2.81 (t, J=5.2 Hz, 2H), 2.46 (s, 3H), 2.16 (s, 3H), 2.03-1.96 (m, 2H), 1.84-1.76 (m, 2H), 1.68-1.49 (m, 4H), 1.33-1.23 (m, 2H), 1.27 (d, J=7.0 Hz, 3H).

Example 10

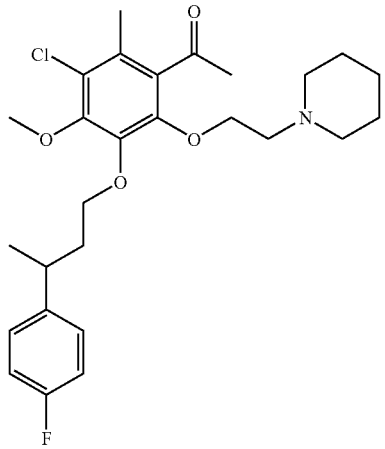

1-[3-Chloro-5-[3-(4-fluoro-phenyl)-butoxy]-4-methoxy-2-methyl-6-(2-piperidin-1-yl-ethoxy)-phenyl]-ethanone Example 8a (90 mg, 0.19 mmol) was reacted with piperidine (8.0 eq.) as described under General Procedure G and the crude mixture was purified by flash chromatography (silica gel, DCM/MeOH 100:0, 49:1) to afford the title compound (40 mg, 43%) as a pale yellow oil. $^1$H NMR (300 MHz, CDCl$_3$) δ 7.20-7.15 (m, 2H), 7.01-6.95 (m, 2H), 4.07 (t, J=6.0 Hz, 2H), 3.95 (t, J=6.8 Hz, 2H), 3.83 (s, 3H), 3.00 (m, 1H), 2.59 (t, J=6.0 Hz, 3H), 2.50 (s, 3H), 2.45-2.35 (m, 4H), 2.18 (s, 3H), 2.05-1.98 (m, 2H), 1.61-1.54 (m, 4H), 1.46-1.42 (m, 2H), 1.24 (d, J=6.9 Hz, 3H). MS (ES$^+$) m/z 492.3 (M+H$^+$).

Example 11

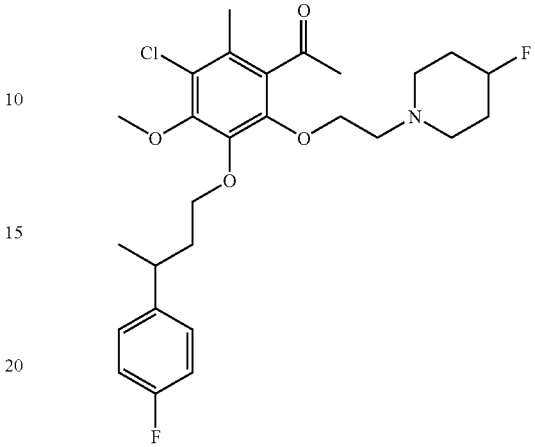

1-{3-Chloro-5-[3-(4-fluoro-phenyl)-butoxy]-6-[2-(4-fluoro-piperidin-1-yl)-ethoxy]-4-methoxy-2-methyl-phenyl}-ethanone Example 8a (89 mg, 0.18 mmol) was reacted with 4-fluoropiperidine hydrochloride (1.6 eq.) as described under General Procedure J and the crude mixture was purified by flash chromatography (silica gel, Et$_2$O/hexane 3:2) to afford the title compound (38 mg, 41%) as a pale yellow oil. $^1$H NMR (300 MHz, CDCl$_3$) δ 7.20-7.15 (m, 2H), 7.01-6.95 (m, 2H), 4.66 (m, 1H), 4.05 (t, J=5.9 Hz, 2H), 3.95 (t, J=6.6 Hz, 2H), 3.83 (s, 3H), 3.00 (m, 1H), 2.64-2.59 (m, 4H), 2.50 (s, 3H), 2.44-2.36 (m, 2H), 2.18 (s, 3H), 2.05-1.97 (m, 2H), 1.94-1.81 (m, 4H), 1.30 (d, J=6.9 Hz, 3H). MS (ES$^+$) m/z 510.2 (M+H$^+$).

Example 12

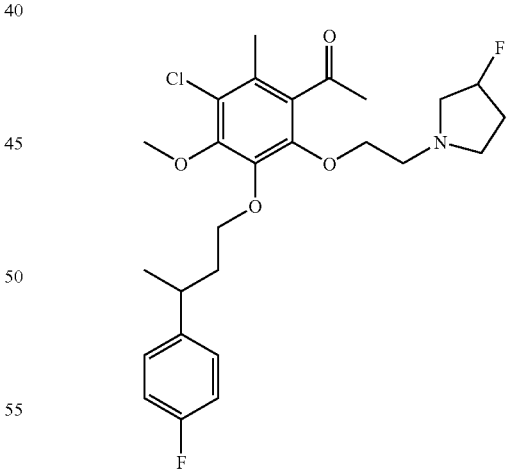

1-{3-Chloro-5-[3-(4-fluoro-phenyl)-butoxy]-6-[2-(R-3-fluoro-pyrrolidin-1-yl)-ethoxy]-4-methoxy-2-methyl-phenyl}-ethanone Example 8a (93 mg, 0.19 mmol) was reacted with (R)-3-fluoropyrrolidine hydrochloride (2.4 eq.) as described under General Procedure J and the crude mixture was purified by flash chromatography (silica gel, Et$_2$O/hexane 3:2) to afford the title compound (27 mg, 29%) as a pale yellow oil. $^1$H NMR (300 MHz, CDCl$_3$) δ 7.20-7.15 (m, 2H), 7.00-6.95 (m, 2H), 5.16 (m, 1H), 4.07 (t, J=5.9 Hz, 2H), 3.95 (t, J=6.8 Hz, 2H), 3.83 (s, 3H), 3.03-2.67 (m, 6H), 2.50 (s, 3H), 2.46 (m, 1H), 2.18 (s, 3H), 2.15-1.98 (m, 4H), 1.29 (d, J=7.2 Hz, 3H). MS (ES$^+$) m/z 496.3 (M+H$^+$).

Example 13

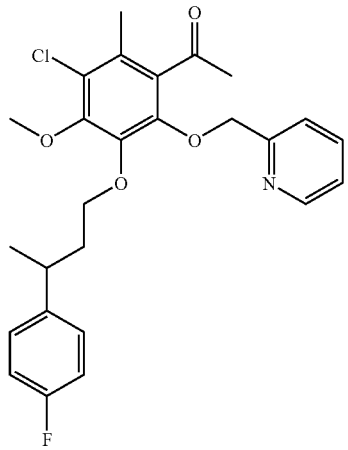

1-[3-Chloro-5-[3-(4-fluoro-phenyl)-butoxy]-4-methoxy-2-methyl-6-(pyridin-2-ylmethoxy)-phenyl]-ethanone Example 8a (91 mg, 0.24 mmol) was reacted with 2-(bromomethyl)-pyridine hydrobromide (1.6 eq.) as described under General Procedure F and the crude mixture was purified by flash chromatography (silica gel, Et$_2$O/hexane 1:1) to afford the title compound (55 mg, 49%) as a pale yellow oil. $^1$H NMR (300 MHz, CDCl$_3$) δ 8.57 (m, 1H), 7.71 (dt, J=Hz, 1.8, 7.7 Hz, 1H), 7.42 (d, J=7.8 Hz, 1H), 7.24 (m, 1H), 7.11-7.06 (m, 2H), 6.94-6.88 (m, 2H), 5.17 (s, 2H), 3.95 (t, J=6.8 Hz, 2H) 3.86 (s, 3H), 2.93 (m, 1H), 2.45 (s, 3H), 2.20 (s, 3H), 1.97-1.91 (m, 2H), 1.20 (d, J=7.2 Hz, 3H). MS (ES$^+$) m/z 472.2 (M+H$^+$).

Example 14

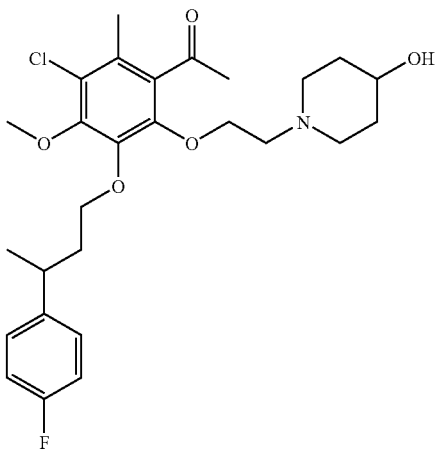

1-{3-Chloro-5-[3-(4-fluoro-phenyl)-butoxy]-6-[2-(4-hydroxy-piperidin-1-yl)-ethoxy]-4-methoxy-2-methyl-phenyl}-ethanone To a solution of N—BOC-4-hydroxypiperidine (42 mg, 0.21 mmol) in DCM (1 mL) was added TFA (1 mL) at room temperature and the solution was stirred for 0.1 h. The reaction mixture was concentrated under vacuum and dried on the high vacuum pump for 1 h. Example 8a (100 mg, 0.21 mmol) was added and the mixture was suspended in DMF. Cs$_2$CO$_3$ (123 mg, 0.38 mmol) was added in one portion and the solution was heated at 60° C. overnight. The reaction mixture was cooled to room temperature and diluted with water (20 mL) and extracted with EtOAc (3×15 mL), dried over MgSO$_4$ and concentrated under vacuum. The crude material was purified by flash chromatography (silica-gel, MeOH/DCM 1:49) yielding the title compound (51 mg, 47%) as a clear brown oil. $^1$H NMR (300 MHz, CDCl$_3$) δ 7.20-7.15 (m, 2H), 7.01-6.95 (m, 2H), 4.12 (m, 2H), 3.95 (t, J=6.6 Hz, 2H), 3.83 (s, 3H), 3.01-2.90 (m, 1H), 2.96-2.68 (m, 4H), 2.50 (s, 3H), 2.18 (s, 3H), 2.05-1.93 (m, 4H), 1.60-1.53 (m, 4H), 1.29 (d, J=6.9 Hz, 3H). MS (ES$^+$) m/z 508 (M+H$^+$).

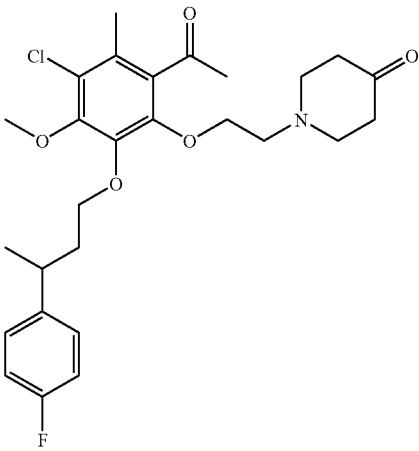

Example 15

1-{3-Chloro-5-[3-(4-fluoro-phenyl)-butoxy]-6-[2-(4-oxo-piperidin-1-yl)-ethoxy]-4-methoxy-2-methyl-phenyl}-ethanone To a solution of DMSO (24 μL, 0.34 mmol) in anhydrous DCM (0.5 mL) at −78° C. was added oxalyl chloride (14 μL, 0.17 mmol) and the reaction mixture was stirred at −78° C. for 0.5 h. Example 14 (29 mg, 0.056 mmol) in DCM (3×200 μL) was added and the reaction mixture was stirred at −78° C. for 0.75 h. Triethylamine (94 μL, 0.67 mmol) was added and the reaction mixture stirred for a further 0.5 h at −78° C. before warming to 0° C. and stirring for a further 0.5 h. The solvent was concentrated under vacuum and the crude was purified by flash chromatography (silica-gel, MeOH/DCM 1:49) to afford the title compound (29 mg, 100%) as a clear oil. $^1$H NMR (300 MHz, CDCl$_3$) δ 7.20-7.15 (m, 2H), 7.01-6.95 (m, 2H), 4.10 (t, J=5.4 Hz, 2H), 3.97 (t, J=6.9 Hz, 2H), 3.84 (s, 3H), 3.12-2.90 (m, 1H), 2.76 (t, J=6.0 Hz, 4H), 2.73 (t, J=5.7 Hz, 2H), 2.51 (s, 3H), 2.45 (t, J=6.3 Hz, 4H), 2.05-1.98 (m, 2H), 1.30 (d, J=6.9 Hz, 3H). MS (ES$^+$) m/z 506 (M+H$^+$).

Example 16

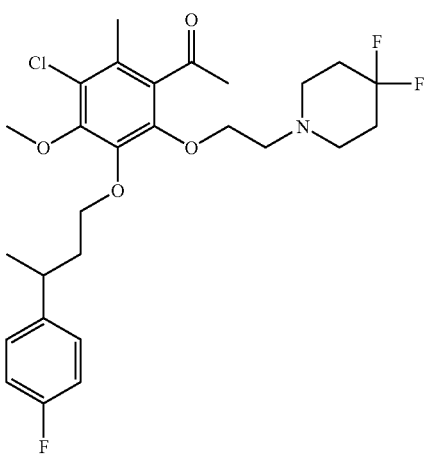

1-{3-Chloro-6-[2-(4,4-difluoro-piperidin-1-yl)-ethoxy]-5-[3-(4-fluoro-phenyl)-butoxy]-4-methoxy-2-methyl-phenyl}-ethanone Example 8a (56 mg, 0.12 mmol) was reacted with 4,4-difluoropiperidine hydrochloride (2.0 eq.) as described under General Procedure J to afford the title compound (19 mg, 31%) as a clear yellow oil. $^1$H NMR (300 MHz, CDCl$_3$) δ 7.20-7.15 (m, 2H), 7.01-6.95 (m, 2H), 4.05 (t, J=5.7 Hz, 2H), 3.97 (t, J=6.6 Hz, 2H), 3.84 (s, 3H), 3.11-2.89 (m, 1H), 2.66 (t, J=5.7 Hz, 2H), 2.58 (m, 4H), 2.49 (s, 3H), 2.18 (s, 3H), 2.05-1.92 (m, 6H), 1.30 (d, J=6.9 Hz, 3H). MS (ES$^+$) m/z 528 (M+H$^+$).

Example 17

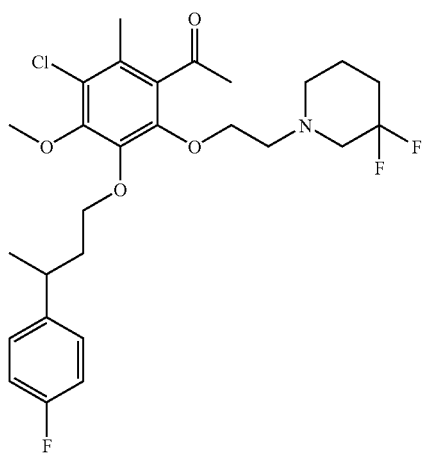

1-{3-Chloro-6-[2-(3,3-difluoro-piperidin-1-yl)-ethoxy]-5-[3-(4-fluoro-phenyl)-butoxy]-4-methoxy-2-methyl-phenyl}-ethanone Example 8a (101 mg, 0.21 mmol) was reacted with 3,3-difluoropiperidine hydrochloride (2.5 eq.) as described under General Procedure K to afford the title compound (37 mg, 33%) as a clear oil. $^1$H NMR (300 MHz, CDCl$_3$) δ 7.20-7.15 (m, 2H), 7.01-6.95 (m, 2H), 4.07 (t, J=5.4 Hz, 2H), 3.97 (td, J=6.9, 1.5 Hz, 2H), 3.83 (s, 3H), 3.05-2.83 (m, 1H), 2.75-2.68 (m, 4H), 2.50-2.46 (m, 5H), 2.18 (s, 3H), 2.13-1.94 (m, 2H), 1.90-1.74 (m, 4H), 1.29 (d, J=6.9 Hz, 3H). MS (ES$^+$) m/z 528 (M+H$^+$).

Example 18

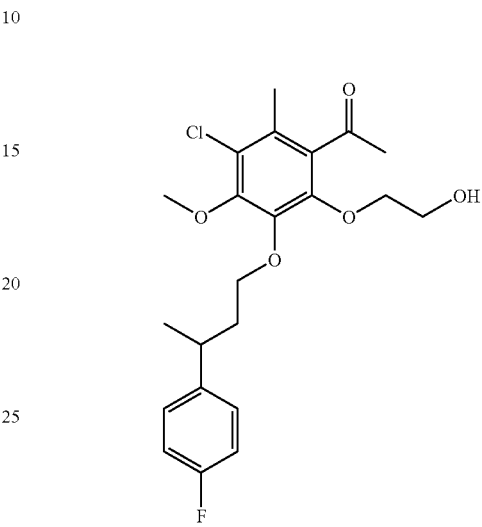

18a) 1-[3-Chloro-5-[3-(4-fluoro-phenyl)-butoxy]-6-(2-hydroxy-ethoxy)-4-methoxy-2-methyl-phenyl]-ethanone Example 7c (93 mg, 0.24 mmol) was reacted with 2-bromoethanol (1.5 eq.) as described under General Procedure F and the crude mixture was purified by flash chromatography (silica gel, Et$_2$O/hexane 70:30) to afford the title compound (68 mg, 67%) as a pale yellow oil. $^1$H NMR (300 MHz, CDCl$_3$) δ 7.19-7.15 (m, 2H), 7.01-6.95 (m, 2H), 4.13-4.11 (m, 2H), 3.95 (d, J=6.8 Hz, 2H), 3.84 (s, 3H), 3.76-3.70 (m, 2H), 3.00 (m, 1H), 2.80 (t, J=6.5 Hz, 1H), 2.50 (s, 3H), 2.20 (s, 3H), 2.06-1.98 (m, 2H), 1.29 (d, J=6.9 Hz, 3H). MS (ES$^+$) m/z 425.2 (M+H$^+$).

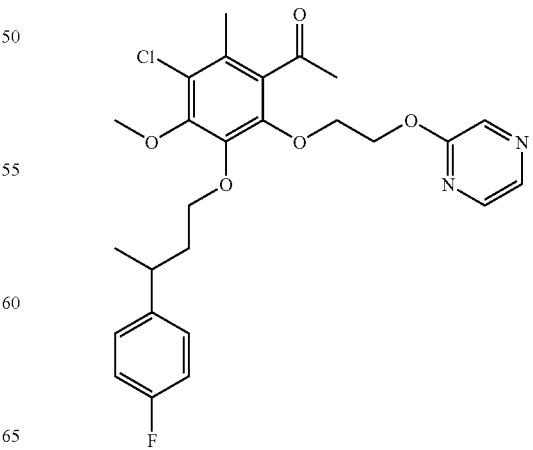

18b) 1-{3-Chloro-5-[3-(4-fluoro-phenyl)-butoxy]-4-methoxy-2-methyl-6-[2-(pyrazin-2-yloxy)-ethoxy]-phenyl}-ethanone A solution of Example 18a (43 mg, 0.10 mmol) and NaH (4 mg, 0.10 mmol) in anhydrous DMF (0.5 mL) was heated to 60° C. until $H_2$ evolution ceased (approx. 0.1 h). Chloropyrazine (11 μL, 0.12 mmol) was added dropwise and the solution heated at 100° C. overnight. The reaction mixture was cooled to room temperature, diluted with EtOAc (20 mL), washed with water (10 mL) and $NH_4Cl$ (10 mL), dried over $MgSO_4$ and concentrated under vacuum. The product was purified by flash chromatography (silica-gel, EtOAc/hexane 1:3) to afford the title compound (23 mg, 46%) as a clear, yellow oil. $^1$H NMR (300 MHz, $CDCl_3$) δ 8.23 (d, J=1.5 Hz, 1H), 8.14 (d, J=2.7 Hz, 1H), 8.06 (dd, J=3.0, 1.5 Hz, 1H), 7.26-7.14 (m, 2H), 7.00-6.94 (m, 2H), 4.54-4.51 (m, 2H), 4.35-4.32 (m, 2H), 3.96 (t, J=6.6 Hz, 1H), 3.84 (s, 3H), 3.05-2.89 (m, 1H), 2.48 (s, 3H), 2.18 (s, 3H), 2.03-1.96 (m, 2H), 1.28 (d, J=6.6 Hz, 3H). MS ($ES^+$) m/z 503 (M+H$^+$).

Example 19

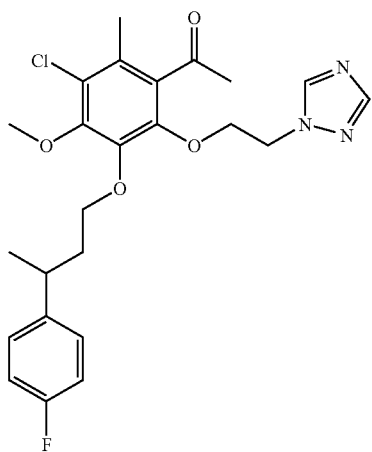

1-[3-Chloro-5-[3-(4-fluorophenyl)-butoxy]-4-methoxy-2-methyl-6-(2-[1,2,4]-triazol-1-yl-ethoxy)-phenyl]-ethanone Example 8a (85 mg, 0.17 mmol) was reacted with 1,2,4-triazole (2.5 eq.) and $CsCO_3$ (1.94 eq.) as described under General Procedure L and the crude mixture was purified by flash chromatography (silica gel, $Et_2O$) to afford the title compound as a pale yellow oil (58 mg, 72%). $^1$H NMR (300 MHz, $CDCl_3$) δ 8.12 (s, 1H), 7.95 (s, 1H), 7.17 (m, 2H), 7.01-6.95 (m, 2H), 4.39-4.36 (m, 4H), 3.83-3.78 (m, 5H), 2.91 (m, 1H), 2.32 (s, 3H), 2.16 (s, 3H), 1.94-1.89 (m, 2H), 1.27 (d, J=6.9 Hz, 3H). MS ($ES^+$) m/z 476.2 (M+H$^+$).

Example 20

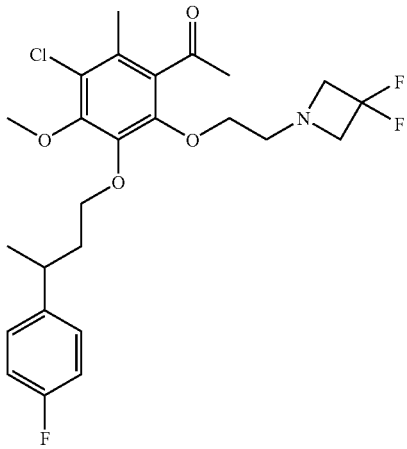

1-{3-Chloro-6-[2-(3,3-difluoro-azetidin-1-yl)-ethoxy]-5-[3-(4-fluoro-phenyl)-butoxy]-4-methoxy-2-methyl-phenyl}-ethanone Example 8a (102 mg, 0.21 mmol) was reacted with 3,3-difluoroazetidine hydrochloride (2.6 eq.) as described under General Procedure K and the crude mixture was purified by flash chromatography (silica gel, hexane/$Et_2O$ 60:40) to afford the title compound as a pale yellow oil (39 mg, 37%). $^1$H NMR (300 MHz, $CDCl_3$) δ7.20-7.17 (m, 2H), 7.01-6.95 (m, 2H), 3.98-3.91 (m, 4H), 3.83 (s, 3H), 3.62 (t, J=12.0 Hz, 4H), 2.99 (m, 1H), 2.80 (t, J=5.6 Hz, 2H), 2.50 (s, 3H), 2.18 (s, 3H), 2.07-2.01 (m, 2H), 1.30 (d J=6.9 Hz, 3H). MS ($ES^+$) m/z 500.1 (M+H$^+$).

Example 21

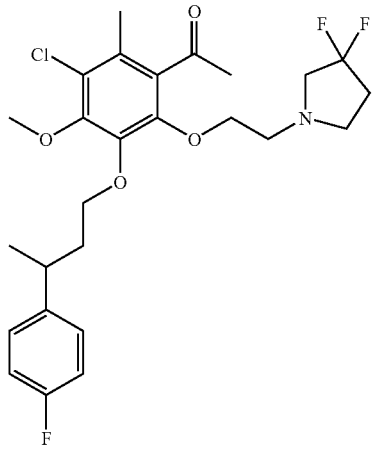

1-{3-Chloro-6-[2-(3,3-difluoro-pyrrolidin-1-yl)-ethoxy]-5-[3-(4-fluoro-phenyl)-butoxy]-4-methoxy-2-methyl-phenyl}-ethanone Example 8a (83 mg, 0.17 mmol) was reacted with 3,3-difluoropyrrolidine hydrochloride (2.5 eq.) as described under General Procedure K and the crude mixture was purified by flash chromatography (silica gel, hexane/$Et_2O$ 70:30)

to afford the title compound as a pale yellow oil (47 mg, 54%). $^1$H NMR (300 MHz, CDCl$_3$) δ 7.20-7.15 (m, 2H), 7.01-6.95 (m, 2H), 4.03 (t, J=5.6 Hz, 2H), 3.95 (dt, J=2.1, 6.8 Hz, 2H), 3.83 (s, 3H), 2.97 (m, 1H), 2.95 (t, J=13.4 Hz, 2H), 2.79-2.71 (m, 4H), 2.49 (s, 3H), 2.33-2.21 (m, 2H), 2.18 (s, 3H), 2.06-1.98 (m, 2H), 1.30 (d, J=6.9 Hz, 3H). MS (ES$^+$) m/z 514.2 (M+H$^+$).

Example 22

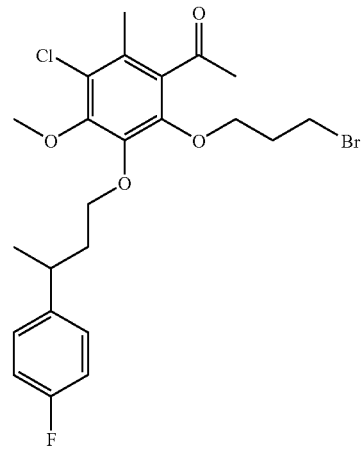

22a) 1-{2-(3-Bromo-propoxy)-5-chloro-3-[3-(4-fluoro-phenyl)-butoxy]-4-methoxy-6-methyl-phenyl}-ethanone Example 7c (179 mg, 0.47 mmol) was reacted with 1,3-dibromopropane (10.0 eq.) as described under General Procedure F to afford the title compound (641 mg, quantitative yield) as a light yellow oil. $^1$H NMR (300 MHz, CDCl$_3$) δ 7.19-7.15 (m, 2H), 7.01-6.95 (m, 2H), 4.10 (t, J=5.9 Hz, 2H), 3.94 (t, J=6.7 Hz, 2H), 3.84 (s, 3H), 3.49 (t, J=6.5 Hz, 2H), 2.99 (m, 1H), 2.46 (s, 3H), 2.17 (m, 5H), 2.07-1.99 (m, 2H), 1.30 (d, J=6.9 Hz, 3H). MS (ES$^+$) m/z 503.0 (M+H$^+$)

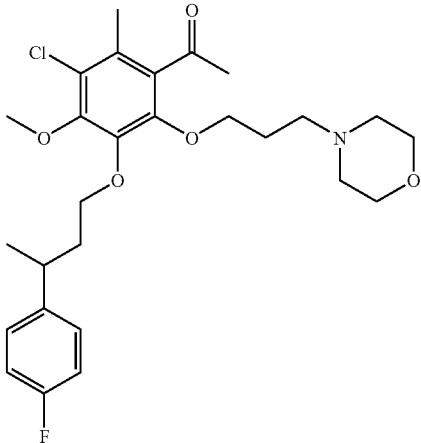

22b) 1-[3-Chloro-5-[3-(4-fluoro-phenyl)-butoxy]-4-methoxy-2-methyl-6-(3-morpholin-4-yl-propoxy)-phenyl]-ethanone Example 22a (40 mg, 0.08 mmol) was reacted with morpholine (0.2 mL, 2.29 mmol) as described under General Procedure G and the crude mixture was purified by flash chromatography (silica-gel, DCM/EtOAc/MeOH 1:0:0, 9:8:2) to afford the title compound (36 mg, 88%) as yellow/brown oil. $^1$H NMR (300 MHz, CDCl$_3$) δ 7.20-7.15 (m, 2H), 7.01-6.95 (m, 2H), 4.00 (t, J=6.4 Hz, 2H), 3.94 (t, J=6.7 Hz, 2H), 3.83 (s, 3H), 3.72-3.69 (m, 4H), 3.07-2.95 (m, 1H), 2.46 (s, 3H), 2.45-2.40 (m, 6H), 2.18 (s, 3H), 2.02-1.99 (m, 2H), 1.88-1.79 (m, 2H), 1.30 (d, J=6.9 Hz, 3H). MS (ES$^+$) m/z 508.3 (M+H$^+$)

Examples 23 and 24

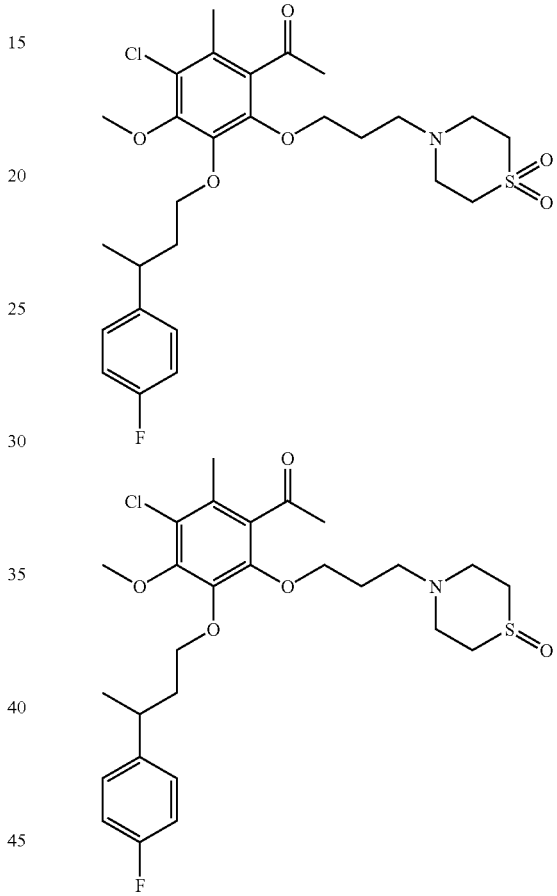

23) 1-{3-Chloro-6-[3-(1,1-dioxo-thiomorpholin-4-yl)-propoxy]-5-[3-(4-fluoro-phenyl)-butoxy]-4-methoxy-2-methyl-phenyl}-ethanone 24) 1-{3-Chloro-5-[3-(4-fluoro-phenyl)-butoxy]-4-methoxy-2-methyl-6-[3-(1-oxo-thiomorpholin-4-yl)-propoxy]-phenyl}-ethanone A solution of N—BOC-1,1-dioxothiomorpholine (85 mg, 0.365 mmol) in a mixture of DCM (1 mL) and TFA (1 mL) was stirred at room temperature for 0.1 h before concentrating under vacuum and drying the TFA salt of 1,1-dioxothiomorpholine on the high vacuum pump for 3 h. The salt was dissolved in dry DMF (1 mL) and reacted with Example 22a (92 mg, 0.18 mmol) and K$_2$CO$_3$ (2.16 eq.) under General Procedure L. The crude mixture was purified by flash chromatography (silica gel, hexane/Et$_2$O 1:4→MeOH/DCM 1:19) to afford 23 (14 mg, 14%) and 24 (13 mg, 13%) as clear colourless oils.

Example 23

¹H NMR (300 MHz, CDCl₃) δ 7.19-7.15 (m, 2H), 7.01-6.95 (m, 2H), 3.99 (t, J=6.3 Hz, 2H), 3.93 (t, J=6.9 Hz, 2H), 3.84 (s, 3H), 3.06-3.02 (m, 5H), 2.98-2.94 (m, 4H), 2.58 (t, J=6.9 Hz, 2H), 2.45 (s, 3H), 2.18 (s, 3H), 2.04-1.96 (m, 2H), 1.78 (t, J=7.5 Hz, 2H), 1.30 (d, J=6.9 Hz, 3H). MS (ES⁺) m/z 556.2 (M+H⁺).

Example 24

¹H NMR (300 MHz, CDCl₃) δ 7.19-7.15 (m, 2H), 7.01-6.95 (m, 2H), 3.99 (t, J=6.3 Hz, 2H), 3.93 (dt, J=0.9, 6.6 Hz, 2H), 3.84 (s, 3H), 3.20-2.95 (m, 2H), 2.95-2.75 (m, 4H), 2.70-2.60 (m, 2H), 2.51 (t, J=6.9 Hz, 2H), 2.46 (s, 3H), 2.17 (s, 3H), 2.04-1.95 (m, 2H), 1.81 (t, J=7.5 Hz, 2H), 1.30 (d, J=6.9 Hz, 3H). MS (ES⁺) m/z 540.2 (M+H⁺).

Example 25

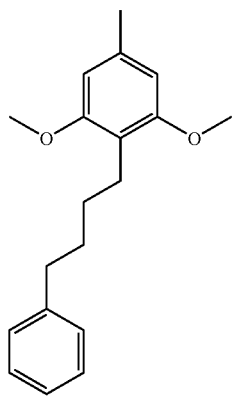

25a)
1,3-Dimethoxy-5-methyl-2-(4-phenylbutyl)benzene 3,5-Dimethoxytoluene (2.93 mL, 20 mmol) and 4-phenylbutylbromide (4.13 mL, 1.2 mmol) were reacted as described under General Procedure H and the crude product was purified by flash chromatography (silica-gel, petroleum ether/EtOAc 200:1) to afford the product as a clear oil (4.6 g, 81%). ¹H NMR (300 MHz, CDCl₃) δ 7.13-7.22 (m, 5H), 6.34 (s, 2H), 3.76 (s, 6H), 2.60-2.64 (m, 4H), 2.31 (s, 3H), 1.53-1.67 (m, 4H).

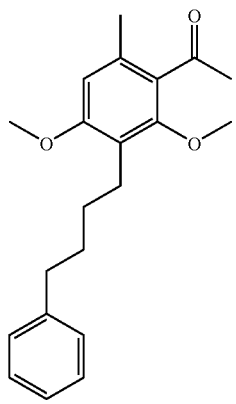

25b) 1-(2,4-dimethoxy-6-methyl-3-(4-phenylbutyl) phenyl)ethanone

Example 25a (0.500, 1.76 mmol) was reacted as described under General Procedure B to give the title compound (543 mg, 95%) as light cream oil. ¹H NMR (300 MHz, CDCl₃) δ 7.12-7.31 (m, 5H), 6.44 (s, 1H), 3.78 (s, 3H), 3.64 (s, 3H), 2.57-2.66 (m, 4H), 2.49 (s, 3H), 2.23 (s, 3H), 1.5-1.71 (m, 4H).

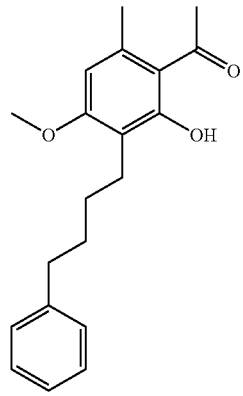

25c) 1-(2-Hydroxy-4-methoxy-6-methyl-3-(4-phenylbutyl)phenyl)ethanone

Example 25b (0.54 g, 1.65 mmol) was reacted as described under General Procedure C to give the title compound (0.51 g, 99%) as light cream oil. ¹H NMR (300 MHz, CDCl₃) δ 13.36 (s, 1H), 7.27-7.10 (m, 5H), 6.25 (s, 1H), 3.83 (s, 3H), 2.7-2.5 (m, 10H), 1.7-1.5 (m, 4H).

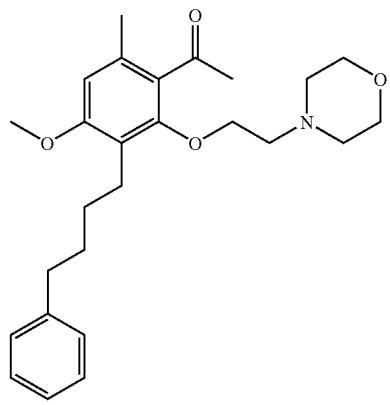

25d) 1-[4-Methoxy-6-methyl-2-(2-morpholin-4-yl-ethoxy)-3-(4-phenyl-butyl)-phenyl]-ethanone Example 25c (63 mg, 0.15 mmol) was reacted over two steps in the same manner as described for Example 1f from 1d. The title compound was afforded in 44% yield over 2 steps (36 mg). ¹H NMR (300 MHz, CDCl₃) δ 7.3-7.1 (m, 5H), 6.44

(s, 1H), 3.81-3.7 (m, 5H), 3.74-3.68 (m, 4H), 2.66-2.56 (m, 6H), 2.52 (s, 3H), 2.52-2.45 (m, 4H), 2.22 (s, 3H), 1.72-1.5 (m, 4H).

CDCl₃) δ 7.3-7.11 (m, 5H), 3.82-3.7 (m, 5H), 3.75-3.6 (m, 4H), 2.7-2.5 (m, 6H), 2.51-2.4 (m, 7H), 2.2 (s, 3H), 1.8-1.5 (m, 4H).

Example 26

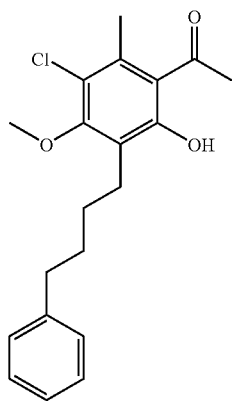

Example 27

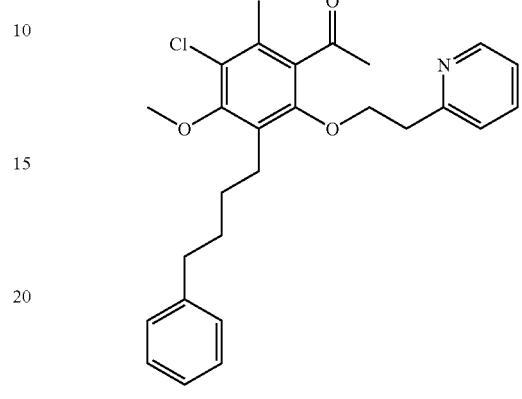

1-(3-Chloro-4-methoxy-2-methyl-5-(4-phenylbutyl)-6-(2-(pyridine-2-yl)ethoxy)phenyl)ethanone Example 26a (47 mg, 0.136 mmol) was reacted with 2-(pyridin-2-yl)ethyltrifluoromethanesulphonate (0.3 mL) according to General Procedure F to give the title compound (38 mg, 60%). ¹H NMR (300 MHz, CDCl₃) δ 8.54 (dd, 1H), 7.57 (t, 1H), 7.28-7.08 (m, 7H), 4.09 (t, J=6.3 Hz, 2H), 3.75 (s, 3H), 3.11 (t, J=6.3 Hz, 2H), 2.54 (t, J=6.9 Hz, 2H), 2.44 (t, J=6.9 Hz, 2H), 2.35 (s, 3H), 2.18 (s, 3H), 1.56-1.43 (m, 4H).

26a) 1-(3-Chloro-6-hydroxy-4-methoxy-2-methyl-5-(4-phenylbutyl)phenyl)ethanone

Example 26c (379 mg, 1.18 mmol) was reacted as described under General Procedure D to give the title compound (200 mg, 50%) as creamy solid. ¹H NMR (300 MHz, CDCl₃) δ 11.89 (s, 1H), 7.3-7.1 (m, 5H), 3.8 (s, 3H), 2.7-2.58 (m, 7H), 2.56 (s, 3H), 1.74-1.54 (m, 4H).

Example 28

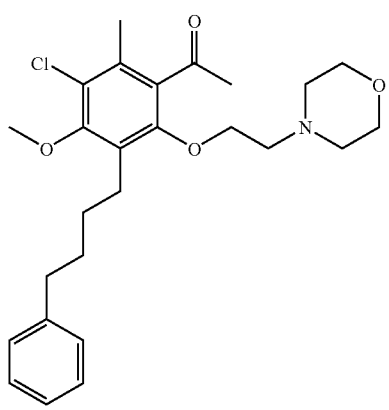

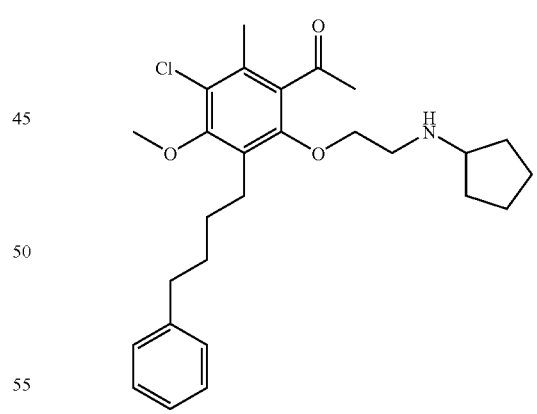

26b) 1-(3-Chloro-4-methoxy-2-methyl-6-(2-morpholinoethoxy)-5-5(4-phenyl butyl)phenyl)ethanone Example 26a (117 mg, 0.26 mmol) was reacted over two steps in the same manner as described for Example 1f from 1d. The title compound was afforded in 51% yield (79 mg) over 2 steps as a colourless syrup. ¹H NMR (300 MHz, 1-(3-Chloro-6-(2-(cyclopentylamino)ethoxy)-4-methoxy-2-methyl-5-(4-phenyl butyl)phenyl)ethanone Example 26a (64 mg, 0.14 mmol) was reacted over two steps in the same manner as described for Example 2. The title compound was afforded in 55% yield (46 mg) over 2 steps. ¹H NMR (300 MHz, CDCl₃) δ 7.28-7.11 (m, 5H), 3.81 (t, J=5.3 Hz, 2H), 3.78 (s, 3H), 3.09 (q, J=6.6 Hz, 1H), 2.84 (t, J=5.3

Hz, 2H), 2.7-2.52 (m, 4H), 2.48 (s, 3H), 2.20 (s, 3H), 1.99-1.78 (m, 3H), 1.73-1.5 (m, 8H), 1.35-1.28 (m, 2H).

Example 29

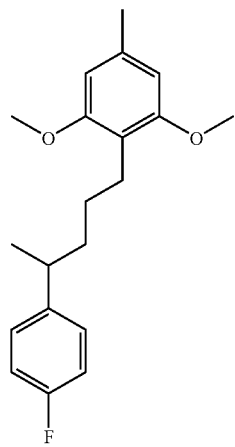

29a) 2-[4-RS-(4-Fluorophenyl)pentyl]-1,3-dimethoxy-5-methylbenzene 3,5-Dimethoxytoluene (0.25 mL, 1.70 mmol) and 4-[RS-(4-fluorophenyl)]pentylbromide (0.50 g, 2.0 mmol) were reacted as described under General Procedure H and the crude product was purified by flash chromatography (silica-gel, petroleum ether/EtOAc 250:1) to afford the product as a clear oil (0.18 g, 33%). $^1$H NMR (300 MHz, CDCl$_3$) δ 7.10-7.13 (m, 2H), 6.91-6.97 (m, 2H), 6.34 (s, 2H), 3.75 (s, 6H), 2.69-2.76 (m, 1H), 2.53-2.59 (m, 2H), 2.32 (s, 3H), 1.54-1.62 (m, 2H), 1.38-1.43 (m, 2H), 1.35 (d, J=8.1 Hz, 3H).

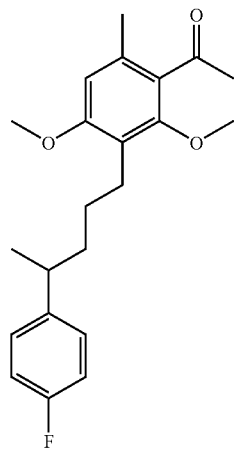

29b) 1-(3-(4-RS-(4-Fluorophenyl)pentyl)-2,4-dimethoxy-6-methylphenyl)ethanone Example 29a (166 mg, 0.56 mmol) was reacted as described under General Procedure B to give the title compound in 95% yield (189 mg). $^1$H NMR (300 MHz, CDCl$_3$) δ 7.13-7.08 (m, 2H), 6.97-6.8 (m, 2H), 6.42 (s, 1H), 3.74 (s, 3H), 3.59 (m, 5H), 2.21 (s, 3H), 1.65-1.43 (m, 2H), 1.41-1.32 (m, 2H), 1.19 (d, J=7 Hz, 3H).

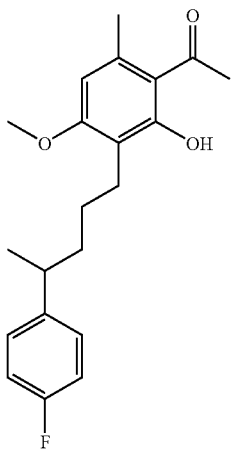

29c) 1-(3-(4-(4-Fluorophenyl)pentyl)-2-hydroxy-4-methoxy-6-methylphenyl)ethanone Example 29b (189 mg, 0.56 mmol) was reacted as described under General Procedure B to give the title compound in 98% yield (178 mg). $^1$H NMR (300 MHz, CDCl$_3$) δ 7.13-7.09 (m, 2H), 7.08-6.8 (m, 2H), 6.23 (s, 1H), 3.8 (s, 3H), 3.59 (m, 3H), 2.69 (q, J=7.0 Hz, 1H), 2.6 (s, 3H), 2.56 (s, 3H), 1.61-1.5 (m, 2H), 1.5-1.2 (m, 2H), 1.18 (d, J=7 Hz, 3H).

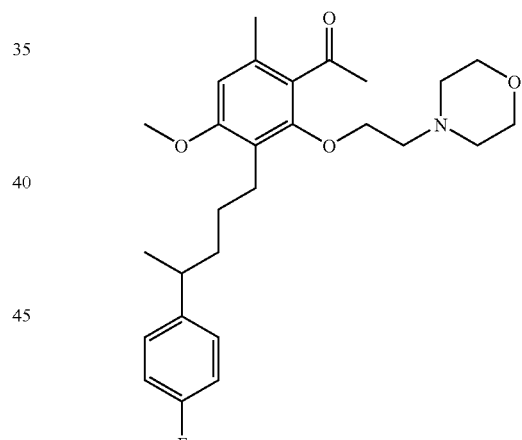

29d) 1-{4-Methoxy-6-methyl-2-(2-morpholinoethoxy)-3-[4-RS-(4-fluorophenyl)pentyl)]phenyl}ethanone Example 29c (14 mg, 0.04 mmol) was reacted with 4-(2-chloroethyl)-morpholine hydrochloride (9 mg, 0.05 mmol) as described under General Procedure I and the crude product was purified by flash chromatography (silica-gel, DCM/EtOAc/MeOH 100:0:0, 90:8:2) to afford the title compound (5 mg, 26%) as a colourless oil. $^1$H NMR (300 MHz, CDCl$_3$) δ 7.09-7.13 (m, 2H), 6.91-6.99 (m, 2H), 6.43 (s, 1H), 3.73-

3.77 (m, 9H), 2.69-2.76 (m, 1H), 2.50-2.62 (m, 11H), 2.21 (s, 3H), 1.55-1.64 (m, 2H), 1.45-1.51 (m, 2H), 1.23 (d, J=8.1 Hz, 3H).

Example 30

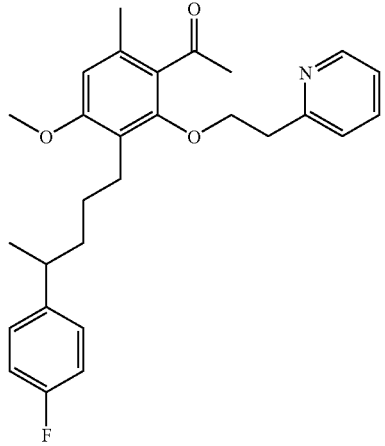

1-[3-[4-RS-(4-Fluorophenyl)pentyl]-4-methoxy-6-methyl-2-(2-pyridin-2-yl-ethoxy)phenyl]ethanone Example 29c was reacted with 2-(pyridin-2-yl)ethyltrifluoromethanesulphonate according to General Procedure F a to give the title compound (22%). $^1$H NMR (300 MHz, CDCl$_3$) δ 8.55 (d, 1H), 7.60 (t, 1H), 6.91-7.26 (m, 6H), 6.41 (s, 1H), 4.05 (t, J=6.3 Hz, 2H), 3.73 (s, 3H), 3.14 (t, J=6.3 Hz, 2H), 2.59-2.68 (m, 2H), 2.34-2.41 (m, 4H), 2.20 (s, 3H), 1.15-1.58 (m, 7H). MS (ES$^+$) m/z 450.1 (M+H$^+$).

Example 31

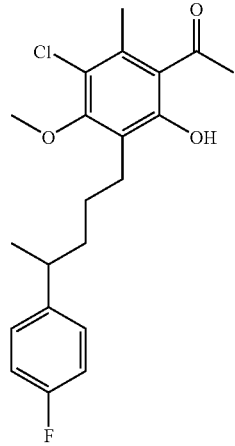

31a) 1-(3-Chloro-5-(4-(4-fluorophenyl)pentyl)-6-hydroxy-4-methoxy-2-methylphenyl)ethanone Example 29c was reacted as described under General Procedure D to give the title compound in 47% yield. $^1$H NMR (300 MHz, CDCl$_3$) δ 11.85 (s, 1H), 7.13-7.07 (m, 2H), 6.96-6.89 (m, 2H), 2.71 (q, J=7.1 Hz, 1H), 2.5-2.62 (m, 5H), 2.54 (s, 3H), 1.65-1.53 (m, 2H), 1.48-1.35 (m, 2H), 1.19 (d, 3H).

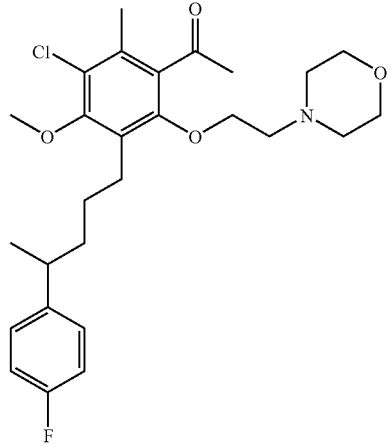

31b) 1-(3-Chloro-5-(4-(4-fluorophenyl)pentyl)-4-methoxy-2-methyl-6-(2-morpholino ethoxy)phenyl) ethanone Example 31a was reacted over two steps in the same manner as described for Example 1f from 1d. The title compound was afforded in 35% yield over 2 steps. $^1$H NMR (300 MHz, CDCl$_3$) δ 7.13-7.08 (m, 2H), 6.96-6.9 (m, 2H), 3.78-3.69 (m, 7H), 2.7 (q, J=7 Hz, 1H), 2.6-2.53 (m, 4H), 2.5-2.45 (m, 5H), 2.19 (s, 3H), 1.6-1.19 (m, 7H).

Example 32

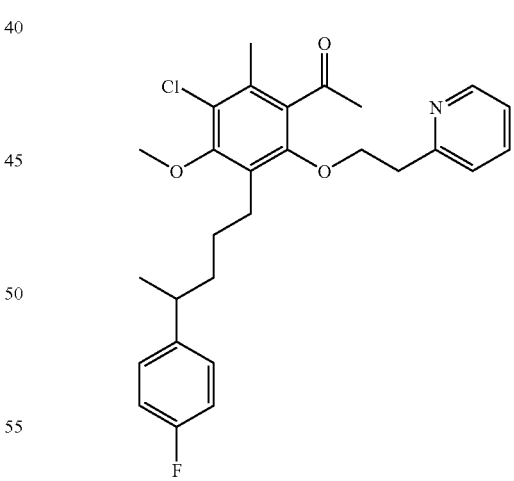

1-[3-Chloro-5-[4-(4-fluoro-phenyl)-pentyl]-4-methoxy-2-methyl-6-(2-pyridin-2-yl-ethoxy)-phenyl]-ethanone Example 31a was reacted with 2-(pyridin-2-yl)ethyltrifluoromethanesulphonate according to General Procedure F to give the title compound (40%). $^1$H NMR (300 MHz, CDCl$_3$) δ 8.53 (d, J=4.4 Hz, 1H), 7.58 (dt, J=1.8, 7.7 Hz, 1H), 7.04-

7.18 (m, 4H), 6.80-6.95 (m, 2H), 4.05 (t, J=6.3 Hz, 2H), 3.70 (s, 3H), 3.09 (t, J=6.3 Hz, 2H), 2.57 (m, 1H), 2.32-2.44 (m, 2H), 2.29 (s, 3H), 2.17 (s, 3H), 1.18-1.49 (m, 4H) 1.15 (d, 3H).

2.81 (t, J=7.3 Hz, 2H), 2.62 (t, J=5.7 Hz, 2H), 2.52 (s, 3H), 2.47-2.44 (m, 4H), 2.20 (s, 3H), 2.09-2.00 (m, 2H). MS (ES+) m/z 428.0 (M+H+).

Example 34

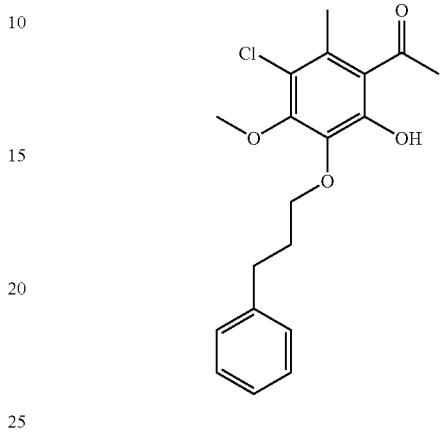

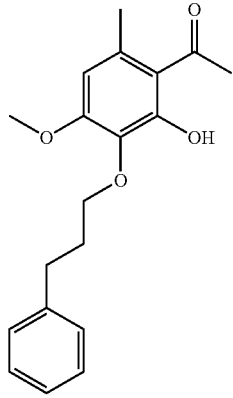

Example 33

33a) 1-(3-(3-(phenyl)propoxy)-2-hydroxy-4-methoxy-6-methylphenyl)ethanone

Prepared by a similar method used to prepare Example 1c except 1-(3-bromopropyl)benzene was used in place of 1-(3-bromopropyl)-4-fluorobenzene.

34a) 1-[3-Chloro-6-hydroxy-4-methoxy-2-methyl-5-(3-phenyl-propoxy)-phenyl]-ethanone Example 33a was reacted as described under General Procedure D to give the title compound in 33% yield. $^1$H NMR (300 MHz, CDCl$_3$) δ 7.33 (m, 5H), 4.10 (t, J=6.5 Hz, 2H), 3.92 (s, 3H), 2.82 (t, J=7.7 Hz, 2H), 2.58 (s, 3H), 2.38 (s, 3H), 2.12-2.07 (m, 2H). MS (ES+) m/z 349.2 (M+H+).

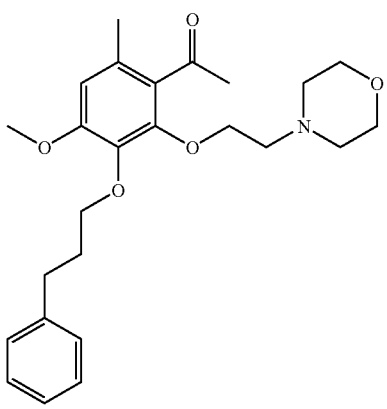

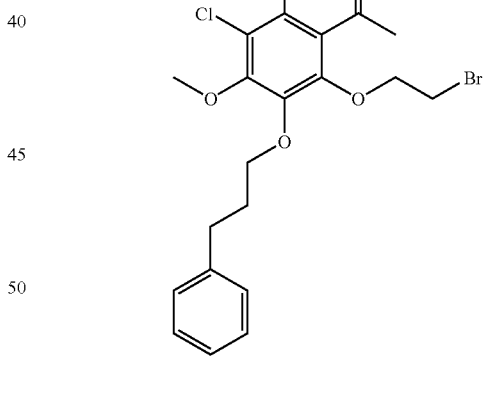

33b) 1-[4-Methoxy-6-methyl-2-(2-morpholin-4-yl-ethoxy)-3-(3-phenyl-propoxy)-phenyl]-ethanone Example 33b was prepared in a using a similar method as used in the conversion from 1d to 1f. $^1$H NMR (300 MHz, CDCl$_3$) δ 7.30-7.15 (m, 5H), 6.47 (s, 1H), 4.12 (t, J=5.7 Hz, 2H), 4.01 (t, J=6.4 Hz, 2H), 3.82 (s, 3H), 3.69-3.66 (m, 4H),

34b) 1-[2-(2-Bromo-ethoxy)-5-chloro-4-methoxy-6-methyl-3-(3-phenyl-propoxy)-phenyl]-ethanone Example 34a (4.3 g, 17 mmol) was reacted with 1,2-dibromoethane (40 mL) as described under General Procedure F to afford the title compound (5.5 g, 100%) as a red oil. $^1$H NMR (300 MHz, CDCl$_3$) δ 7.33-7.18 (m, 5H), 4.30 (t, J=6.3 Hz, 2H), 4.09 (t, J=6.3 Hz, 2H), 3.89 (s, 3H), 3.51 (t, J=6.0 Hz, 2H), 2.83 (t, J=8.1 Hz, 2H), 2.52 (s, 3H), 2.20 (s, 3H), 2.14-2.05 (m, 2H). MS (ES+) m/z 457 (M+H+).

61

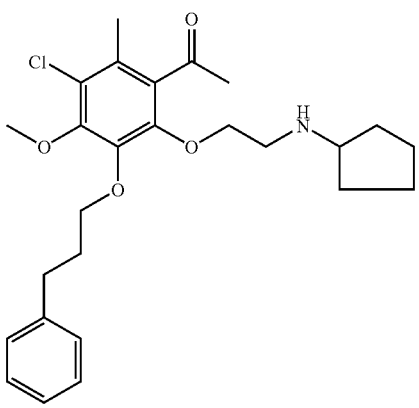

34c) 1-[3-Chloro-6-(2-cyclopentylamino-ethoxy)-4-methoxy-2-methyl-5-(3-phenyl-propoxy)-phenyl]-ethanone Example 34b (217 mg, 0.48 mmol) was reacted with cyclopentylamine as described under General Procedure B (except heated to 65° C.) and the crude was purified by flash chromatography (silica-gel, MeOH/DCM 5:95) yielding the title compound (151 mg, 68%) as an oil. $^1$H NMR (300 MHz, CDCl$_3$) δ 7.32-7.19 (m, 5H), 4.14 (t, J=5.1 Hz, 2H), 4.07 (t, J=6.3 Hz, 2H), 3.88 (s, 3H), 3.24-3.04 (m, 1H), 2.87-2.79 (m, 4H), 2.49 (s, 3H), 2.19 (s, 3H), 2.10-2.04 (m, 2H), 1.85-1.78 (m, 3H), 1.69-1.66 (m, 2H), 1.56-1.51 (m, 2H), 1.35-1.31 (m, 2H). MS (ES$^+$) m/z 460 (M+H$^+$).

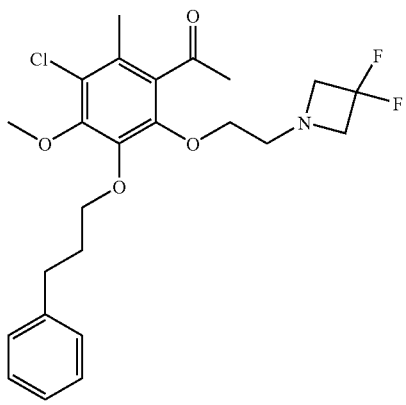

Example 35

1-[3-Chloro-6-[2-(3,3-difluoro-azetidin-1-yl)-ethoxy]-4-methoxy-2-methyl-5-(3-phenyl-propoxy)-phenyl]-ethanone Example 34b (105 mg, 0.23 mmol) was reacted with 3,3-difluoroazetidine hydrochloride (2.0 eq.) as described under General Procedure J and the crude mixture was purified by flash chromatography (silica gel, hexane/Et$_2$O 70:30) to afford the title compound (21 mg, 20%) as a light orange oil. $^1$H NMR (300 MHz, CDCl$_3$) δ 7.33-7.20 (m, 5H), 4.07 (t, J=6.5 Hz, 2H), 4.01 (t, J=5.6 Hz, 2H), 3.88 (s, 3H), 3.63 (t, J=12.0 Hz, 4H), 2.85-2.80 (m, 4H), 2.51 (s, 3H), 2.20 (s, 3H), 2.12-2.06 (m, 2H). MS (ES$^+$) m/z 468.2 (M+H$^+$).

Example 36

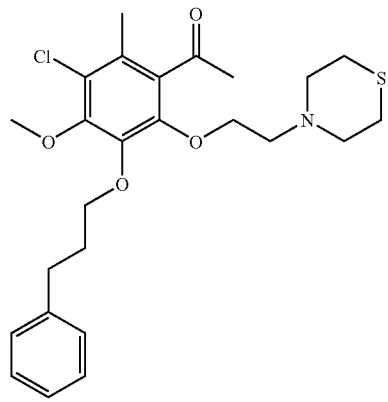

1-[3-Chloro-4-methoxy-2-methyl-5-(3-phenyl-propoxy)-6-(2-thiomorpholin-4-yl-ethoxy)-phenyl]-ethanone Example 34b (201 mg, 0.44 mmol) and thiomorpholine were reacted as described under the General Procedure B (except heated to 65° C.) and the crude was purified by flash chromatography (silica-gel, EtOAc/hexane 1:4) yielding the title compound (166 mg, 79%) as an oil. $^1$H NMR (300 MHz, CDCl$_3$) δ 7.33-7.02 (m, 5H), 4.13-4.06 (m, 4H); 3.88 (s, 3H); 2.82 (dd, J=9.3, 7.5 Hz, 2H); 2.76-2.73 (m, 4H); 2.68-2.64 (m, 6H); 2.52 (s, 3H); 2.20 (s, 3H), 2.13-2.03 (m, 2H). MS (ES$^+$) m/z 478 (M+H$^+$).

Example 37

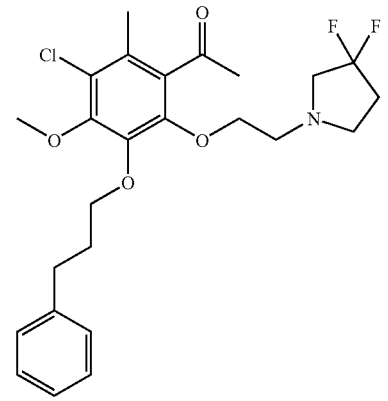

1-[3-Chloro-6-[2-(3,3-difluoro-pyrrolidin-1-yl)-ethoxy]-4-methoxy-2-methyl-5-(3-phenyl-propoxy)-phenyl]-ethanone Example 34b (58 mg, 0.13 mmol) and 3,3-difluoropyrrolidine hydrochloride (2.5 eq.) were reacted as described under General Procedure J and the crude product was purified by flash chromatography (silica gel, hexane/Et₂O 70:30) to afford the title compound as a pale yellow oil (10 mg, 16%). ¹H NMR (300 MHz, CDCl₃) δ 7.33-7.18 (m, 5H), 4.08 (t, J=6.2 Hz, 4H), 3.88 (s, 3H), 2.96 (t, J=13.4 Hz, 2H), 2.85-2.73 (m, 6H), 2.51 (s, 3H), 2.31-2.13 (m, 2H), 2.20-2.04 (m, 2H). MS (ES⁺) m/z 482.1 (M+H⁺).

Example 38

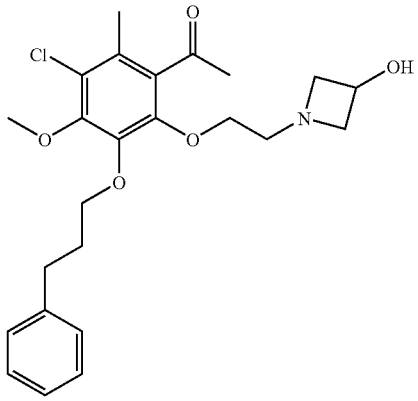

1-[3-Chloro-6-[2-(3-hydroxy-azetidin-1-yl)-ethoxy]-4-methoxy-2-methyl-5-(3-phenyl-propoxy)-phenyl]-ethanone Example 34b (207 mg, 0.46 mmol), CsCO₃ (2.48 eq.) and 3-hydroxyazetidine hydrochloride (1.4 eq.) were reacted as described under General Procedure L and the crude product was purified by flash chromatography (silica gel, hexane/Et₂O 1:1) to afford the title compound as a pale yellow oil (34 mg, 16%). ¹H NMR (300 MHz, CDCl₃) δ 7.33-7.20 (m, 5H), 4.40 (quintet, J=5.7 Hz, 1H), 4.07 (t, J=6.5 Hz, 2H), 3.98 (t, J=5.7 Hz, 2H), 3.88 (s, 3H), 3.67-3.62 (m, 2H), 2.96-2.91 (m, 2H), 2.85-2.80 (m, 2H), 2.73 (t, J=5.7 Hz, 2H), 2.51 (s, 3H), 2.19 (s, 3H), 2.13-2.03 (m, 2H). MS (ES⁺) m/z 448.2 (M+H⁺).

Example 39

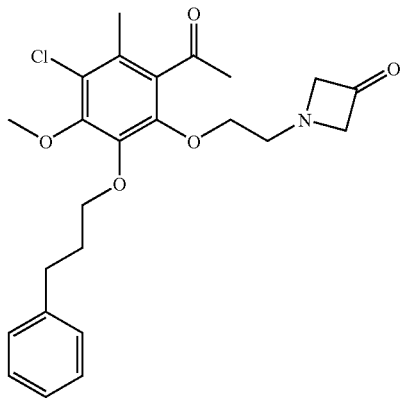

1-[3-Chloro-6-[2-(3-oxo-azetidin-1-yl)-ethoxy]-4-methoxy-2-methyl-5-(3-phenyl-propoxy)-phenyl]-ethanone Oxalyl chloride (14 μL, 0.17 mmol) was added to a solution of DMSO (22 μL, 0.31 mmol) in anhydrous DCM (0.5 mL) at −78° C. was added and the reaction mixture was stirred at −78° C. for 0.5 h. Example 38 (25 mg, 0.05 mmol) in DCM (3×200 μL) was added and the reaction mixture was stirred at −78° C. for 0.75 h. Triethylamine (84 μL, 0.60 mmol) was added and the reaction mixture stirred for a further 0.5 h at −78° C. before warming to 0° C. and stirring for a further 0.5 h. The solvent was concentrated under vacuum and the crude was purified by flash chromatography (silica gel, Et₂O) to afford the title compound (13 mg, 59%) as a pale yellow oil. ¹H NMR (300 MHz, CDCl₃) δ 7.30-7.20 (m, 5H), 4.13 (s, 4H), 4.10 (t, J=6.0 Hz, 4H), 3.88 (s, 3H), 2.98 (t, J=5.6 Hz, 2H), 2.85-2.80 (m, 2H), 2.51 (s, 3H), 2.20 (s, 3H), 2.12-2.07 (m, 2H). MS (ES⁺) m/z 446.3 (M+H⁺).

Example 40

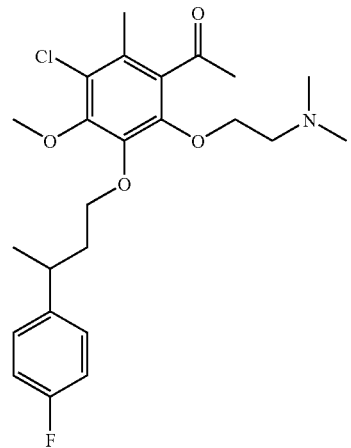

1-{3-Chloro-6-(2-dimethylamino-ethoxy)-5-[3-(4-fluoro-phenyl)-butoxy]-4-methoxy-2-methyl-phenyl}-ethanone Example 8a (50 mg, 0.10 mmol) was reacted with 1.0 M solution of dimethylamine in THF (1 mL, 1 mmol) at 55° C. at for 24 h. The solvent was removed under vacuum and the crude mixture was suspended in Et₂O (910 mL) and 2N HCl (10 mL). The ethereal layer was separated, dried over MgSO₄ and evaporated to dryness. The isolated white solid was again suspended in mixture of Et₂O and hexane (1/9) sonicated for 1 minute and solid was filtered and dried. The isolated solid was suspended in DCM and washed with NaHCO₃ (aq) solution. The organic layer was dried over MgSO₄ and evaporated to dryness to afford the title compound as a pale yellow oil (26 mg, 56%). ¹H NMR (300 MHz, CDCl₃) δ 7.20-7.15 (m, 2H), 7.00-6.95 (m, 2H), 4.05 (t, J=6.0 Hz, 2H), 3.96 (t, J=6.6 Hz, 2H), 3.82 (s, 3H), 3.03-2.96 (m, 1H), 2.57 (t, J=6.0 Hz, 2H), 2.49 (s, 3H), 2.27 (s, 6H), 2.18 (s, 3H), 2.03-1.98 (m, 2H), 1.29 (d, J=6.9 Hz, 3H). MS (ES$^+$) m/z 452.2.2 (M+H$^+$).

Example 41

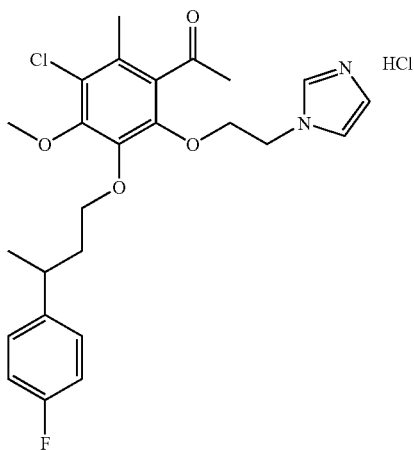

1-[3-Chloro-5-[3-(4-fluoro-phenyl)-butoxy]-6-(2-imidazol-1-yl-ethoxy)-4-methoxy-2-methyl-phenyl]-ethanone Example 8a (50 mg, 0.10 mmol) was reacted with imidazole (8.0 eq.) as described under General Procedure G and the crude mixture was dissolved in DCM and HCl gas was bubbled through it for 3 minutes. Then, solvent was removed under vacuum and the residue was suspended in dry ether and triturated to afford the title compound as a off-white solid (22 mg, 45%). $^1$H NMR (300 MHz, CDCl$_3$) δ 9.57 (bs, 1H), 7.33 (bs, 1H) 7.19-7.14 (m, 3H), 7.02-6.96 (m, 2H), 4.60 (bs, 2H), 4.37 (bs, 2H), 3.89-3.76 (m, 5H), 2.88-2.93 (m, 1H), 2.32 (s, 3H), 2.16 (s, 3H), 1.94-1.96 (m, 2H), 1.27 (d, J=6.6 Hz, 3H). MS (ES$^+$) m/z 475.2 (M+H$^+$).

Example 42

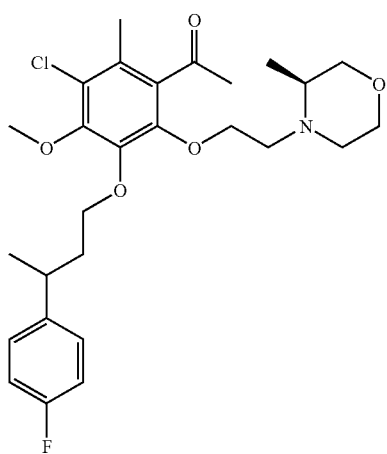

1-{3-Chloro-5-[3-(4-fluoro-phenyl)-butoxy]-4-methoxy-2-methyl-6-[2-((S)-3-methyl-morpholin-4-yl)-ethoxy]-phenyl}-ethanone Example 8a (74 mg, 0.16 mmol) was reacted with (S)-3-methylmorpholine (3.0 eq.) as described under General Procedure G and the crude mixture was purified by flash chromatography (silica gel, hexane/Et$_2$O 1:4) to afford the title compound as a pale yellow oil (51 mg, 65%). $^1$H NMR (300 MHz, CDCl$_3$) δ 7.20-7.15 (m, 2H), 7.01-6.95 (m, 2H), 4.05 (t, J=6.0 Hz, 2H), 3.95 (t, J=6.6 Hz, 2H), 3.83 (s, 3H), 3.79-3.57 (m, 4H), 3.22 (dd, J=8.7, 11.1 Hz, 1H), 3.12-2.88 (m, 2H), 2.74 (m, 1H), 2.55-2.35 (m, 6H), 2.18 (s, 3H), 2.07-1.96 (m, 2H), 1.29 (d, J=6.9 Hz, 3H), 0.96 (d, J=6.0 Hz, 3H). MS (ES$^+$) m/z 508.2 (M+H$^+$).

Biological Data

Potency of compounds to inhibit the human Kv1.3 ion channel was determined as follows:

EC$_{50}$ values for inhibition of Kv1.3 currents were determined by the method according to Schmitz et al (2005) Molecular Pharmacology 68, 1254-1270 with the following differences:

1. Human Jurkat cells (which endogenously express hKv1.3) or Chinese Hamster Ovary (CHO) cells stably transfected with hKv1.3 were used in place of transfected rat L929 cells.
2. All electrophysiology was performed using planar patch clamp (Port-A-Patch, Nanion Technologies Gmbh, Munich) in contrast to conventional patch clamp.
3. EC50 values shown were determined from averaged dose response data obtained from 3 or more cells.

TABLE 1

| Example Numbers | Structure | EC$_{50}$ Kv1.3 |
|---|---|---|
| 2 | 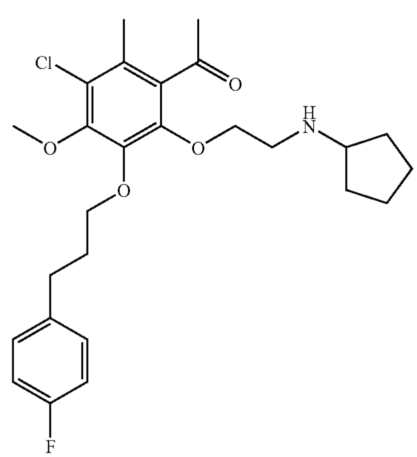 | <50 nM |

TABLE 1-continued
| Example Numbers | Structure | EC$_{50}$ Kv1.3 |
|---|---|---|
| 4f | 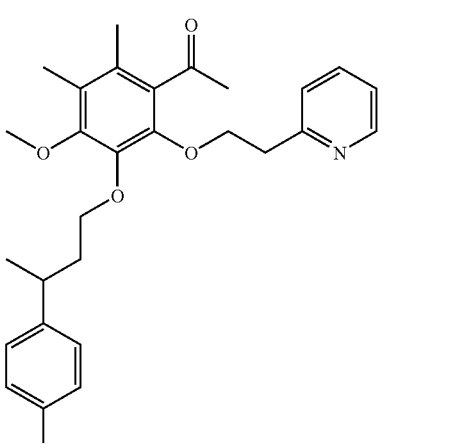 | <50 nM |
| 5 | 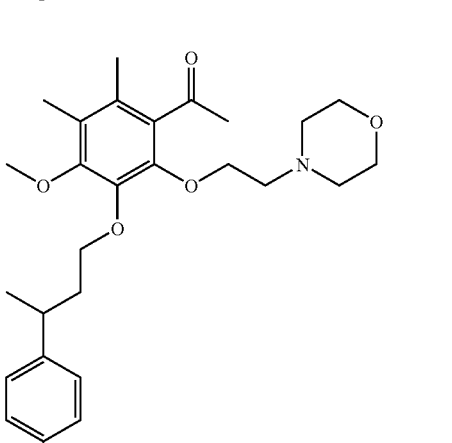 | <50 nM |
| 6 | 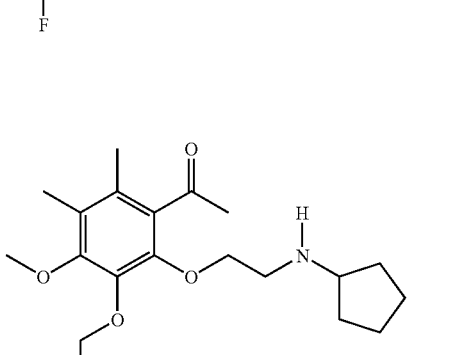 | <50 nM |
| 7d | 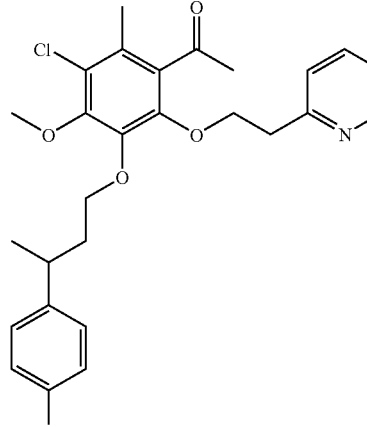 | <50 nM |
| 8b | 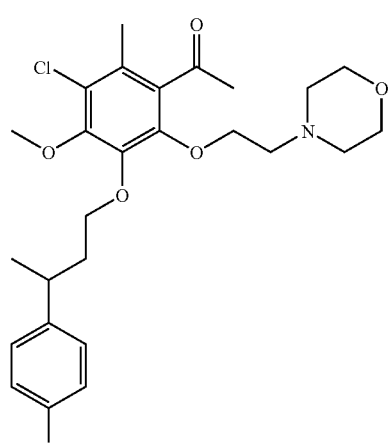 | <50 nM |
| 10 | 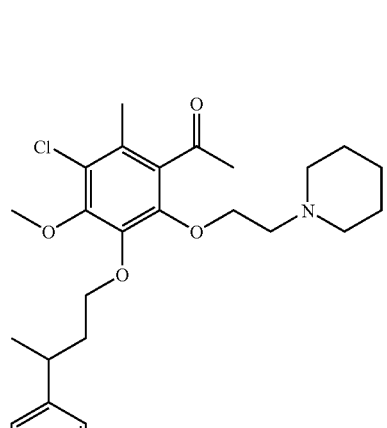 | <50 nM |

TABLE 1-continued

| Example Numbers | Structure | EC$_{50}$ Kv1.3 |
|---|---|---|
| 12 | 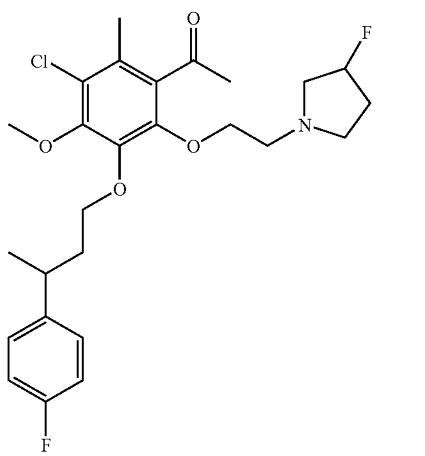 | <50 nM |
| 15 | 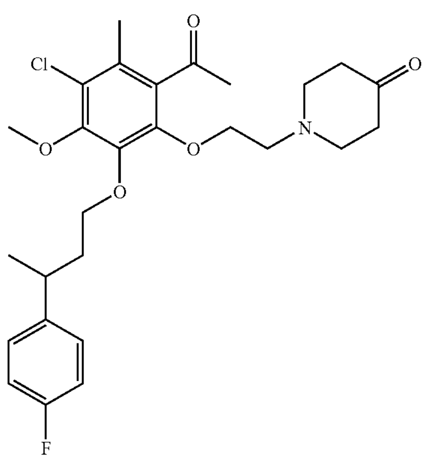 | <50 nM |
| 17 | 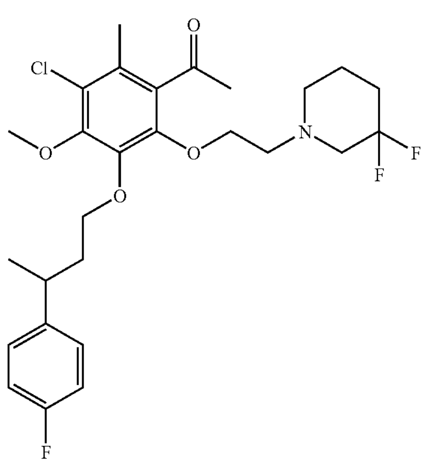 | <50 nM |
| 18b | | <50 nM |
| 22b | | <50 nM |
| 23 | | <50 nM |

TABLE 1-continued

| Example Numbers | Structure | EC$_{50}$ Kv1.3 |
|---|---|---|
| 26b | 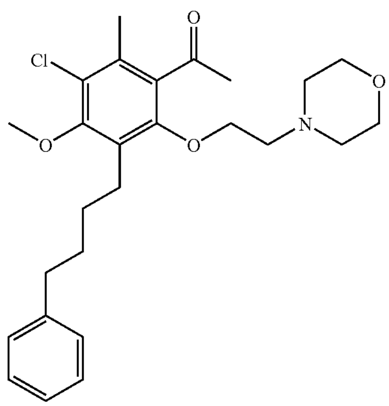 | <50 nM |
| 27 | 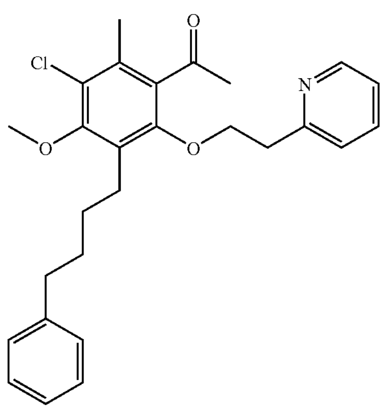 | <50 nM |
| 32 | 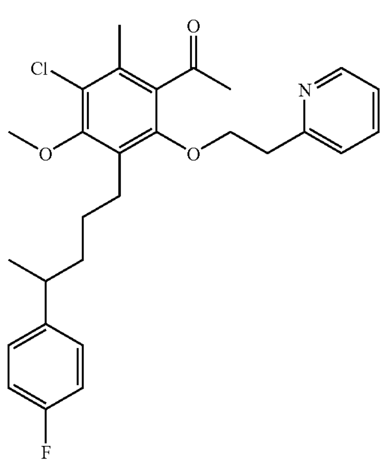 | <50 nM |
| 41 | 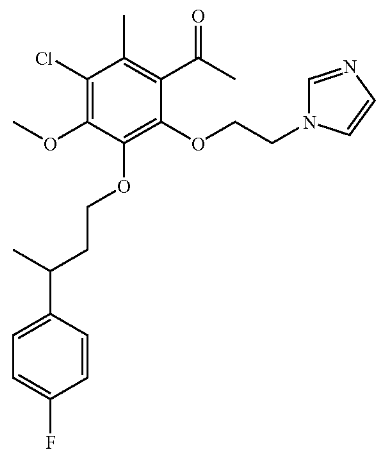 | <50 nM HCl |
| 1f | 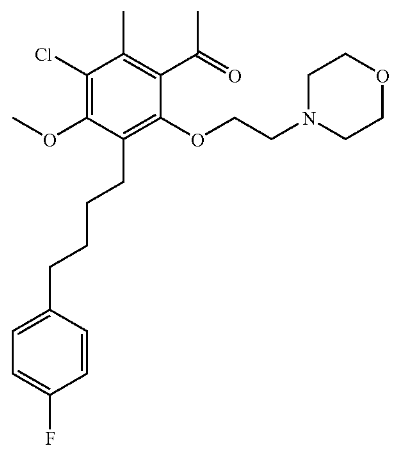 | 50-150 nM |
| 3c | 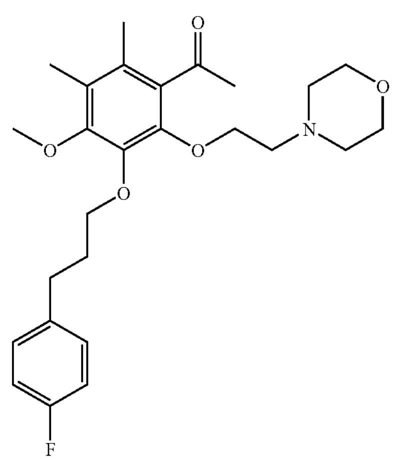 | 50-150 nM |

TABLE 1-continued

| Example Numbers | Structure | EC$_{50}$ Kv1.3 |
|---|---|---|
| 9 | 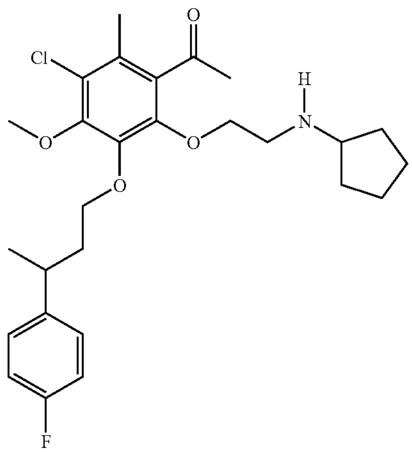 | 50-150 nM |
| 11 | 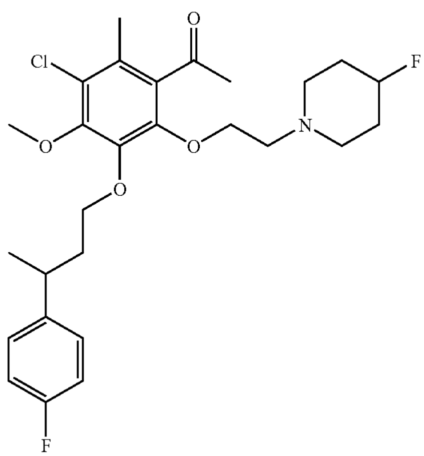 | 50-150 nM |
| 14 | 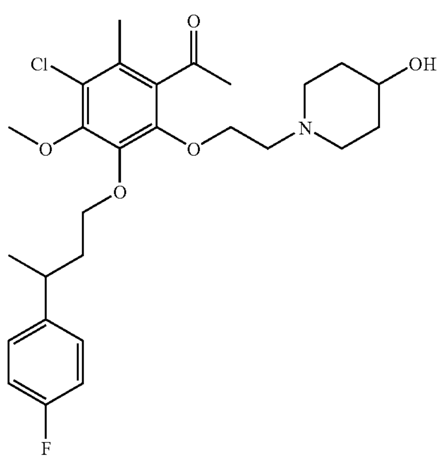 | 50-150 nM |
| 16 | 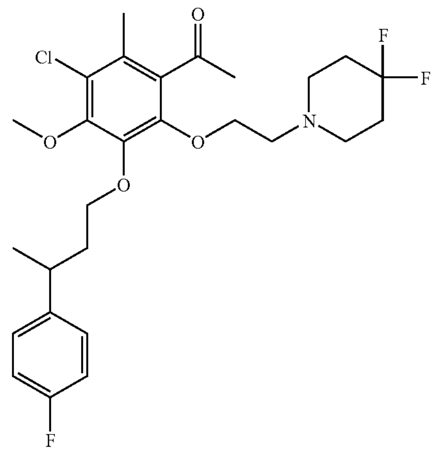 | 50-150 nM |
| 19 | 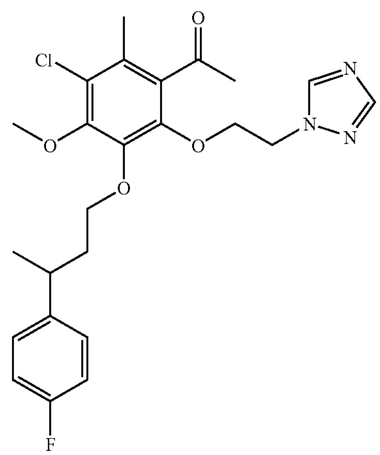 | 50-150 nM |
| 20 | 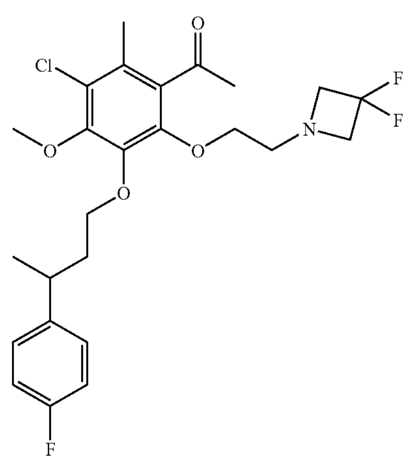 | 50-150 nM |

TABLE 1-continued
| Example Numbers | Structure | EC$_{50}$ Kv1.3 |
|---|---|---|
| 24 | 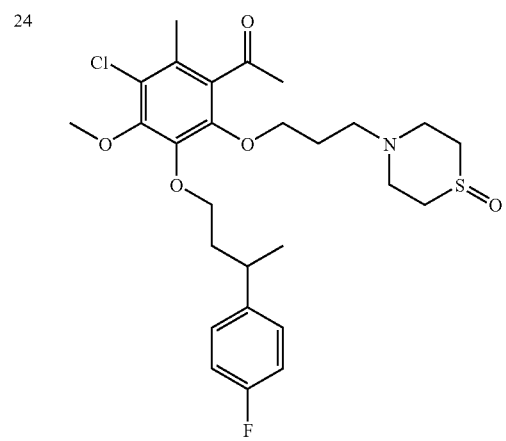 | 50-150 nM |
| 31b | 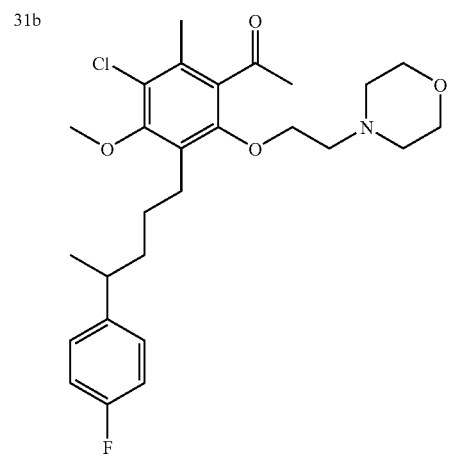 | 50-150 nM |
| 34c | 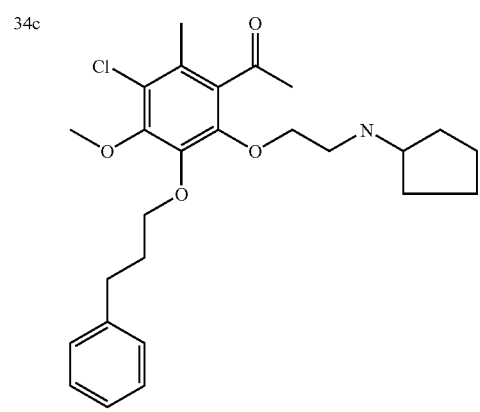 | 50-150 nM |
| 36 | 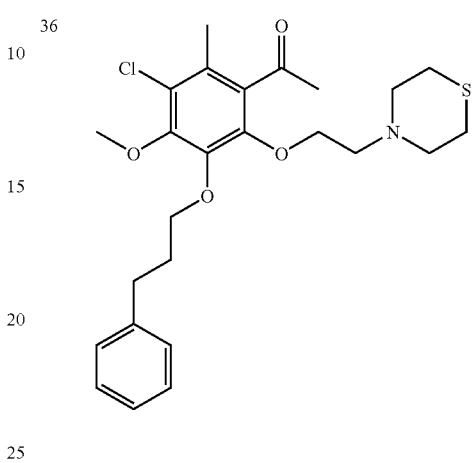 | 50-150 nM |
| 40 | 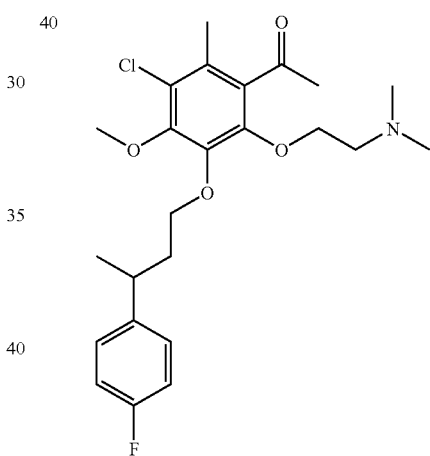 | 50-150 nM |
| 42 | 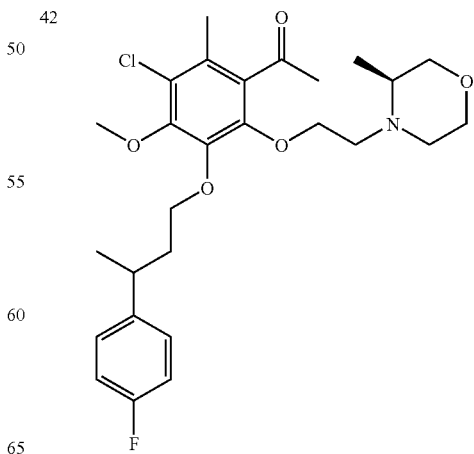 | 50-150 nM |

TABLE 1-continued
| Example Numbers | Structure | EC$_{50}$ Kv1.3 |
|---|---|---|
| comparator | 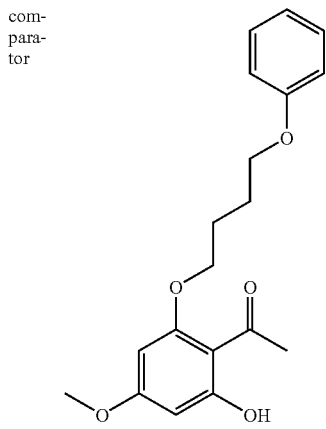 | 150-300 nM |
| 13 | 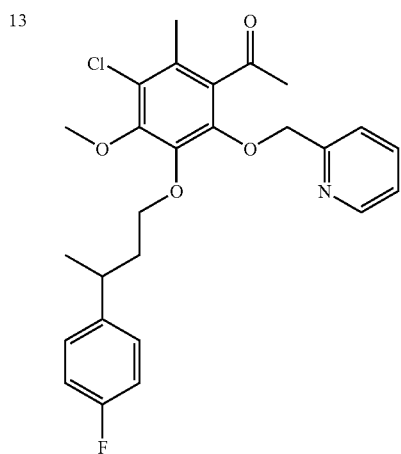 | 150-300 nM |
| 33b | 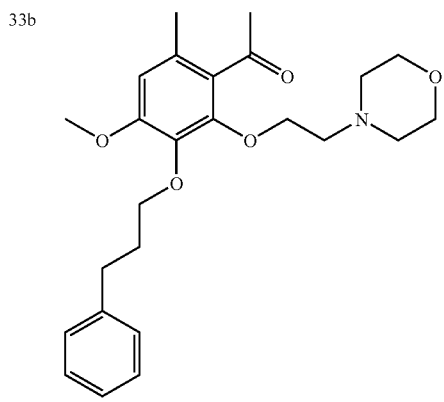 | 150-300 nM |
| 37 | 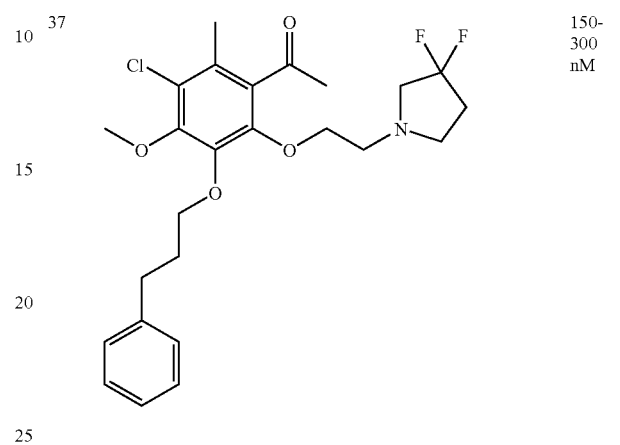 | 150-300 nM |
| 35 | 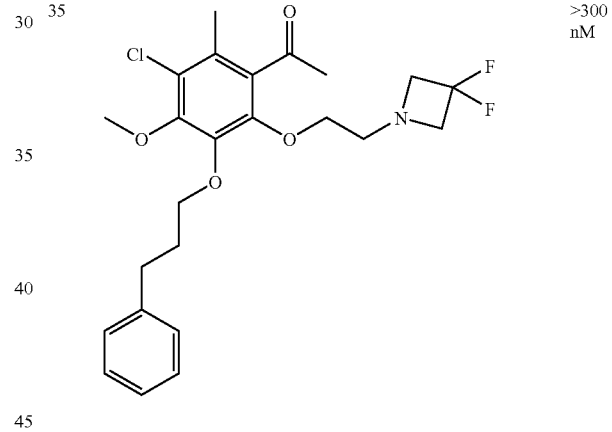 | >300 nM |
| 38 | 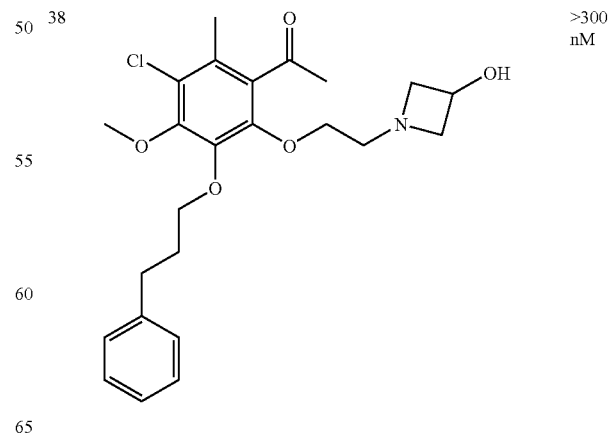 | >300 nM |

TABLE 1-continued
| Example Numbers | Structure | EC$_{50}$ Kv1.3 |
|---|---|---|
| 39 | 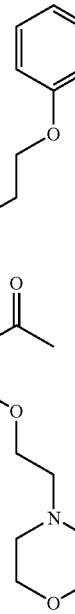 | >300 nM |
| comparator | | >300 nM |
| comparator | | >300 nM |
| comparator | | >300 nM |
| comparator | 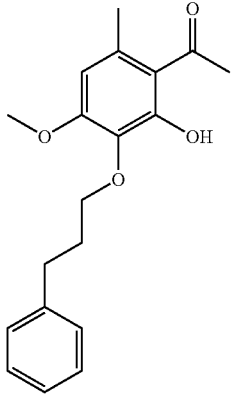 | >300 nM |
| 33a comparator | 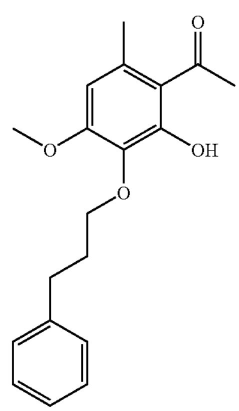 | >300 nM |
| comparator | 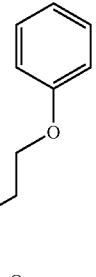 | >300 nM |

TABLE 1-continued

| Example Numbers | Structure | EC$_{50}$ Kv1.3 |
|---|---|---|
| comparator | AcNH–C$_6$H$_3$(C(O)CH$_2$CH$_2$CH$_3$)–O(CH$_2$)$_3$Ph | >300 nM |
| comparator | AcNH–C$_6$H$_3$(Ac)–O(CH$_2$)$_3$Ph | >300 nM |
| comparator | H$_2$N–C$_6$H$_3$(Ac)–O(CH$_2$)$_3$Ph | >300 nM |
| comparator | MeO–C$_6$H$_3$(Ac)–NH(CH$_2$)$_3$Ph | >300 nM |
| comparator | MeO–C$_6$H$_3$(Ac)–NHC(=O)(CH$_2$)$_2$Ph | >300 nM |

Selectivity Data

EC$_{50}$ values for inhibition of Kv1.1 and Kv1.5 currents were determined by the method according to Schmitz et al (2005) Molecular Pharmacology 68, 1254-1270 with the following differences:

1. Chinese Hamster Ovary (CHO) cells stably transfected with hKv1.1 and hKv1.5 were used in place of transfected rat L929 cells.
2. All electrophysiology was performed using planar patch clamp (Port-A-Patch, Nanion Technologies Gmbh, Munich) in contrast to conventional patch clamp.
3. EC50 values shown were determined from averaged dose response data obtained from 3 or more cells.

Example 7d Selectivity for Kv1.3 over Kv1.1: 45-fold, selectivity for Kv1.3 over Kv1.5: 37-fold.

Example 8b Selectivity for Kv1.3 over Kv1.1: 33-fold, selectivity for Kv1.3 over Kv1.5: 35-fold.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The claims defining the invention are as follows:

1. A compound of formula (I) or a salt thereof:

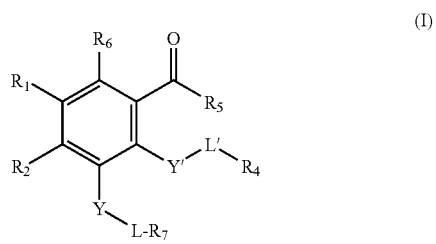

wherein

R$_1$ is independently selected from hydrogen, cyano, halo, nitro, optionally substituted lower alkyl, optionally substituted aryl, —OR, —C(O)R, —C(O)OR, —OC(O)R (where R is selected from hydrogen, optionally substituted alkyl, optionally substituted alkenyl, optionally substituted alkynyl, optionally substituted C$_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl);

R$_2$ is —OR;

R$_6$ is selected from cyano, halo, nitro, optionally substituted alkyl, optionally substituted alkenyl, optionally substituted alkynyl, optionally substituted aryl, optionally substituted heteroaryl, optionally substituted C$_{3-7}$ cycloalkyl, optionally substituted C$_{4-7}$ cycloalkenyl, —OR, —SR, —C(O)R, —C(O)OR, —OC(O)R (where R is selected from hydrogen, optionally substituted lower alkyl, lower alkenyl, lower alkynyl, optionally substituted C$_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl);

L is a divalent linker group of 2-6 atoms in length selected from optionally substituted C$_{2-6}$ alkylene, optionally substituted C$_{2-6}$ alkenylene, or optionally substituted C$_{2-6}$ alkynylene;

L' is
(i) a divalent linker group of 2-6 atoms in length selected from optionally substituted C$_{2-6}$ alkylene, optionally substituted C$_{2-6}$ alkenylene, or optionally substituted C$_{2-6}$ alkynylene; or
(ii) —CH$_2$—;

Y is —O—;

Y' is —O—;

R$_5$ is selected from optionally substituted alkyl, —OR, —C(O)R, —C(O)OR, SR, (where R is selected from optionally substituted C$_{2-7}$ alkyl, optionally substituted alkenyl, optionally substituted alkynyl, optionally substituted C$_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl);

R$_4$ is selected from substituted aryl, substituted aryloxy, optionally substituted heteroaryl, optionally substituted heteroaryloxy, optionally substituted heterocyclyl, optionally substituted heterocyclyloxy or —NR'''R"" (where R''' is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl, and where R"" is selected from optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl); and $R_7$ is selected from optionally substituted aryl, optionally substituted aryloxy, optionally substituted heteroaryl, optionally substituted heteroaryloxy, optionally substituted heterocyclyl, optionally substituted heterocyclyloxy or —NHR'" (where R'" is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl).

2. A compound according to claim 1 or a salt thereof wherein $R_1$ is independently selected from cyano, halo, nitro, optionally substituted lower alkyl, optionally substituted aryl, —OR, —C(O)R, —C(O)OR, —OC(O)R (where R is selected from hydrogen, optionally substituted alkyl, optionally substituted alkenyl, optionally substituted alkynyl, optionally substituted $C_{3-7}$ cycloalkyl, optionally substituted heterocyclyl, optionally substituted heteroaryl, and optionally substituted aryl), —C(O)NR'R", —NR'C(O)R" and —NR'R" (where R' and R" are independently selected from hydrogen or lower alkyl).

3. A compound according to claim 1 or a salt thereof wherein $R_1$ is independently selected from hydrogen, cyano, halo, optionally substituted lower alkyl, —O-optionally substituted lower alkyl, —C(O)-optionally substituted lower alkyl, and —C(O)NR'R" (wherein R' and R" are independently selected from hydrogen or lower alkyl).

4. A compound according to claim 1 or a salt thereof wherein $R_6$ is selected from cyano, halo, optionally substituted alkyl, optionally substituted alkenyl, optionally substituted alkynyl, optionally substituted heteroaryl, optionally substituted $C_{3-7}$ cycloalkyl, —O-optionally substituted lower alkyl, —O-optionally substituted $C_{3-7}$ cycloalkyl, or —O-optionally substituted heteroaryl.

5. A compound according to claim 4 or a salt thereof wherein $R_6$ is selected from halo, optionally substituted alkyl, or —O-optionally substituted lower alkyl.

6. A compound according to claim 1 or a salt thereof wherein L is a divalent linker group of 2-6 atoms in length selected from $C_{2-6}$ alkylene, $C_{2-6}$ alkenylene, or $C_{2-6}$ alkynylene, each of which may be optionally substituted by a lower alkyl group.

7. A compound according to claim 1 or a salt thereof wherein L' is a divalent linker group of 1-6 atoms in length selected from $C_{1-6}$ alkylene, $C_{2-6}$ alkenylene, or $C_{2-6}$ alkynylene.

8. A compound according to claim 1 or a salt thereof wherein $R_7$ is selected from optionally substituted aryl, optionally substituted aryloxy, optionally substituted heteroaryl, optionally substituted heteroaryloxy, optionally substituted heterocyclyl, or optionally substituted heterocyclyloxy.

9. A compound according to claim 8 or a salt thereof wherein $R_7$ is optionally substituted aryl.

10. A compound according to claim 1 or a salt thereof wherein $R_4$ is selected from optionally substituted heteroaryl, optionally substituted heteroaryloxy, optionally substituted heterocyclyl, optionally substituted heterocyclyloxy, or —NH$C_{3-7}$ cycloalkyl.

11. A compound according to claim 10 or a salt thereof wherein $R_4$ is selected from optionally substituted heteroaryl, optionally substituted heteroaryloxy, optionally substituted heterocyclyl, or —NH$C_{3-7}$ cycloalkyl.

12. A compound according to claim 1 or a salt thereof wherein $R_4$ is selected from azetidinyl, pyrrolidinyl, pyrazolinyl, pyrazolidinyl, imidazolinyl, imidazolidinyl, pyrrolinyl (including 2 and 3 pyrrolinyls), dioxolane, furyl, thienyl, pyrrolyl, H-pyrrolyl, oxazolyl, oxadiazolyl, (including 1,2,3 and 1,2,4 oxadiazolyls) thiazolyl, isoxazolyl, furazanyl, isothiazolyl, pyrazolyl, imidazolyl, triazolyl (including 1,2,3 and 1,3,4 triazolyls), tetrazolyl, and thiadiazolyl (including 1,2,3 and 1,3,4 thiadiazolyls), pyridyl, pyrimidinyl, pyridazinyl, pyrazinyl, pyranyl (including 2H and 4H pyranyls), piperidinyl, morpholinyl, piperazinyl, 1,3,5-trithianyl, thiomorpholinyl, 1-oxo-thiomorpholinyl, 1,1-dioxothiomorpholinyl, 1,4-dithianyl, and 1,4-dioxanyl;

all of which may be optionally substituted with one or more groups selected from halogen, $C_{1-6}$ alkyl, $C_{2-6}$ alkenyl, $C_{2-6}$ alkynyl, $C_{1-6}$ haloalkyl (in particular —$CF_3$), $C_{1-6}$ haloalkoxy (such as —$OCF_3$), —OH, phenyl, benzyl, phenoxy, benzyloxy, benzoyl, —$NH_2$, —$NHC_{1-4}$ alkyl, —$N(C_{1-4}$ alkyl$)_2$, —CN, —$NO_2$, mercapto, $C_{1-6}$ alkylcarbonyl, $C_{1-6}$alkoxycarbonyl and $CO_2H$.

13. A compound according to claim 1 or a salt thereof wherein L is an optionally substituted propylene or butylene.

14. A compound according to claim 13 or a salt thereof wherein L is —$CH_2$—$CH_2$—$CH(CH_3)$—, —$CH_2$—$CH_2$—$CH_2$—$CH_2$—, or —$CH_2$—$CH_2$—$CH_2$—.

15. A compound according to claim 1 or a salt thereof wherein $R_5$ is methyl.

16. A compound according to claim 1 or a salt thereof wherein $R_6$ is $C_{1-3}$ alkyl.

17. A compound according to claim 16 or a salt thereof wherein $R_6$ is methyl.

18. A compound selected from the group consisting of:
1-(3-Chloro-5-(3-(4-fluorophenyl)propoxy)-4-methoxy-2-methyl-6-(2-morpholinoethoxy)phenyl)ethanone;
1-(3-Chloro-6-(cyclopentylamino)ethoxy)-5-(3-(4-fluorophenyl)propoxy-4-methoxy-2-methylphenyl)ethanone;
1-[3-[3-(4-Fluoro-phenyl)-propoxy]-4-methoxy-5,6-dimethyl-2-(2-morpholin-4-yl-ethoxy)-phenyl]-ethanone;
1-[3-[3-(4-Fluoro-phenyl)-butoxy]-4-methoxy-5,6-dimethyl-2-(2-pyridin-2-yl-ethoxy)-phenyl]-ethanone;
1-[3-[3-(4-Fluoro-phenyl)-butoxy]-4-methoxy-5,6-dimethyl-2-(2-morpholin-4-yl-ethoxy)-phenyl]-ethanone;
1-{2-(2-Cyclopentylamino-ethoxy)-3-[3-(4-fluoro-phenyl)-butoxy]-4-methoxy-5,6-dimethyl-phenyl}-ethanone;
1-[3-Chloro-5-[3-(4-fluoro-phenyl)-butoxy]-4-methoxy-2-methyl-6-(2-pyridin-2-yl-ethoxy)-phenyl]-ethanone;
1-[3-Chloro-5-[3-(4-fluoro-phenyl)-butoxy]-4-methoxy-2-methyl-6-(2-morpholin-4-yl-ethoxy)-phenyl]-ethanone;
1-[3-Chloro-6-(2-cyclopentylamino-ethoxy)-5-[3-(4-fluoro-phenyl)-butoxy]-4-methoxy-2-methyl-phenyl]-ethanone;
1-[3-Chloro-5-[3-(4-fluoro-phenyl)-butoxy]-4-methoxy-2-methyl-6-(2-piperidin-1-yl-ethoxy)-phenyl]-ethanone;
1-{3-Chloro-5-[3-(4-fluoro-phenyl)-butoxy]-6-[2-(4-fluoro-piperidin-1-yl)-ethoxy]-4-methoxy-2-methyl-phenyl}-ethanone;

1-{3-Chloro-5-[3-(4-fluoro-phenyl)-butoxy]-6-[2-(R-3-fluoro-pyrrolidin-1-yl)-ethoxy]-4-methoxy-2-methyl-phenyl}-ethanone;
1-[3-Chloro-5-[3-(4-fluoro-phenyl)-butoxy]-4-methoxy-2-methyl-6-(pyridin-2-ylmethoxy)-phenyl]-ethanone;
1-{3-Chloro-5-[3-(4-fluoro-phenyl)-butoxy]-6-[2-(4-hydroxy-piperidin-1-yl)-ethoxy]-4-methoxy-2-methyl-phenyl}-ethanone;
1-{3-Chloro-5-[3-(4-fluoro-phenyl)-butoxy]-6-[2-(4-oxo-piperidin-1-yl)-ethoxy]-4-methoxy-2-methyl-phenyl}-ethanone;
1-{3-Chloro-6-[2-(4,4-difluoro-piperidin-1-yl)-ethoxy]-5-[3-(4-fluoro-phenyl)-butoxy]-4-methoxy-2-methyl-phenyl}-ethanone;
1-{3-Chloro-6-[2-(3,3-difluoro-piperidin-1-yl)-ethoxy]-5-[3-(4-fluoro-phenyl)-butoxy]-4-methoxy-2-methyl-phenyl}-ethanone;
1-{3-Chloro-5-[3-(4-fluoro-phenyl)-butoxy]-4-methoxy-2-methyl-6-[2-(pyrazin-2-yloxy)-ethoxy]-phenyl}-ethanone;
1-{3-Chloro-5-[3-(4-fluorophenyl)-butoxy]-4-methoxy-2-methyl-6-(2-[1,2,4]triazol-1-yl-ethoxy)-phenyl}-ethanone;
1-{3-Chloro-6-[2-(3,3-difluoro-azetidin-1-yl)-ethoxy]-5-[3-(4-fluoro-phenyl)-butoxy]-4-methoxy-2-methyl-phenyl}-ethanone;
1-[3-Chloro-5-[3-(4-fluoro-phenyl)-butoxy]-4-methoxy-2-methyl-6-(3-morpholin-4-yl-propoxy)-phenyl]-ethanone;
1-{3-Chloro-6-[3-(1,1-dioxo-thiomorpholin-4-yl)-propoxy]-5-[3-(4-fluoro-phenyl)-butoxy]-4-methoxy-2-methyl-phenyl}-ethanone;
1-{3-Chloro-5-[3-(4-fluoro-phenyl)-butoxy]-4-methoxy-2-methyl-6-[3-(1-oxo-thiomorpholin-4-yl)-propoxy]-phenyl}-ethanone;
1-(3-Chloro-4-methoxy-2-methyl-6-(2-morpholinoethoxy)-5-5 (4-phenyl butyl)phenyl)ethanone;
1-(3-Chloro-4-methoxy-2-methyl-5-(4-phenylbutyl)-6-(2-(pyridine-2-yl)ethoxy)phenyl)ethanone;
1-(3-Chloro-5-(4-(4-fluorophenyl)pentyl)-4-methoxy-2-methyl-6-(2-morpholino ethoxy)phenyl)ethanone;
1-[3-Chloro-5-[4-(4-fluoro-phenyl)-pentyl]-4-methoxy-2-methyl-6-(2-pyridin-2-yl-ethoxy)-phenyl]-ethanone;
1-[4-Methoxy-6-methyl-2-(2-morpholin-4-yl-ethoxy)-3-(3-phenyl-propoxy)-phenyl]-ethanone;
1-[3-Chloro-6-(2-cyclopentylamino-ethoxy)-4-methoxy-2-methyl-5-(3-phenyl-propoxy)-phenyl]-ethanone;
1-[3-Chloro-6-[2-(3,3-difluoro-azetidin-1-yl)-ethoxy]-4-methoxy-2-methyl-5-(3-phenyl-propoxy)-phenyl]-ethanone;
1-[3-Chloro-4-methoxy-2-methyl-5-(3-phenyl-propoxy)-6-(2-thiomorpholin-4-yl-ethoxy)-phenyl]-ethanone;
1-[3-Chloro-6-[2-(3,3-difluoro-pyrrolidin-1-yl)-ethoxy]-4-methoxy-2-methyl-5-(3-phenyl-propoxy)-phenyl]-ethanone;
1-[3-Chloro-6-[2-(3-hydroxy-azetidin-1-yl)-ethoxy]-4-methoxy-2-methyl-5-(3-phenyl-propoxy)-phenyl]-ethanone;
1-{3-Chloro-6-[2-(3-oxo-azetidin-1-yl)-ethoxy]-4-methoxy-2-methyl-5-(3-phenyl-propoxy)-phenyl}-ethanone;
1-{3-Chloro-6-(2-dimethylamino-ethoxy)-5-[3-(4-fluoro-phenyl)-butoxy]-4-methoxy-2-methyl-phenyl}-ethanone;
1-[3-Chloro-5-[3-(4-fluoro-phenyl)-butoxy]-6-(2-imidazol-1-yl-ethoxy)-4-methoxy-2-methyl-phenyl]-ethanone; and
1-{3-Chloro-5-[3-(4-fluoro-phenyl)-butoxy]-4-methoxy-2-methyl-6-[2-((S)-3-methyl-morpholin-4-yl)-ethoxy]-phenyl}-ethanone,
or a salt thereof.

19. A pharmaceutical composition comprising one or more compounds according to claim 1 or a salt thereof and optionally a pharmaceutically acceptable carrier or diluent.

20. A pharmaceutical composition according to claim 19 further comprising an additional immunosuppressive compound or other multiple sclerosis therapeutic.

21. A pharmaceutical composition according to claim 20 wherein the additional immunosuppressive compound or other multiple sclerosis therapeutic is selected from interferon beta-1b, interferon beta-1a, glatiramer acetate, natalizumab or mitoxantrone.

* * * * *

UNITED STATES PATENT AND TRADEMARK OFFICE
CERTIFICATE OF CORRECTION

PATENT NO. : 8,202,513 B2  
APPLICATION NO. : 12/681763  
DATED : June 19, 2012  
INVENTOR(S) : Flynn et al.

Page 1 of 3

It is certified that error appears in the above-identified patent and that said Letters Patent is hereby corrected as shown below:

On the Title Page
At (Item 56), Page 2, column 1, line 23, under Other Publications, please change "SYNLRTT" to --SYNLETT--.
At (Item 56), Page 2, column 2, line 2, under Other Publications, please change "trimethy" to --trimethyl--.
At (Item 56), Page 2, column 2, line 2, under Other Publications, please change "[ 1,4Idioxepin" to --[ 1,4]dioxepin--.
At (Item 56), Page 2, column 2, line 25, under Other Publications, please change "2hydroxy" to --2-hydroxy--.

In the Specification
At column 1, line 55, please change "8 749)." to --8: 749).--.
At column 2, line 10, please change "8 749)" to --8: 749)--.
At column 3, line 47, please change "at" to --et--.
At column 7, lines 27-28, please change "1, 2, 3" to --1,2,3--.
At column 7, line 28, please change "1, 2, 4" to --1,2,4--.
At column 7, line 30, please change "1, 2, 3" to --1,2,3--.
At column 7, line 31, please change "1, 2, 3" to --1,2,3--.
At column 13, line 63, please change "substitutent" to --substituent--.
At column 14, line 36, please change "1, 2, 3" to --1,2,3--.
At column 14, line 36, please change "1, 2, 4" to --1,2,4--.
At column 14, line 38, please change "1, 2, 3" to --1,2,3--.
At column 14, line 39, please change "1, 2, 3" to --1,2,3--.
At column 18, line 28-29, please change "dermatitises," to --dermatitis,--.
At column 18, line 29, please change "seborrhoeis" to --seborrhoeic--.
At column 18, line 31, please change "greata," to --areata,--.
At column 18, line 35-36, please change "opthalmopathy," to --ophthalmopathy,--.
At column 18, line 62, please change "Sjoegren's" to --Sjogren's--.
At column 19, line 6, please change "ballous" to --bullous--.

Signed and Sealed this  
Eleventh Day of March, 2014

Michelle K. Lee  
*Deputy Director of the United States Patent and Trademark Office*

At column 19, line 8, please change "carcinogenis," to --carcinogenic,--.
At column 22, line 13, please change "zircononcene)." to --zirconocene).--.
At column 22, line 18, please change "zircononcene)." to --zirconocene).--.

At column 23-24, in the reaction scheme below line 35, please change " 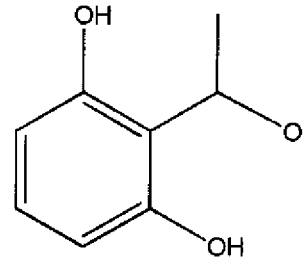 " to 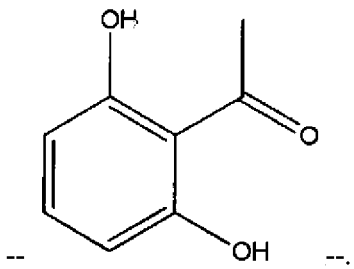 --.

At column 24, line 28, please change "Freidel" to --Friedel--.
At column 24, line 30, please change "chomenone" to --chromanone--.
At column 24, line 32, please change "chromenone" to --chromanone--.
At column 25, line 48, please change "R6)" to --R6).--.
At column 49, line 42, please change "(M+H$_+$)" to --(M+H$_+$).--.
At column 50, line 9, please change "(M+H$_+$)" to --(M+H$_+$).--.
At column 55, line 26-27, please change "29a) 2-[4-RS-(4-Flurophenyl)pentyl]-1,3-dimethoxy-5-methylbenzene" to --29a) 2-[4-*RS*-(4-Flurophenyl)pentyl]-1,3-dimethoxy-5-methylbenzene--.
At column 55, lines 59-60, please change "29b) 1-(3-(4-RS-(4-Flurophenyl)pentyl)-2,4-dimethoxy-6-methylphenyl)ethanone" to --29b) 1-(3-(4-*RS*-(4-Flurophenyl)pentyl)-2,4-dimethoxy-6-methylphenyl)ethanone--.
At column 56, lines 56-58, please change "29d) 1-{4-Methoxy-6-methyl-2-(2-morpholinoethoxy)-3-[4-RS-(4-fluorophenyl)pentyl)]phenyl}ethanone" to --29d) 1-{4-Methoxy-6-methyl-2-(2-morpholinoethoxy)-3-[4-*RS*-(4-fluorophenyl)pentyl)]phenyl}ethanone--.
At column 57, lines 28-29, please change "1-[3-[4-RS-(4-Fluorophenyl)pentyl]-4-methoxy-6-methyl-2-(2-pyridin-2-yl-ethoxy)phenyl]ethanone" to --1-[3-[4-*RS*-(4-Fluorophenyl)pentyl]-4-methoxy-6-methyl-2-(2-pyridin-2-yl-ethoxy)phenyl]ethanone--.
At column 66, lines 1-3, please change "1-{3-Chloro-5-[3-(4-fluoro-phenyl)-butoxyl]-4-methoxy-2-methyl-6-[2-((S)-3-methyl-morpholin-4-yl)-ethoxy]-phenyl}-ethanone" to --1-{3-Chloro-5-[3-(4-fluoro-phenyl)-butoxyl]-4-methoxy-2-methyl-6-[2-((*S*)-3-methyl-morpholin-4-yl)-ethoxy]-phenyl}-ethanone--.

CERTIFICATE OF CORRECTION (continued)
U.S. Pat. No. 8,202,513 B2

At column 72, structure 1f, please change " 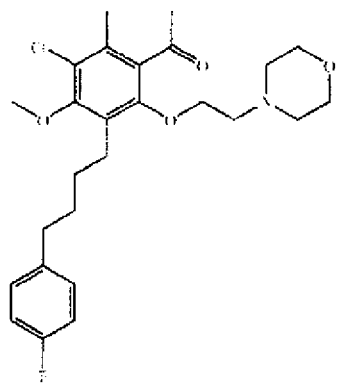 " to

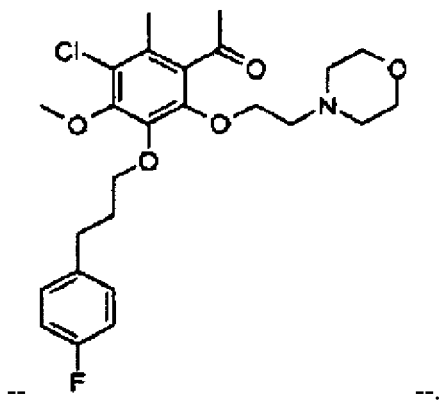 --.